United States Patent
Kumanogoh

(10) Patent No.: US 10,794,907 B2
(45) Date of Patent: Oct. 6, 2020

(54) THERAPEUTIC AGENT FOR AUTOIMMUNE DISEASES OR ALLERGY, AND METHOD FOR SCREENING FOR THE THERAPEUTIC AGENT

(71) Applicant: OSAKA UNIVERSITY, Suita-shi (JP)

(72) Inventor: Atsushi Kumanogoh, Osaka (JP)

(73) Assignee: OSAKA UNIVERSITY, Suita-shi (JP)

( * ) Notice: Subject to any disclaimer, the term of this patent is extended or adjusted under 35 U.S.C. 154(b) by 0 days.

(21) Appl. No.: 14/258,617

(22) Filed: Apr. 22, 2014

(65) Prior Publication Data

US 2014/0349311 A1 Nov. 27, 2014

Related U.S. Application Data

(62) Division of application No. 13/508,192, filed as application No. PCT/JP2010/006527 on Nov. 5, 2010, now abandoned.

(30) Foreign Application Priority Data

Nov. 5, 2009 (JP) ................................ 2009-254108

(51) Int. Cl.
| | |
|---|---|
| G01N 33/53 | (2006.01) |
| G01N 33/566 | (2006.01) |
| C07K 16/18 | (2006.01) |
| C07K 16/28 | (2006.01) |

(52) U.S. Cl.
CPC ........... *G01N 33/566* (2013.01); *C07K 16/18* (2013.01); *C07K 16/2863* (2013.01); *G01N 33/53* (2013.01); *C07K 2317/34* (2013.01); *G01N 2500/04* (2013.01)

(58) Field of Classification Search
None
See application file for complete search history.

(56) References Cited

U.S. PATENT DOCUMENTS

| 8,871,205 | B2 | 10/2014 | Ting et al. |
|---|---|---|---|
| 2005/0118168 | A1 | 6/2005 | Figdor et al. |
| 2007/0167607 | A1 | 7/2007 | Steinkasserer et al. |
| 2008/0025913 | A1 | 1/2008 | Bowdish et al. |
| 2008/0045443 | A1 | 2/2008 | Kikutani et al. |
| 2008/0213268 | A1 | 9/2008 | Watts et al. |
| 2013/0115214 | A1 | 5/2013 | Watts et al. |
| 2013/0149238 | A1 | 6/2013 | Kavilie et al. |
| 2015/0368327 | A1 | 12/2015 | Goshima et al. |

FOREIGN PATENT DOCUMENTS

| EP | 1 739 092 A1 | 1/2007 |
|---|---|---|
| JP | 2000-159670 A | 6/2000 |
| JP | 2003 502283 | 1/2003 |
| JP | 2006 523432 | 10/2006 |
| JP | 2008 504222 | 2/2008 |
| JP | 2009 514972 | 4/2009 |
| WO | WO 2014/123186 | 8/2014 |

OTHER PUBLICATIONS

Amano et al. (1996) J. Biol. Chem. 271: 20246-20249.*
Wu, Nie, Huse, and Watkins. Humanization of a murine monoclonal antibody by simultaneous optimization of framework and CDR residues. Journal of Molecular Biology, 1999. vol. 294, pp. 151-162.*
MacCallum R.M. et al, Antibody-antigen interactions: Contact analysis and binding site topography. J. Mol. Biol., 1998, vol. 262, p. 732-745.*
Casset F, et al. A peptide mimetic of an anti-CD4 monoclonal antibody by rational design. Biochemical and Biophysical Research Communications, 2003, vol. 307, p. 198-205.*
Skolnick and Fetrow. From genes to protein structure and function: novel applications of computational approaches in the genomic era. Trends in Biotechnology, 2000. vol. 18, pp. 34-39.*
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*
Tamagnone et al., "Signalling by Semaphorin Receptors: Cell Guidance and Beyond", Trends in Cell Biology, vol. 10, Sep. 2000, pp. 377-383.
Sengoku et al., "Effects of Tacrolimus Ointment on Type I (immediate and late) and IV (delayed) Cutaneous Allergic Reactions in Mice", Folia Pharmacol. Japan, vol. 112, 1998, pp. 221-232 (with English Abstract).
Wong, A.W., et al., "CIITA-regulated plexin-A1 affects T-cell-dendritic cell intractions," Nature Immunology, vol. 4, No. 9, pp. 891-898, (Sep. 2003).
Eun, S.Y., et al., "Cutting Edge: Rho Activation and Actin Polarization Are Dependent on Plexin-A1 in Dendritic Cells," Journal of Immunology, vol. 177, No. 7, pp. 4271-4275, (2006).
Tordjman, R., et al., "A neuronal receptor, neuropilin-I, is essential for the initiation of the primary immune response," Nature Immunology, vol. 3, No. 5, pp. 477-482, (Apr. 15, 2005).
Ohl, L., et al., "CCR7 Governs Skin Dendritic Cell Migration under Inflammatory and Steady-State Conditions," Immunity, vol. 21, pp. 279-288, (Aug. 2004).
Johnson, L.A., et al., "An inflammation-induced mechanism for leukocyte transmigration across lymphatic vessel endothelium," Journal of Experimental Medicine, vol. 203, No. 12, pp. 2763-2777, (Nov. 27, 2006).
Takegahara, N., et al., "Plexing-A1 and its interaction with DAP12 in immune responses and bone homeostasis," Nature Cell Biology, vol. 8, No. 6, pp. 615-622, (Jun. 2006).

(Continued)

*Primary Examiner* — Michael D Pak
(74) *Attorney, Agent, or Firm* — Oblon, McClelland, Maier & Neustadt, L.L.P.

(57) ABSTRACT

Disclosed is a therapeutic agent for treating a cellular immune disease, comprising as an active ingredient a substance that inhibits binding between Sema3A and a Neuropilin-1/Plexin-A1 heteroreceptor. The substance includes, for example, a Sema3A neutralizing antibody, a Neuropilin-1 neutralizing antibody, or a soluble Neuropilin-1 or derivative thereof. Also disclosed is a method for screening a therapeutic agent for treating a cellular immune disease utilizing a signal generated by the interactions of Neuropilin-1, Plexin-A1 and Sema3A as a marker.

9 Claims, 12 Drawing Sheets

Specification includes a Sequence Listing.

(56) References Cited

OTHER PUBLICATIONS

International Search Report dated Dec. 14, 2010 in PCT/JP10/06527 Filed Nov. 5, 2010.
Extended Search Report dated Mar. 19, 2013 in European Application No. 10828111.4.
Yves Lepelletier, et al., "Immunosuppressive role of semaphorin-3A on T cell proliferation is mediated by inhibition of actin cytoskeleton reorganization", Eur. J. Immunol., vol. 36, No. 7, Jul. 1, 2006, pp. 1782-1793.
Helen M. Flinn, et al., "Rho stimulates tyrosine phosphorylation of focal adhesion kinase, p130 and paxillin", Journal of Cell Science, vol. 109, No. 5, May 1, 1996, pp. 1133-1141.
Fanny Mann, et al., "Semaphorins in development and adult brain: Implication for neurological diseases", Progress in Neurobiology, vol. 82, No. 2, May 31, 2007, pp. 57-79.
International Search Report dated Aug. 9, 2016 in PCT/JP2016/069439 (with English translation of category of cited documents).
Yukiko Matsunaga, et al.. "Three-dimensional conformation of Semaphorin-related molecular groups" Experimental Medicine, vol. 31, No. 4, 2013, pp. 523-531 (with English language translation).
Kei Suzuki, et al., "Structure of the Plexin Ectodomain Bound by Semaphorin-Mimicking Antibodies" Plos One, vol. 16, No. 6, Jun. 3, 2016, pp. 1-17.
Alex L. Kolodkin, et al., "The semaphorin Genes Encode a Family of Transmembrane and Secreted Growth Cone Guidance Molecules" Cell Press, vol. 75, 1993, pp. 1389-1399.
Marc Tessier-Lavigne, et al., "The Molecular Biology of Axon Guidance" Science, vol. 274, Nov. 15, 1996, pp. 1123-1133.
R. Jeroen Pasterkamp, et al., "Semaphorin junction: making tracks toward neural connectivity" Current Opinion in Neurobiology, vol. 13, 2003, pp. 79-89.
Bert J. C. Janssen, et al., "Neuropilins lock secreted semaphorins onto plexins in a ternary signaling complex" Nature Structural & Molecular Biology, vol. 19, No. 12, Dec. 2012, pp. 1293-1299.
Kenzen Kou, et al., "Decreased Expression of Semaphorin-3A, a Neurite-collapsing Factor, is Associated With Itch in Psoriatic Skin" Acta Derm Venereol, vol. 92, 2012, pp. 521-528.
Mitsutoshi Tominaga, et al., "Psoralen-ultraviolet A therapy alters epidermal Sema3A and NGF levels and modulates epidermal innervation in atopic dermatitis" Journal of Dermatological Science, vol. 55, 2009, pp. 40-46.
Junko Yamaguchi, et al., "Semaphorin3A Alleviates Skin Lesions and Scratching Behavior in NC/Nga Mice, an Atopic Dermatitis Model" Journal of Investigative Dermatology, vol. 128, 2008, pp. 2842-2849.
Osamu Negi, et al., "Topically applied semaphoring 3A ointment inhibits scratching behaviors and improves skin inflammation in NC/Nga mice with atopic dermatitis" Journal of Dermatological Science, vol. 66, 2012, pp. 37-43.
Haruna Sawaki, et al., "Intranasal Administration of Semaphorin-3A Alleviates Sneezing and Nasal Rubbing in a Murine Model of Allergic Rhinitis" Journal of Pharmacological Sciences, vol. 117, 2011, pp. 34-44.
Mikihito Hayashi, et al., "Osteoprotection by semaphoring 3A" Nature, vol. 485, May 3, 2012, pp. 69-74.
Toru Fukuda, et al., "Sema3A regulates bone-mass accrual through sensory innervations" Nature, vol. 497, May 23, 2013, pp. 490-493.
Alfonso Catalano, "The Neuroimmune Semaphorin-3A Reduces Inflammation and Progression of Experimental Autoimmune Arthritis" The Journal of Immunology, vol. 185, Oct. 2010, pp. 6373-6383.
Zahava Vadasz, et al., "Semaphorin 3A is a marker for disease activity and a potential immunoregulator in systemic lupus erythematosus" Arthritis Research and Therapy, vol. 14, 2012, 8 Pages.
Goutam Chakraborty, et al., "Semaphorin 3A Suppresses Tumor Growth and Metastasis in Mice Melanoma Model" Plos One, vol. 7, No. 3, Mar. 2012, 13 Pages.
Naoya Yamashita, et al., "Anti-Semaphorin 3A neutralization monoclonal antibody prevents sepsis development in lipopolysaccharide-treated mice" International Immunology, vol. 27, No. 9, 2015, pp. 459-466.
Office Action dated Aug. 13, 2014, in European patent application No. 10828111.4.
European Communication Pursuant to Article 94(3) EPC dated May 27, 2016 in Patent Application No. 1 0 828 111.4.
"Treatments for Type IV Hypersensitivity -RightDiagnosis.com" Retrieved from the Internet: URL:http://www.rightdiaonosis.com/t/type_iv_hypersensitivity/treatments.htm, XP55273451, retrieved on May 18, 2016, 2014, 1 Page.
Kaila et al, "Diazine Indole Acetic Acids as Potent, Selective, and Orally Bioavailable Antagonists of Chemoattractant Receptor . . . ", J. Med. Chem., 2012, vol. 55, pp. 5088-5109.
Peterson et al, "In vivo, Pharmacological Disease Models for Psoriasis and Atopic Dermatitis in Drug Discovery", Basic & Clinical Pharmacology & Toxicology, 2006, vol. 99, pp. 104-115.
Lee et al, "Anti-inflammatory and barrier protecting effect of Lithospermum erythrorhizon extracts in chronic . . . ", Letters to the Editor/Journal of Dermatological Science, 2009, vol. 56, pp. 64-66.
Summons to attend Oral Proceedings, issued Apr. 7, 2017, in European patent application No. 10828111.4.
Engeman et al, "Inhibition of Functional T Cell Priming and Contact Hypersensitivity Responses by Treatment with Anti-Secondary Lymphoid Chemokine Antibody during Hapten Sensitization", The Journal of Immunology, 2000, vol. 164, No. 10, pp. 5207-5214.
Office Action dated Jan. 10, 2019 in the corresponding European Application No. 17 189 095.7 6 pages.
Extended European Search Report dated Jan. 3, 2019 in the corresponding European Application No. 16818027.1 8 pages.
Montolio, M., et al., "A Semaphorin 3 A Inhibitor Blocks Axonal Chemorepulsion and Enhances Axon Regeneration", Chemistry and Biology, vol. 16, No. 7, XP055537802, Jul. 1, 2009, pp. 691-701.
Sarris, M., et al., "Neuropilin-1 Expression on Regulatory T Cells Enhances Their Interactions with Dendritic Cells during Antigen Recognition", Immunity., Vo. 28, No. 3, XP055537835, Mar. 1, 2008, pp. 402-413.
Kumanogoh, A., et al., "Immunological functions of the neuropilins and plexins as receptors for semaphorins", Nature Reviews Immunology, vol. 13, No. 11, XP055533669, Nov. 1, 2013, pp. 802-814.
Takamatsu, H., et al., "Diverse roles for semaphorin-plexin signaling in the immune system", Trends in Immunology, vol. 33, No. 3, XP028402493, Mar. 1, 2012, pp. 127-135.
Hota, P. K., et al., "Plexin structures are coming: opportunities for multilevel investigations of semaphorin guidance receptors, their cell signaling mechanisms, and functions", Cellular and Molecular Life Sciences., vol. 69, No. 22, XP055533719, Jun. 29, 2012, pp. 3765-3805.
Non-Final Office Action dated Jul. 8, 2019, in U.S. Appl. No. 15/741,225 (19 pages).
Plexin A1 Antibody #3813 data sheet (Cell Signaling Technology, 2015) 1 page.
Bielenberg et al, "Increased Smooth Muscle Contractility in Mice Deficient for Neuropilin 2", Am. J. Path., 2012, vol. 181, No. 2, pp. 548-559.

* cited by examiner

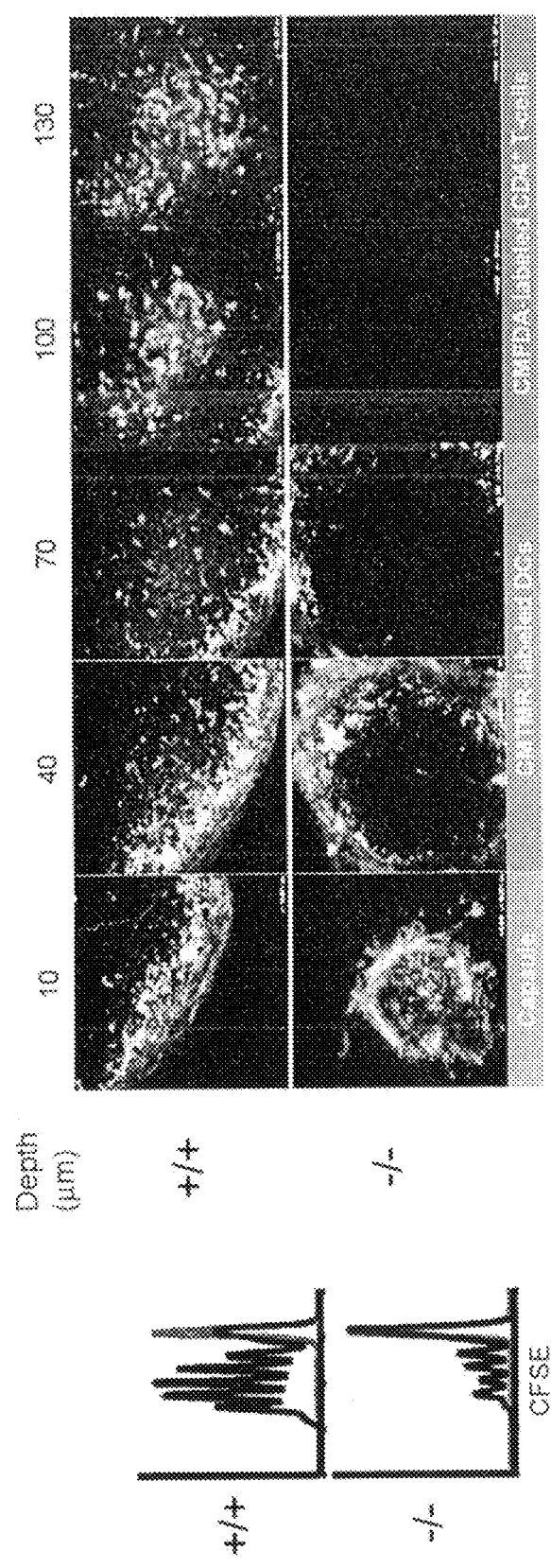

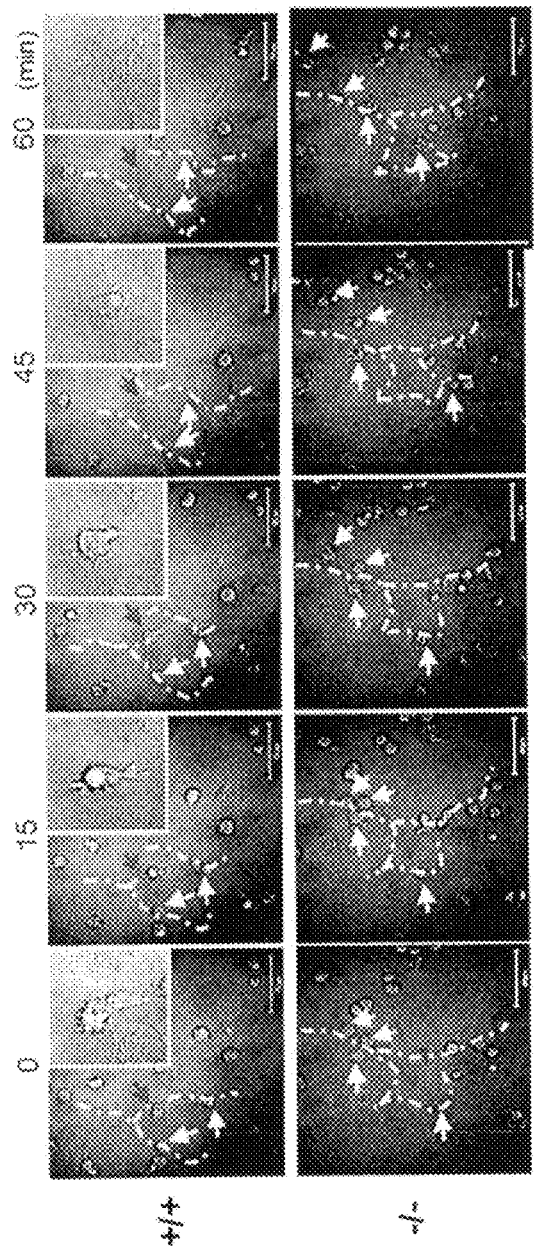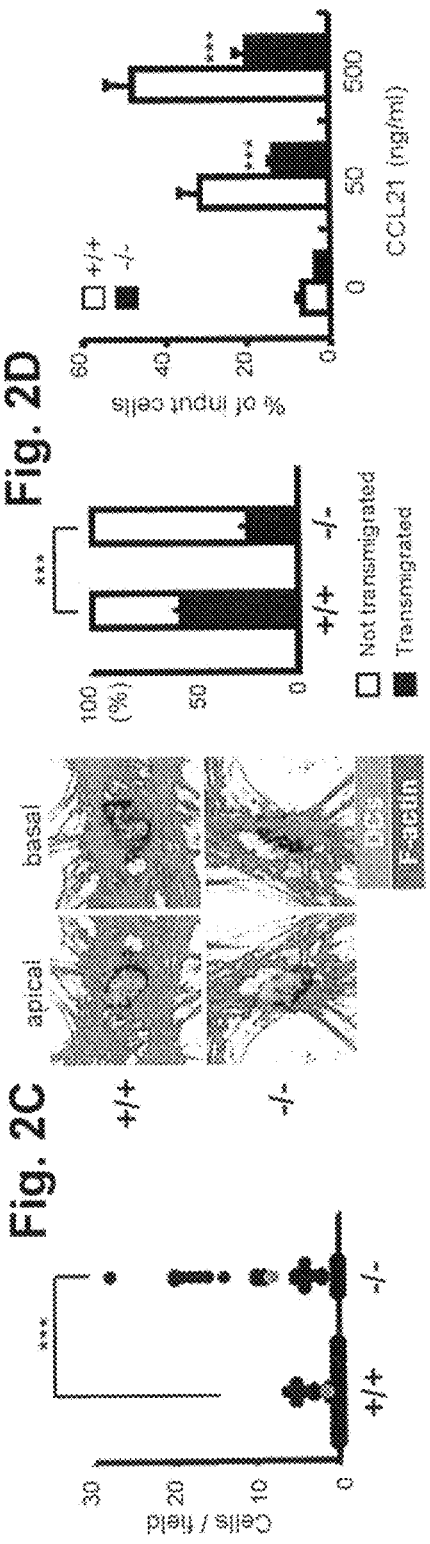

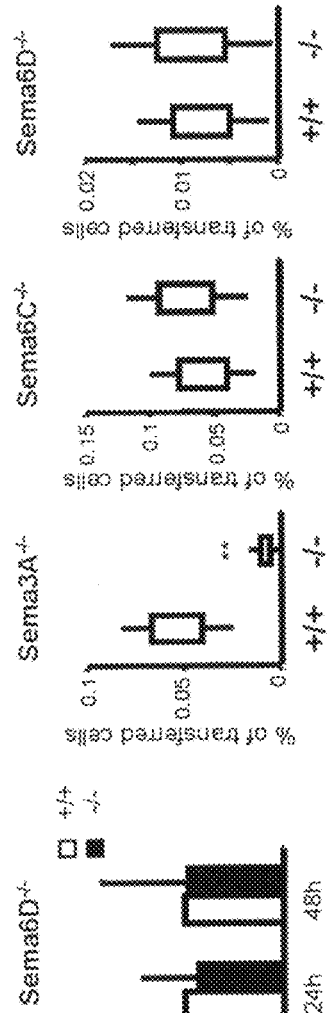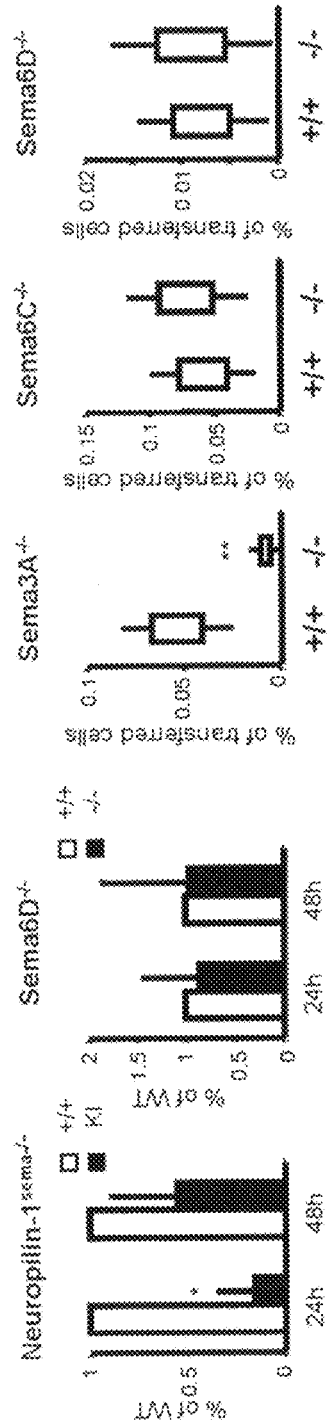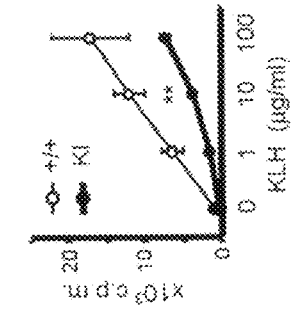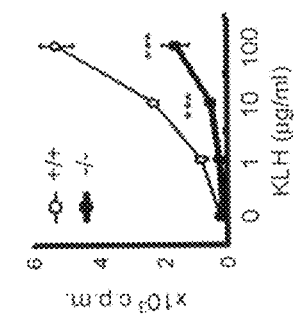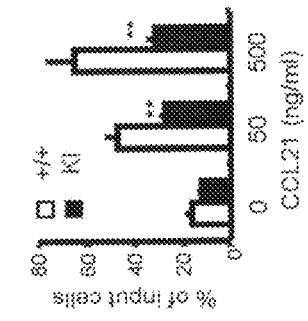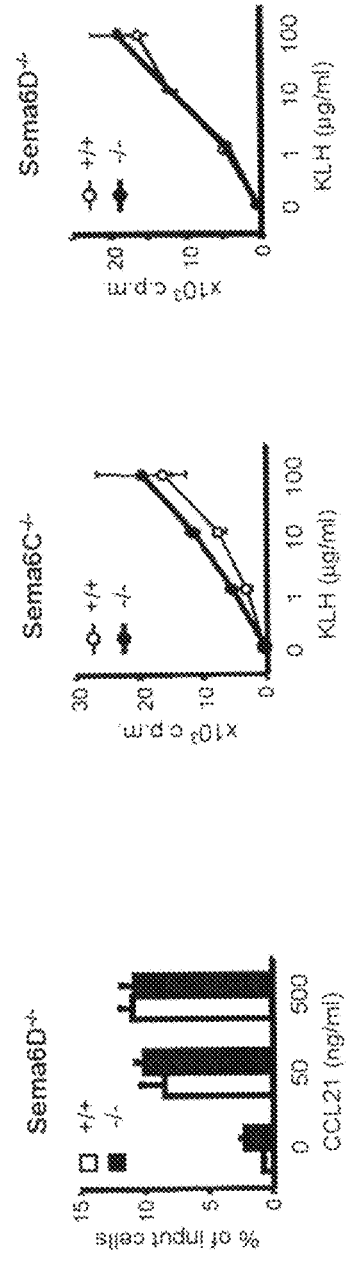
Fig. 3A  Fig. 3B  Fig. 3C  Fig. 3D

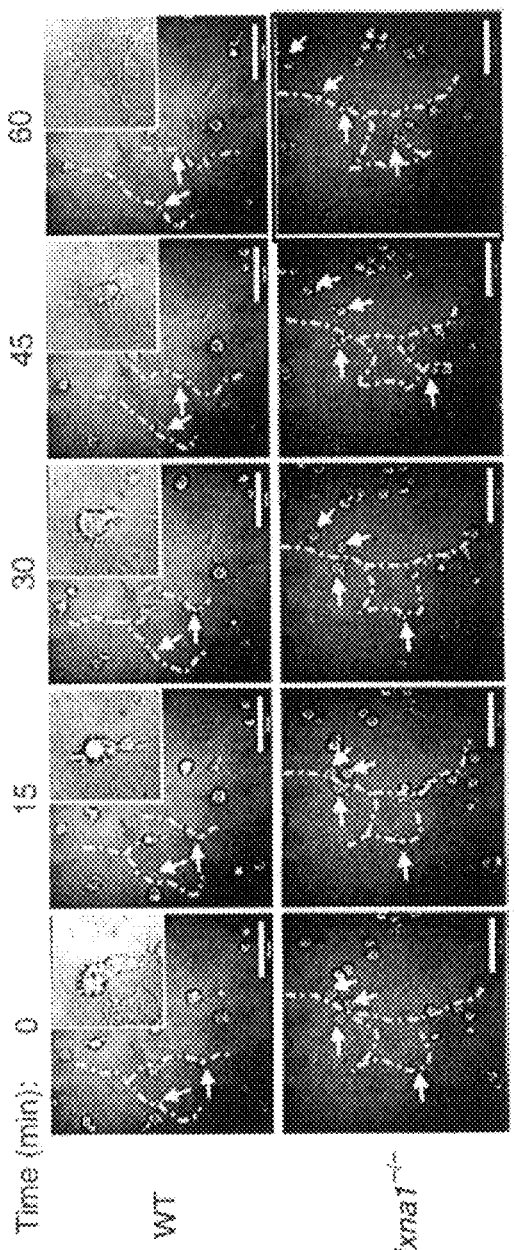
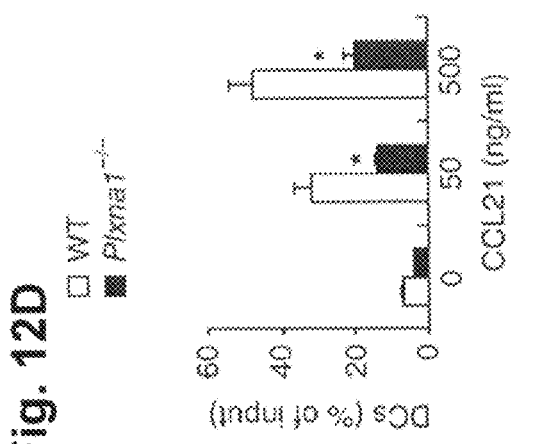
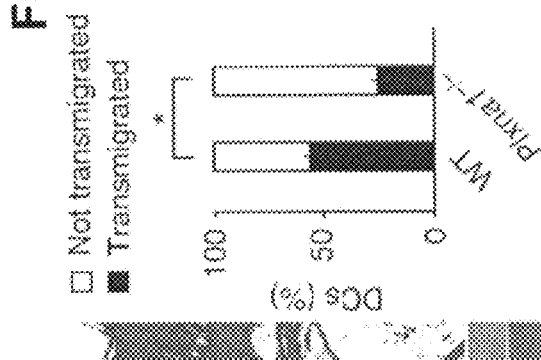
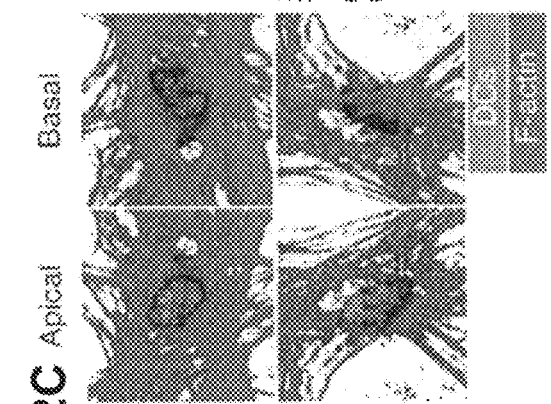
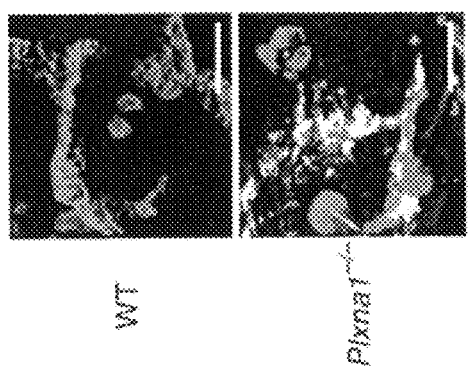

SEQUENCE LISTING

<160> NUMBER OF SEQ ID NOS: 16

<210> SEQ ID NO 1
<211> LENGTH: 771
<212> TYPE: PRT
<213> ORGANISM: homo sapiens

<400> SEQUENCE: 1

Met Gly Trp Leu Thr Arg Ile Val Cys Leu Phe Trp Gly Val Leu Leu
1               5                   10                  15

Thr Ala Arg Ala Asn Tyr Gln Asn Gly Lys Asn Asn Val Pro Arg Leu
            20                  25                  30

```
Lys Leu Ser Tyr Lys Glu Met Leu Glu Ser Asn Asn Val Ile Thr Phe
        35                  40                  45

Asn Gly Leu Ala Asn Ser Ser Tyr His Thr Phe Leu Leu Asp Glu
    50                  55                  60

Glu Arg Ser Arg Leu Tyr Val Gly Ala Lys Asp His Ile Phe Ser Phe
65                  70                  75                  80

Asp Leu Val Asn Ile Lys Asp Phe Gln Lys Ile Val Trp Pro Val Ser
                85                  90                  95

Tyr Thr Arg Arg Asp Glu Cys Lys Trp Ala Gly Lys Asp Ile Leu Lys
            100                 105                 110

Glu Cys Ala Asn Phe Ile Lys Val Leu Lys Ala Tyr Asn Gln Thr His
            115                 120                 125

Leu Tyr Ala Cys Gly Thr Gly Ala Phe His Pro Ile Cys Thr Tyr Ile
    130                 135                 140

Glu Ile Gly His His Pro Glu Asp Asn Ile Phe Lys Leu Glu Asn Ser
145                 150                 155                 160

His Phe Glu Asn Gly Arg Gly Lys Ser Pro Tyr Asp Pro Lys Leu Leu
                165                 170                 175

Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
            195                 200                 205

His Pro Ile Arg Thr Glu Gln His Asp Ser Arg Trp Leu Asn Asp Pro
    210                 215                 220

Lys Phe Ile Ser Ala His Leu Ile Ser Glu Ser Asp Asn Pro Glu Asp
225                 230                 235                 240

Asp Lys Val Tyr Phe Phe Phe Arg Glu Asn Ala Ile Asp Gly Glu His
                245                 250                 255

Ser Gly Lys Ala Thr His Ala Arg Ile Gly Gln Ile Cys Lys Asn Asp
            260                 265                 270

Phe Gly Gly His Arg Ser Leu Val Asn Lys Trp Thr Thr Phe Leu Lys
            275                 280                 285

Ala Arg Leu Ile Cys Ser Val Pro Gly Pro Asn Gly Ile Asp Thr His
    290                 295                 300

Phe Asp Glu Leu Gln Asp Val Phe Leu Met Asn Phe Lys Asp Pro Lys
305                 310                 315                 320

Asn Pro Val Val Tyr Gly Val Phe Thr Thr Ser Ser Asn Ile Phe Lys
                325                 330                 335

Gly Ser Ala Val Cys Met Tyr Ser Met Ser Asp Val Arg Arg Val Phe
            340                 345                 350

Leu Gly Pro Tyr Ala His Arg Asp Gly Pro Asn Tyr Gln Trp Val Pro
            355                 360                 365

Tyr Gln Gly Arg Val Pro Tyr Pro Arg Pro Gly Thr Cys Pro Ser Lys
    370                 375                 380

Thr Phe Gly Gly Phe Asp Ser Thr Lys Asp Leu Pro Asp Asp Val Ile
385                 390                 395                 400

Thr Phe Ala Arg Ser His Pro Ala Met Tyr Asn Pro Val Phe Pro Met
            405                 410                 415

Asn Asn Arg Pro Ile Val Ile Lys Thr Asp Val Asn Tyr Gln Phe Thr
            420                 425                 430

Gln Ile Val Val Asp Arg Val Asp Ala Glu Asp Gly Gln Tyr Asp Val
    435                 440                 445
```

```
Met Phe Ile Gly Thr Asp Val Gly Thr Val Leu Lys Val Val Ser Ile
450                 455                 460

Pro Lys Glu Thr Trp Tyr Asp Leu Glu Val Leu Leu Glu Met
465                 470                 475                 480

Thr Val Phe Arg Glu Pro Thr Ala Ile Ser Ala Met Glu Leu Ser Thr
                485                 490                 495

Lys Gln Gln Gln Leu Tyr Ile Gly Ser Thr Ala Gly Val Ala Gln Leu
                500                 505                 510

Pro Leu His Arg Cys Asp Ile Tyr Gly Lys Ala Cys Ala Glu Cys Cys
                515                 520                 525

Leu Ala Arg Asp Pro Tyr Cys Ala Trp Asp Gly Ser Ala Cys Ser Arg
530                 535                 540

Tyr Phe Pro Thr Ala Lys Arg Arg Thr Arg Arg Gln Asp Ile Arg Asn
545                 550                 555                 560

Gly Asp Pro Leu Thr His Cys Ser Asp Leu His His Asp Asn His His
                565                 570                 575

Gly His Ser Pro Glu Glu Arg Ile Ile Tyr Gly Val Glu Asn Ser Ser
                580                 585                 590

Thr Phe Leu Glu Cys Ser Pro Lys Ser Gln Arg Ala Leu Val Tyr Trp
                595                 600                 605

Gln Phe Gln Arg Arg Asn Glu Glu Arg Lys Glu Glu Ile Arg Val Asp
                610                 615                 620

Asp His Ile Ile Arg Thr Asp Gln Gly Leu Leu Leu Arg Ser Leu Gln
625                 630                 635                 640

Gln Lys Asp Ser Gly Asn Tyr Leu Cys His Ala Val Glu His Gly Phe
                645                 650                 655

Ile Gln Thr Leu Leu Lys Val Thr Leu Glu Val Ile Asp Thr Glu His
                660                 665                 670

Leu Glu Glu Leu Leu His Lys Asp Asp Gly Asp Gly Ser Lys Thr
                675                 680                 685

Lys Glu Met Ser Asn Ser Met Thr Pro Ser Gln Lys Val Trp Tyr Arg
                690                 695                 700

Asp Phe Met Gln Leu Ile Asn His Pro Asn Leu Asn Thr Met Asp Glu
705                 710                 715                 720

Phe Cys Glu Gln Val Trp Lys Arg Asp Arg Lys Gln Arg Gln Arg
                725                 730                 735

Pro Gly His Thr Pro Gly Asn Ser Asn Lys Trp Lys His Leu Gln Glu
                740                 745                 750

Asn Lys Lys Gly Arg Asn Arg Thr His Glu Phe Glu Arg Ala Pro
                755                 760                 765

Arg Ser Val
        770

<210> SEQ ID NO 2
<211> LENGTH: 923
<212> TYPE: PRT
<213> ORGANISM: Homo sapiens

<400> SEQUENCE: 2

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
                20                  25                  30

Ile Glu Ser Pro Gly Tyr Leu Thr Ser Pro Gly Tyr Pro His Ser Tyr
                35                  40                  45
```

-continued

```
His Pro Ser Glu Lys Cys Glu Trp Leu Ile Gln Ala Pro Asp Pro Tyr
     50                  55                  60

Gln Arg Ile Met Ile Asn Phe Asn Pro His Phe Asp Leu Glu Asp Arg
 65                  70                  75                  80

Asp Cys Lys Tyr Asp Tyr Val Glu Val Phe Asp Gly Glu Asn Glu Asn
                 85                  90                  95

Gly His Phe Arg Gly Lys Phe Cys Gly Lys Ile Ala Pro Pro Pro Val
                100                 105                 110

Val Ser Ser Gly Pro Phe Leu Phe Ile Lys Phe Val Ser Asp Tyr Glu
            115                 120                 125

Thr His Gly Ala Gly Phe Ser Ile Arg Tyr Glu Ile Phe Lys Arg Gly
130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
                180                 185                 190

Asp Leu Glu Pro Asp Ser Asn Pro Pro Gly Gly Met Phe Cys Arg Tyr
            195                 200                 205

Asp Arg Leu Glu Ile Trp Asp Gly Phe Pro Asp Val Gly Pro His Ile
210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
            275                 280                 285

Asp Gln Ile Thr Ala Ser Ser Gln Tyr Ser Thr Asn Trp Ser Ala Glu
290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
                340                 345                 350

Tyr Tyr Val Lys Thr Tyr Lys Ile Asp Val Ser Ser Asn Gly Glu Asp
            355                 360                 365

Trp Ile Thr Ile Lys Glu Gly Asn Lys Pro Val Leu Phe Gln Gly Asn
            370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
                420                 425                 430

Gly Met Leu Gly Met Val Ser Gly Leu Ile Ser Asp Ser Gln Ile Thr
            435                 440                 445

Ser Ser Asn Gln Gly Asp Arg Asn Trp Met Pro Glu Asn Ile Arg Leu
450                 455                 460
```

```
Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
            485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
        515                 520                 525

Ile Met Asp Asp Ser Lys Arg Lys Ala Lys Ser Phe Glu Gly Asn Asn
    530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Leu Val Asp Glu Cys Asp Asp Gln Ala
        595                 600                 605

Asn Cys His Ser Gly Thr Gly Asp Asp Phe Gln Leu Thr Gly Gly Thr
    610                 615                 620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
            660                 665                 670

Trp Ser Val Leu Thr Ser Lys Thr Gly Pro Ile Gln Asp His Thr Gly
        675                 680                 685

Asp Gly Asn Phe Ile Tyr Ser Gln Ala Asp Glu Asn Gln Lys Gly Lys
    690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Ala Ile Gly His Gln Gly Asp His Trp Lys Glu Gly Arg Val
        755                 760                 765

Leu Leu His Lys Ser Leu Lys Leu Tyr Gln Val Ile Phe Glu Gly Glu
    770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
            820                 825                 830

Tyr Glu Gly Glu Gly Glu Gly Asp Lys Asn Ile Ser Arg Lys Pro Gly
        835                 840                 845

Asn Val Leu Lys Thr Leu Asp Pro Ile Leu Ile Thr Ile Ile Ala Met
    850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
```

```
                    885                 890                 895
Glu Asn Tyr Asn Phe Glu Leu Val Asp Gly Val Lys Leu Lys Lys Asp
                900                 905                 910
Lys Leu Asn Thr Gln Ser Thr Tyr Ser Glu Ala
            915                 920
```

<210> SEQ ID NO 3
<211> LENGTH: 1873
<212> TYPE: PRT
<213> ORGANISM: Homo sapiens

<400> SEQUENCE: 3

```
Met Trp Ala Glu Ala Gly Leu Pro Arg Ala Gly Gly Gly Ser Gln Pro
1               5                   10                  15
Pro Phe Arg Thr Phe Ser Ala Ser Asp Trp Gly Leu Thr His Leu Val
                20                  25                  30
Val His Glu Gln Thr Gly Glu Val Tyr Val Gly Ala Val Asn Arg Ile
            35                  40                  45
Tyr Lys Leu Ser Gly Asn Leu Thr Leu Leu Arg Ala His Val Thr Gly
        50                  55                  60
Pro Val Glu Asp Asn Glu Lys Cys Tyr Pro Pro Pro Ser Val Gln Ser
65                  70                  75                  80
Cys Pro His Gly Leu Gly Ser Thr Asp Asn Val Asn Lys Leu Leu Leu
                85                  90                  95
Leu Asp Tyr Ala Ala Asn Arg Leu Leu Ala Cys Gly Ser Ala Ser Gln
                100                 105                 110
Gly Ile Cys Gln Phe Leu Arg Leu Asp Asp Leu Phe Lys Leu Gly Glu
            115                 120                 125
Pro His His Arg Lys Glu His Tyr Leu Ser Ser Val Gln Glu Ala Gly
        130                 135                 140
Ser Met Ala Gly Val Leu Ile Ala Gly Pro Pro Gly Gln Gly Gln Ala
145                 150                 155                 160
Lys Leu Phe Val Gly Thr Pro Ile Asp Gly Lys Ser Glu Tyr Phe Pro
                165                 170                 175
Thr Leu Ser Ser Arg Arg Leu Met Ala Asn Glu Glu Asp Ala Asp Met
                180                 185                 190
Phe Gly Phe Val Tyr Gln Asp Glu Phe Val Ser Ser Gln Leu Lys Ile
            195                 200                 205
Pro Ser Asp Thr Leu Ser Lys Phe Pro Ala Phe Asp Ile Tyr Tyr Val
        210                 215                 220
Tyr Ser Phe Arg Ser Glu Gln Phe Val Tyr Tyr Leu Thr Leu Gln Leu
225                 230                 235                 240
Asp Thr Gln Leu Thr Ser Pro Asp Ala Ala Gly Glu His Phe Phe Thr
                245                 250                 255
Ser Lys Ile Val Arg Leu Cys Val Asp Asp Pro Lys Phe Tyr Ser Tyr
                260                 265                 270
Val Glu Phe Pro Ile Gly Cys Glu Gln Ala Gly Val Glu Tyr Arg Leu
            275                 280                 285
Val Gln Asp Ala Tyr Leu Ser Arg Pro Gly Arg Ala Leu Ala His Gln
        290                 295                 300
Leu Gly Leu Ala Glu Asp Glu Asp Val Leu Phe Thr Val Phe Ala Gln
305                 310                 315                 320
Gly Gln Lys Asn Arg Val Lys Pro Pro Lys Glu Ser Ala Leu Cys Leu
                325                 330                 335
```

-continued

Phe Thr Leu Arg Ala Ile Lys Glu Lys Ile Lys Glu Arg Ile Gln Ser
                340                 345                 350

Cys Tyr Arg Gly Glu Gly Lys Leu Ser Leu Pro Trp Leu Leu Asn Lys
            355                 360                 365

Glu Leu Gly Cys Ile Asn Ser Pro Leu Gln Ile Asp Asp Asp Phe Cys
        370                 375                 380

Gly Gln Asp Phe Asn Gln Pro Leu Gly Gly Thr Val Thr Ile Glu Gly
385                 390                 395                 400

Thr Pro Leu Phe Val Asp Lys Asp Asp Gly Leu Thr Ala Val Ala Ala
                405                 410                 415

Tyr Asp Tyr Arg Gly Arg Thr Val Val Phe Ala Gly Thr Arg Ser Gly
            420                 425                 430

Arg Ile Arg Lys Ile Leu Val Asp Leu Ser Asn Pro Gly Gly Arg Pro
        435                 440                 445

Ala Leu Ala Tyr Glu Ser Val Val Ala Gln Glu Gly Ser Pro Ile Leu
450                 455                 460

Arg Asp Leu Val Leu Ser Pro Asn His Gln Tyr Leu Tyr Ala Met Thr
465                 470                 475                 480

Glu Lys Gln Val Thr Arg Val Pro Val Glu Ser Cys Val Gln Tyr Thr
                485                 490                 495

Ser Cys Glu Leu Cys Leu Gly Ser Arg Asp Pro His Cys Gly Trp Cys
            500                 505                 510

Val Leu His Ser Ile Cys Ser Arg Arg Asp Ala Cys Glu Arg Ala Asp
        515                 520                 525

Glu Pro Gln Arg Phe Ala Ala Asp Leu Leu Gln Cys Val Gln Leu Thr
530                 535                 540

Val Gln Pro Arg Asn Val Ser Val Thr Met Ser Gln Val Pro Leu Val
545                 550                 555                 560

Leu Gln Ala Trp Asn Val Pro Asp Leu Ser Ala Gly Val Asn Cys Ser
                565                 570                 575

Phe Glu Asp Phe Thr Glu Ser Glu Ser Val Leu Glu Asp Gly Arg Ile
            580                 585                 590

His Cys Arg Ser Pro Ser Ala Arg Glu Val Ala Pro Ile Thr Arg Gly
        595                 600                 605

Gln Gly Asp Gln Arg Val Val Lys Leu Tyr Leu Lys Ser Lys Glu Thr
610                 615                 620

Gly Lys Lys Phe Ala Ser Val Asp Phe Val Phe Tyr Asn Cys Ser Val
625                 630                 635                 640

His Gln Ser Cys Leu Ser Cys Val Asn Gly Ser Phe Pro Cys His Trp
                645                 650                 655

Cys Lys Tyr Arg His Val Cys Thr His Asn Val Ala Asp Cys Ala Phe
            660                 665                 670

Leu Glu Gly Arg Val Asn Val Ser Glu Asp Cys Pro Gln Ile Leu Pro
        675                 680                 685

Ser Thr Gln Ile Tyr Val Pro Val Gly Val Val Lys Pro Ile Thr Leu
690                 695                 700

Ala Ala Arg Asn Leu Pro Gln Pro Gln Ser Gly Gln Arg Gly Tyr Glu
705                 710                 715                 720

Cys Leu Phe His Ile Pro Gly Ser Pro Ala Arg Val Thr Ala Leu Arg
                725                 730                 735

Phe Asn Ser Ser Ser Leu Gln Cys Gln Asn Ser Ser Tyr Ser Tyr Glu
            740                 745                 750

Gly Asn Asp Val Ser Asp Leu Pro Val Asn Leu Ser Val Val Trp Asn

```
                    755                 760                 765
Gly Asn Phe Val Ile Asp Asn Pro Gln Asn Ile Gln Ala His Leu Tyr
    770                 775                 780
Lys Cys Pro Ala Leu Arg Glu Ser Cys Gly Leu Cys Leu Lys Ala Asp
785                 790                 795                 800
Pro Arg Phe Glu Cys Gly Trp Cys Val Ala Glu Arg Cys Ser Leu
                    805                 810                 815
Arg His His Cys Ala Ala Asp Thr Pro Ala Ser Trp Met His Ala Arg
                    820                 825                 830
His Gly Ser Ser Arg Cys Thr Asp Pro Lys Ile Leu Lys Leu Ser Pro
                    835                 840                 845
Glu Thr Gly Pro Arg Gln Gly Gly Thr Arg Leu Thr Ile Thr Gly Glu
                    850                 855                 860
Asn Leu Gly Leu Arg Phe Glu Asp Val Arg Leu Gly Val Arg Val Gly
865                 870                 875                 880
Lys Val Leu Cys Ser Pro Val Glu Ser Glu Tyr Ile Ser Ala Glu Gln
                    885                 890                 895
Ile Val Cys Glu Ile Gly Asp Ala Ser Ser Val Arg Ala His Asp Ala
                    900                 905                 910
Leu Val Glu Val Cys Val Arg Asp Cys Ser Pro His Tyr Arg Ala Leu
                    915                 920                 925
Ser Pro Lys Arg Phe Thr Phe Val Thr Pro Thr Phe Tyr Arg Val Ser
                    930                 935                 940
Pro Ser Arg Gly Pro Leu Ser Gly Gly Thr Trp Ile Gly Ile Glu Gly
945                 950                 955                 960
Ser His Leu Asn Ala Gly Ser Asp Val Ala Val Ser Val Gly Gly Arg
                    965                 970                 975
Pro Cys Ser Phe Ser Trp Arg Asn Ser Arg Glu Ile Arg Cys Leu Thr
                    980                 985                 990
Pro Pro Gly Gln Ser Pro Gly Ser Ala Pro Ile Ile Ile Asn Ile Asn
                    995                 1000                1005
Arg Ala Gln Leu Thr Asn Pro Glu Val Lys Tyr Asn Tyr Thr Glu
                1010                1015                1020
Asp Pro Thr Ile Leu Arg Ile Asp Pro Glu Trp Ser Ile Asn Ser
                1025                1030                1035
Gly Gly Thr Leu Leu Thr Val Thr Gly Thr Asn Leu Ala Thr Val
                1040                1045                1050
Arg Glu Pro Arg Ile Arg Ala Lys Tyr Gly Gly Ile Glu Arg Glu
                1055                1060                1065
Asn Gly Cys Leu Val Tyr Asn Asp Thr Thr Met Val Cys Arg Ala
                1070                1075                1080
Pro Ser Val Ala Asn Pro Val Arg Ser Pro Pro Glu Leu Gly Glu
                1085                1090                1095
Arg Pro Asp Glu Leu Gly Phe Val Met Asp Asn Val Arg Ser Leu
                1100                1105                1110
Leu Val Leu Asn Ser Thr Ser Phe Leu Tyr Tyr Pro Asp Pro Val
                1115                1120                1125
Leu Glu Pro Leu Ser Pro Thr Gly Leu Leu Glu Leu Lys Pro Ser
                1130                1135                1140
Ser Pro Leu Ile Leu Lys Gly Arg Asn Leu Leu Pro Pro Ala Pro
                1145                1150                1155
Gly Asn Ser Arg Leu Asn Tyr Thr Val Leu Ile Gly Ser Thr Pro
                1160                1165                1170
```

-continued

Cys Thr Leu Thr Val Ser Glu Thr Gln Leu Leu Cys Glu Ala Pro
1175                1180               1185

Asn Leu Thr Gly Gln His Lys Val Thr Val Arg Ala Gly Gly Phe
1190                1195               1200

Glu Phe Ser Pro Gly Thr Leu Gln Val Tyr Ser Asp Ser Leu Leu
1205                1210               1215

Thr Leu Pro Ala Ile Val Gly Ile Gly Gly Gly Gly Leu Leu
1220                1225               1230

Leu Leu Val Ile Val Ala Val Leu Ile Ala Tyr Lys Arg Lys Ser
1235                1240               1245

Arg Asp Ala Asp Arg Thr Leu Lys Arg Leu Gln Leu Gln Met Asp
1250                1255               1260

Asn Leu Glu Ser Arg Val Ala Leu Glu Cys Lys Glu Ala Phe Ala
1265                1270               1275

Glu Leu Gln Thr Asp Ile His Glu Leu Thr Asn Asp Leu Asp Gly
1280                1285               1290

Ala Gly Ile Pro Phe Leu Asp Tyr Arg Thr Tyr Ala Met Arg Val
1295                1300               1305

Leu Phe Pro Gly Ile Glu Asp His Pro Val Leu Lys Glu Met Glu
1310                1315               1320

Val Gln Ala Asn Val Glu Lys Ser Leu Thr Leu Phe Gly Gln Leu
1325                1330               1335

Leu Thr Lys Lys His Phe Leu Leu Thr Phe Ile Arg Thr Leu Glu
1340                1345               1350

Ala Gln Arg Ser Phe Ser Met Arg Asp Arg Gly Asn Val Ala Ser
1355                1360               1365

Leu Ile Met Thr Ala Leu Gln Gly Glu Met Glu Tyr Ala Thr Gly
1370                1375               1380

Val Leu Lys Gln Leu Leu Ser Asp Leu Ile Glu Lys Asn Leu Glu
1385                1390               1395

Ser Lys Asn His Pro Lys Leu Leu Leu Arg Arg Thr Glu Ser Val
1400                1405               1410

Ala Glu Lys Met Leu Thr Asn Trp Phe Thr Phe Leu Leu Tyr Lys
1415                1420               1425

Phe Leu Lys Glu Cys Ala Gly Glu Pro Leu Phe Met Leu Tyr Cys
1430                1435               1440

Ala Ile Lys Gln Gln Met Glu Lys Gly Pro Ile Asp Ala Ile Thr
1445                1450               1455

Gly Glu Ala Arg Tyr Ser Leu Ser Glu Asp Lys Leu Ile Arg Gln
1460                1465               1470

Gln Ile Asp Tyr Lys Thr Leu Thr Leu Asn Cys Val Asn Pro Glu
1475                1480               1485

Asn Glu Asn Ala Pro Glu Val Pro Val Lys Gly Leu Asp Cys Asp
1490                1495               1500

Thr Val Thr Gln Ala Lys Glu Lys Leu Leu Asp Ala Ala Tyr Lys
1505                1510               1515

Gly Val Pro Tyr Ser Gln Arg Pro Lys Ala Ala Asp Met Asp Leu
1520                1525               1530

Glu Trp Arg Gln Gly Arg Met Ala Arg Ile Ile Leu Gln Asp Glu
1535                1540               1545

Asp Val Thr Thr Lys Ile Asp Asn Asp Trp Lys Arg Leu Asn Thr
1550                1555               1560

| | | | | | | | | | | | |
|---|---|---|---|---|---|---|---|---|---|---|---|
|Leu|Ala|His|Tyr|Gln|Val|Thr|Asp|Gly|Ser|Ser|Val|Ala|Leu|Val|
|1565| | | | |1570| | | |1575| | |

Pro Lys Gln Thr Ser Ala Tyr Asn Ile Ser Asn Ser Ser Thr Phe
    1580                1585                1590

Thr Lys Ser Leu Ser Arg Tyr Glu Ser Met Leu Arg Thr Ala Ser
1595                1600                1605

Ser Pro Asp Ser Leu Arg Ser Arg Thr Pro Met Ile Thr Pro Asp
    1610                1615                1620

Leu Glu Ser Gly Thr Lys Leu Trp His Leu Val Lys Asn His Asp
1625                1630                1635

His Leu Asp Gln Arg Glu Gly Asp Arg Gly Ser Lys Met Val Ser
    1640                1645                1650

Glu Ile Tyr Leu Thr Arg Leu Leu Ala Thr Lys Gly Thr Leu Gln
1655                1660                1665

Lys Phe Val Asp Asp Leu Phe Glu Thr Ile Phe Ser Thr Ala His
    1670                1675                1680

Arg Gly Ser Ala Leu Pro Leu Ala Ile Lys Tyr Met Phe Asp Phe
1685                1690                1695

Leu Asp Glu Gln Ala Asp Lys His Gln Ile His Asp Ala Asp Val
    1700                1705                1710

Arg His Thr Trp Lys Ser Asn Cys Leu Pro Leu Arg Phe Trp Val
1715                1720                1725

Asn Val Ile Lys Asn Pro Gln Phe Val Phe Asp Ile His Lys Asn
    1730                1735                1740

Ser Ile Thr Asp Ala Cys Leu Ser Val Val Ala Gln Thr Phe Met
1745                1750                1755

Asp Ser Cys Ser Thr Ser Glu His Lys Leu Gly Lys Asp Ser Pro
    1760                1765                1770

Ser Asn Lys Leu Leu Tyr Ala Lys Asp Ile Pro Asn Tyr Lys Ser
1775                1780                1785

Trp Val Glu Arg Tyr Tyr Ala Asp Ile Ala Lys Met Pro Ala Ile
    1790                1795                1800

Ser Asp Gln Asp Met Ser Ala Tyr Leu Ala Glu Gln Ser Arg Leu
1805                1810                1815

His Leu Ser Gln Phe Asn Ser Met Ser Ala Leu His Glu Ile Tyr
    1820                1825                1830

Ser Tyr Ile Thr Lys Tyr Lys Asp Glu Ile Leu Ala Ala Leu Glu
1835                1840                1845

Lys Asp Glu Gln Ala Arg Arg Gln Arg Leu Arg Ser Lys Leu Glu
    1850                1855                1860

Gln Val Val Asp Thr Met Ala Leu Ser Ser
1865                1870

<210> SEQ ID NO 4
<211> LENGTH: 2316
<212> TYPE: DNA
<213> ORGANISM: Homo sapiens

<400> SEQUENCE: 4
atgggctggt taactaggat tgtctgtctt ttctggggag tattacttac agcaagagca      60
aactatcaga atgggaagaa caatgtgcca aggctgaaat atcctacaa agaaatgttg     120 gaatccaaca atgtgatcac tttcaatggc ttggccaaca gctccagtta tcataccttc     180
cttttggatg aggaacggag taggctgtat gttggagcaa aggatcacat attttcattc     240

```
gacctggtta atatcaagga ttttcaaaag attgtgtggc cagtatctta caccagaaga      300
gatgaatgca agtgggctgg aaaagacatc ctgaaagaat gtgctaattt catcaaggta      360
cttaaggcat ataatcagac tcacttgtac gcctgtggaa cgggggcttt tcatccaatt      420
tgcacctaca ttgaaattgg acatcatcct gaggacaata ttttttaagct ggagaactca      480 cattttgaaa acggccgtgg gaagagtcca tatgaccctc agctgctgac agcatccctt      540
ttaatagatg gagaattata ctctggaact gcagctgatt ttatggggcg agactttgct      600
atcttccgaa ctcttgggca ccaccaccca atcaggacag agcagcatga ttccaggtgg      660
ctcaatgatc caaagttcat tagtgcccac ctcatctcag agagtgacaa tcctgaagat      720
gacaaagtat acttttttctt ccgtgaaaat gcaatagatg gagaacactc tggaaaagct      780
actcacgcta aataggtca gatatgcaag aatgactttg gagggcacag aagtctggtg      840
aataaatgga caacattcct caaagctcgt ctgatttgct cagtgccagg tccaaatggc      900
attgacactc attttgatga actgcaggat gtattcctaa tgaactttaa agatcctaaa      960
aatccagttg tatatggagt gtttacgact tccagtaaca ttttcaaggg atcagccgtg     1020
tgtatgtata gcatgagtga tgtgagaagg tgttccttg gtccatatgc ccacagggat     1080
ggacccaact atcaatgggt gccttatcaa ggaagagtcc cctatccacg ccaggaact     1140 tgtcccagca aaacatttgg tggttttgac tctacaaagg accttcctga tgatgttata     1200
acctttgcaa gaagtcatcc agccatgtac aatccagtgt ttcctatgaa caatcgccca     1260
atagtgatca aaacggatgt aaattatcaa tttacacaaa ttgtcgtaga ccgagtggat     1320
gcagaagatg gacagtatga tgttatgttt atcggaacag atgttgggac cgttcttaaa     1380
gtagtttcaa ttcctaagga gacttggtat gatttagaag aggttctgct ggaagaaatg     1440
acagtttttc gggaaccgac tgctatttca gcaatggagc tttccactaa gcagcaacaa     1500
ctatatattg gttcaacggc tggggttgcc cagctccctt tacaccggtg tgatatttac     1560
gggaaagcgt gtgctgagtg ttgcctcgcc cgagacctt actgtgcttg ggatggttct     1620
gcatgttctc gctattttcc cactgcaaag agacgcacaa gacgacaaga tataagaaat     1680
ggagacccac tgactcactg ttcagactta accatgata atcaccatgg ccacagccct     1740
gaagagagaa tcatctatgg tgtagagaat agtagcacat ttttggaatg cagtccgaag     1800
tcgcagagag cgctggtcta ttggcaattc cagaggcgaa atgaagagcg aaaagaagag     1860
atcagagtgg atgatcatat catcaggaca gatcaaggcc ttctgctacg tagtctacaa     1920
cagaaggatt caggcaatta cctctgccat gcggtggaac atgggttcat acaaactctt     1980
cttaaggtaa ccctggaagt cattgacaca gagcatttgg aagaacttct tcataaagat     2040
gatgatggag atggctctaa gaccaaagaa atgtccaata gcatgacacc tagccagaag     2100
gtctggtaca gagacttcat gcagctcatc aaccaccca atctcaacac aatggatgag     2160
ttctgtgaac aagtttggaa aagggaccga aaacaacgtc ggcaaaggcc aggacatacc     2220
ccagggaaca gtaacaaatg gaagcactta caagaaaata agaaaggtag aaacaggagg     2280
acccacgaat ttgagagggc acccaggagt gtctga                              2316
```

<210> SEQ ID NO 5
<211> LENGTH: 2772
<212> TYPE: DNA
<213> ORGANISM: Homo sapiens

<400> SEQUENCE: 5

```
atggagaggg ggctgccgct cctctgcgcc gtgctcgccc tcgtcctcgc cccggccggc       60
```

```
gcttttcgca acgataaatg tggcgatact ataaaaattg aaagcccggg gtaccttaca      120
tctcctggtt atcctcattc ttatcaccca agtgaaaaat gcgaatggct gattcaggct      180
ccggacccat accagagaat tatgatcaac ttcaaccctc acttcgattt ggaggacaga      240
gactgcaagt atgactacgt ggaagtcttc gatggagaaa atgaaaatgg acattttagg      300
ggaaagttct gtggaaagat agcccctcct cctgttgtgt cttcagggcc atttcttttt      360
atcaaatttg tctctgacta cgaaacacat ggtgcaggat tttccatacg ttatgaaatt      420
ttcaagagag gtcctgaatg ttcccagaac tacacaacac ctagtggagt gataaagtcc      480 cccgattcc ctgaaaaata tcccaacagc cttgaatgca cttatattgt ctttgcgcca      540
aagatgtcag agattatcct ggaatttgaa agctttgacc tggagcctga ctcaaatcct      600
ccagggggga tgttctgtcg ctacgaccgg ctagaaatct gggatggatt ccctgatgtt      660
ggccctcaca ttgggcgtta ctgtggacag aaaacaccag gtcgaatccg atcctcatcg      720
ggcattctct ccatggtttt ttacaccgac agcgcgatag caaaagaagg tttctcagca      780
aactacagtg tcttgcagag cagtgtctca gaagatttca atgtatggaa agctctgggc      840
atggaatcag gagaaattca ttctgaccag atcacagctt cttcccagta tagcaccaac      900
tggtctgcag agcgctcccg cctgaactac cctgagaatg ggtggactcc cggagaggat      960
tcctaccgag agtggataca ggtagacttg ggccttctgc gctttgtcac ggctgtcggg     1020
acacagggcg ccatttcaaa agaaaccaag aagaaatatt atgtcaagac ttacaagatc     1080
gacgttagct ccaacgggga agactggatc accataaaag aaggaaacaa acctgttctc     1140
tttcagggaa acaccaaccc cacagatgtt gtggttgcag tattccccaa accactgata     1200
actcgatttg tccgaatcaa gcctgcaact tgggaaactg gcatatctat gagatttgaa     1260
gtatacggtt gcaagataac agattatcct tgctctggaa tgttgggtat ggtgtctgga     1320
cttatttctg actcccagat cacatcatcc aaccaagggg acagaaactg gatgcctgaa     1380
aacatccgcc tggtaaccag tcgctctggc tgggcacttc cacccgcacc tcattcctac     1440
atcaatgagt ggctccaaat agacctgggg gaggagaaga tcgtgagggg catcatcatt     1500
cagggtggga agcaccgaga gaacaaggtg ttcatgagga agttcaagat cgggtacagc     1560
aacaacggct cggactggaa gatgatcatg gatgacagca aacgcaaggc gaagtctttt     1620
gagggcaaca caactatga tacacctgag ctgcggactt ttccagctct ctccacgcga     1680
ttcatcagga tctaccccga gagagccact catggcggac tggggctcag aatggagctg     1740
ctgggctgtg aagtggaagc ccctacagct ggaccgacca ctcccaacgg gaacttggtg     1800
gatgaatgtg atgacgacca ggccaactgc cacagtggaa caggtgatga cttccagctc     1860
acaggtggca ccactgtgct ggccacagaa aagcccacgg tcatagacag caccatacaa     1920
tcagagtttc aacatatgg ttttaactgt gaatttggct ggggctctca caagaccttc     1980
tgccactggg aacatgacaa tcacgtgcag ctcaagtgga gtgtgttgac cagcaagacg     2040
ggacccattc aggatcacac aggagatggc aacttcatct attcccaagc tgacgaaaat     2100
cagaagggca agtggctcg cctggtgagc cctgtggttt attcccagaa ctctgcccac     2160
tgcatgacct tctggtatca catgtctggg tcccacgtcg gcacactcag ggtcaaactg     2220
cgctaccaga agccagagga gtacgatcag ctggtctgga tggccattgg acaccaaggt     2280
gaccactgga aggaagggcg tgtcttgctc cacaagtctc tgaaacttta tcaggtgatt     2340
ttcgagggcg aaatcggaaa aggaaacctt ggtgggattg ctgtggatga cattagtatt     2400
```

| | |
|---|---:|
| aataaccaca tttcacaaga agattgtgca aaaccagcag acctggataa aaagaaccca | 2460 |
| gaaattaaaa ttgatgaaac agggagcacg ccaggatacg aaggtgaagg agaaggtgac | 2520 |
| aagaacatct ccaggaagcc aggcaatgtg ttgaagacct tagaccccat cctcatcacc | 2580 |
| atcatagcca tgagtgccct gggggtcctc ctggggctg tctgtgggt cgtgctgtac | 2640 |
| tgtgcctgtt ggcataatgg gatgtcagaa agaaacttgt ctgccctgga gaactataac | 2700 |
| tttgaacttg tggatggtgt gaagttgaaa aaagacaaac tgaatacaca gagtacttat | 2760 |
| tcggaggcat ga | 2772 |

<210> SEQ ID NO 6
<211> LENGTH: 5622
<212> TYPE: DNA
<213> ORGANISM: Homo sapiens

<400> SEQUENCE: 6

| | |
|---|---:|
| atgtgggctg aggcaggctt gcccagggca ggcgggggtt cacagccccc cttccgcacc | 60 |
| ttctcggcca gcgactgggg cctcacccac ctagtggtgc atgagcagac aggcgaggtg | 120 |
| tatgtgggcg cagtgaaccg catctataag ctgtcgggga acctgacact gctgcgggcc | 180 |
| cacgtcacgg gccctgtgga ggacaacgag aagtgctacc cgccgcccag cgtgcagtcc | 240 |
| tgcccccacg gcctgggcag tactgacaac gtcaacaagc tgctgctgct ggactatgcc | 300 |
| gctaaccgcc tgctggcctg tggcagcgcc tcccagggca tctgccagtt cctgcgtctg | 360 |
| gacgatctct tcaaactggg tgagccacac accgtaagg agcactacct gtccagcgtg | 420 |
| caggaggcag gcagcatggc gggcgtgctc attgccgggc accgggcca gggccaggcc | 480 |
| aagctcttcg tgggcacacc catcgatggc aagtccgagt acttccccac actgtccagc | 540 |
| cgtcggctca tggccaacga ggaggatgcc gacatgttcg gcttcgtgta ccaggatgag | 600 |
| tttgtgtcat cacagctcaa gatcccttcg gacacgctgt ccaagttccc ggcctttgac | 660 |
| atctactatg tgtacagctt ccgcagcgag cagtttgtct actacctcac gctgcagcta | 720 |
| gacacacagc tgacctcgcc tgatgccgcc ggcgagcact tcttcacgtc caagatcgtg | 780 |
| cggctctgtg tggacgaccc caaattctac tcgtacgttg agttcccat ggctgcgag | 840 |
| caggcgggtg tggagtaccg cctggtgcag gatgcctacc tgagccggcc cggccgtgcc | 900 |
| ctggcccacc agctgggcct ggctgaggac gaggacgtgc tgttcactgt gttcgcccag | 960 |
| ggccagaaga accgcgtgaa gccaccaaag gagtcagcac tgtgcctgtt cacgctcagg | 1020 |
| gccatcaagg agaagattaa ggagcgcatc cagtcctgct accgtggtga gggcaagctc | 1080 |
| tccctgccgt ggctgctcaa caaggagctg ggctgcatca actcgcccct gcagatcgat | 1140 |
| gacgacttct gcgggcagga cttcaaccag cccctggggg gcacagtcac cattgagggg | 1200 |
| acgcccctgt tcgtggacaa ggatgatggc ctgaccgccg tggctgccta tgactatcgg | 1260 |
| ggccgcactg tggtattcgc cggcacgcga agtggccgca tccgcaagat cctggtggac | 1320 |
| ctctcaaacc ccgtggccg gcctgccctg gcctacgaga gcgtcgtggc ccaggagggc | 1380 |
| agccccatcc tgcgagacct cgtcctcagc cccaaccacc agtacctcta cgccatgacc | 1440 |
| gagaagcagg tgacgcgggt gcctgtggag agctgtgtgc agtacacgtc ctgtgagctg | 1500 |
| tgtctgggt cacgggaccc ccactgtggc tggtgtgtcc tgcacagcat ctgctcgcgg | 1560 |
| cgggacgcct gtgagcgagc agacgagccc cagcgctttg ctgcggacct gctgcagtgt | 1620 |
| gtgcagctga ctgtgcagcc ccgcaatgtg tctgtcacca gtcccagtt cccacttgtg | 1680 |
| ctgcaggcct ggaacgtgcc tgacctctca gctggcgtca actgctcctt cgaggacttc | 1740 |

```
acggaatctg agagcgtcct ggaggatggc cggatccact gccgctcacc ctccgcccgg    1800
gaggtggcgc ccatcacgcg gggccaggga gaccagcggg tggtgaaact ctacctaaag    1860
tccaaggaga cagggaagaa gtttgcgtct gtggacttcg tcttctacaa ctgcagcgtc    1920
caccagtcct gcctgtcctg tgtcaacggc tcctttccct gccactggtg caaataccgc    1980
cacgtgtgca cacacaacgt ggctgactgc gccttcctgg agggccgtgt caacgtgtct    2040
gaggactgcc cacagatcct gccctccacg cagatctacg tgccagtggg agtggtaaaa    2100
cccatcaccc tggccgcacg gaacctgcca cagccacagt caggccagcg tggatatgag    2160
tgcctcttcc acatcccggg cagcccggcc cgtgtcaccg ccctgcgctt caacagctcc    2220
agcctgcagt gccagaattc ctcgtactcc tacgagggga acgatgtcag cgacctgcca    2280
gtgaacctgt cagtcgtgtg aacggcaac tttgtcattg acaacccaca gaacatccag    2340
gcgcacctct acaagtgccc ggccctgcgc gagagctgcg gcctctgcct caaggccgac    2400
ccgcgcttcg agtgcggatg tgcgtggcc gagcgccgct gctccctgcg acaccactgc    2460
gctgccgaca cacctgcatc gtggatgcac gcgcgtcacg gcagcagtcg ctgcaccgac    2520
cccaagatcc tcaagctgtc ccccgagacg ggcccgaggc agggcggcac gcggctcact    2580
atcacaggcg agaacctggg cctgcgattc gaagacgtgc gtctgggcgt gcgcgtgggc    2640
aaggtgctgt gcagccctgt ggagagcgag tacatcagtg cggagcagat cgtctgtgag    2700
atcggggacg ccagctccgt gcgtgcccat gacgccctgg tggaggtgtg tgtgcgggac    2760
tgctcaccac actaccgcgc cctgtcaccc aagcgcttca ccttcgtgac accaaccttc    2820
taccgtgtga gccctcccg tgggcctctg tcaggggca cctggattgg catcgaggga    2880
agccacctga acgcaggcag tgatgtggct gtgtcggtcg gtggccggcc ctgctccttc    2940
tcctggagga actcccgtga gatccggtgc ctgacacccc ccgggcagag ccctggcagc    3000
gctcccatca tcatcaacat caaccgcgcc cagctcacca accctgaggt gaagtacaac    3060
tacaccgagg accccaccat cctgaggatc gaccccgagt ggagcatcaa cagcggtggg    3120
accctcctga cggtcacagg caccaacctg ccactgtcc gtgaacccg aatccgggcc    3180 aagtatggag gcattgagag ggagaacggc tgcctggtgt acaatgacac caccatggta    3240
tgccgcgccc cgtctgtggc caaccctgtg cgcagcccac cagagctggg ggagcggccg    3300
gatgagctgg gcttcgtcat ggacaacgtg cgctccctgc ttgtgctcaa ctccaccctcc    3360 ttcctctact accctgaccc cgtactggag ccactcagcc ccactggcct gctggagctg    3420
aagcccagct ccccactcat cctcaagggc cggaacctct tgccacctgc acccggcaac    3480
tcccgactca actacacggt gctcatcggc tccacaccct gtaccctcac cgtgtcggag    3540
acgcaactgc tgtgcgaggc gcccaacctc actgggcagc acaaggtcac ggtgcgggca    3600
ggtggcttcg agttctcgcc agggacactg caggtgtact cggacagcct gctgacgctg    3660
cctgccattg tgggcattgg cggaggcggg ggtctcctgc tgctggtcat cgtggctgtg    3720
ctcatcgcct acaagcgcaa gtcacgagat gctgaccgca cactcaagcg gctgcagctc    3780
cagatggaca acctggagtc ccgcgtggcc ctcgaatgca aggaagcctt tgcagagctg    3840
cagacagaca tccacgagct gaccaatgac ctggacggtg ccggcatccc cttccttgac    3900
taccggacat atgccatgcg ggtgctcttt cctgggatcg aggaccaccc tgtgctcaag    3960
gagatggagg tgcaggccaa tgtggagaag tcgctgacac tgttcgggca gctgctgacc    4020
aagaagcact tcctgctgac cttcatccgc acgctggagg cacagcgcag cttctccatg    4080
```

```
cgcgaccgcg ggaatgtggc ctcgctcatc atgacggccc tgcagggcga gatggaatac      4140
gccacaggcg tgctcaagca gctgctttcc gacctcatcg agaagaacct ggagagcaag      4200
aaccacccca agctgctact gcgccggact gagtcggtgg cagagaagat gctaactaac      4260
tggttcacct tcctcttgta taagttcctc aaggagtgcg ctggggagcc gctgttcatg      4320
ctgtactgcg ccatcaagca gcagatggag aagggcccca ttgacgccat cacgggtgag      4380
gcacgctact ccctgagtga ggacaagctc atccggcagc agattgacta caagacactg      4440
accctgaact gtgtgaaccc tgagaatgag aatgcacctg aggtgccggt gaaggggctg      4500
gactgtgaca cggtcaccca ggccaaggag aagctgctgg acgctgccta aagggcgtg       4560 ccctactccc agcggcccaa ggccgcggac atggacctgg agtggcgcca gggccgcatg      4620
gcgcgcatca tcctgcagga cgaggacgtc accaccaaga ttgacaacga ttggaagagg      4680
ctgaacacac tggctcacta ccaggtgaca gacgggtcct cggtggcact ggtgcccaag      4740
cagacgtccg cctacaacat ctccaactcc tccaccttca ccaagtccct cagcagatac      4800
gagagcatgc tgcgcacggc cagcagcccc gacagcctgc gctcgcgcac gcccatgatc      4860
acgcccgacc tggagagcgg caccaagctg tggcacctgg tgaagaacca cgaccacctg      4920
gaccagcgtg agggtgaccg cggcagcaag atggtctcgg agatctactt gacacggcta      4980
ctggccacca agggcacact gcagaagttt gtggacgacc tgtttgagac catcttcagc      5040
acggcacacc ggggctcagc cctgccgctg ccatcaagt acatgttcga cttcctggat      5100
gagcaggccg acaagcacca gatccacgat gctgacgtgc ccacacctg gaagagcaac      5160 tgcctgcccc tgcgcttctg ggtgaacgtg atcaagaacc acagtttgt gttcgacatt      5220 cacaagaaca gcatcacgga cgcctgcttg tcggtggtgg cccagacctt catggactcc      5280
tgctccacct ctgagcacaa gctgggcaag gactcaccct ccaacaagct gctctacgcc      5340
aaggacatcc ccaactacaa gagctgggtg gagaggtact atgcagacat cgccaagatg      5400
ccagccatca gcgaccagga catgagtgcg tatctggctg agcagtcccg cctgcacctg      5460
agccagttca acagcatgag cgccttgcac gagatctact cctacatcac caagtacaag      5520
gatgagatcc tggcagccct ggagaaggat gagcaggcgc ggcggcagcg gctgcggagc      5580
aagctggagc aggtggtgga cacgatggcc ctgagcagct ga                       5622
```

<210> SEQ ID NO 7  
<211> LENGTH: 223  
<212> TYPE: PRT  
<213> ORGANISM: Homo sapiens

<400> SEQUENCE: 7

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
```

```
                100             105             110
Ser Lys Ala Lys Gly Gln Pro Arg Glu Pro Gln Val Tyr Thr Leu Pro
            115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Pro Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
195                 200                 205

His Asn His Tyr Thr Gln Lys Ser Leu Ser Leu Ser Pro Gly Lys
            210                 215                 220

<210> SEQ ID NO 8
<211> LENGTH: 221
<212> TYPE: PRT
<213> ORGANISM: Homo sapiens

<400> SEQUENCE: 8

Cys Pro Pro Cys Pro Ala Pro Pro Val Ala Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser His Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Phe Arg Val Val Ser Val Leu
65                  70                  75                  80

Thr Val Val His Gln Asp Trp Leu Asn Gly Lys Glu Tyr Lys Cys Lys
                85                  90                  95

Val Ser Asn Lys Gly Leu Pro Ala Pro Ile Glu Lys Thr Ile Ser Lys
            100                 105                 110

Thr Lys Gly Gln Pro Arg Glu Pro Gln Val Tyr Thr Leu Pro Pro Ser
        115                 120                 125

Arg Glu Glu Met Thr Lys Asn Gln Val Ser Leu Thr Cys Leu Val Lys
    130                 135                 140

Gly Phe Tyr Pro Ser Asp Ile Ser Val Glu Trp Glu Ser Asn Gly Gln
145                 150                 155                 160

Pro Glu Asn Asn Tyr Lys Thr Thr Pro Pro Met Leu Asp Ser Asp Gly
                165                 170                 175

Ser Phe Phe Leu Tyr Ser Lys Leu Thr Val Asp Lys Ser Arg Trp Gln
            180                 185                 190

Gln Gly Asn Val Phe Ser Cys Ser Val Met His Glu Ala Leu His Asn
        195                 200                 205

His Tyr Thr Gln Lys Ser Leu Ser Leu Ser Pro Gly Lys
    210                 215                 220

<210> SEQ ID NO 9
<211> LENGTH: 222
<212> TYPE: PRT
<213> ORGANISM: Homo sapiens
```

<400> SEQUENCE: 9

Cys Pro Arg Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Gln Phe Lys Trp Tyr Val Asp Gly Val Glu Val His Asn Ala Lys Thr
    50                  55                  60

Lys Pro Arg Glu Glu Gln Tyr Asn Ser Thr Phe Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Thr Lys Gly Gln Pro Arg Glu Pro Gln Val Tyr Thr Leu Pro Pro
        115                 120                 125

Ser Arg Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Ser Gly
145                 150                 155                 160

Gln Pro Glu Asn Asn Tyr Asn Thr Thr Pro Pro Met Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Ile Phe Ser Cys Ser Val Met His Glu Ala Leu His
        195                 200                 205

Asn Arg Phe Thr Gln Lys Ser Leu Ser Leu Ser Pro Gly Lys
    210                 215                 220

<210> SEQ ID NO 10
<211> LENGTH: 222
<212> TYPE: PRT
<213> ORGANISM: Homo sapiens

<400> SEQUENCE: 10

Cys Pro Ser Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
    130                 135                 140

```
Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Lys
    210                 215                 220

<210> SEQ ID NO 11
<211> LENGTH: 923
<212> TYPE: PRT
<213> ORGANISM: Mus musculus

<400> SEQUENCE: 11

Met Glu Arg Gly Leu Pro Leu Leu Cys Ala Thr Leu Ala Leu Ala Leu
1               5                   10                  15

Ala Leu Ala Gly Ala Phe Arg Ser Asp Lys Cys Gly Gly Thr Ile Lys
            20                  25                  30

Ile Glu Asn Pro Gly Tyr Leu Thr Ser Pro Gly Tyr Pro His Ser Tyr
        35                  40                  45

His Pro Ser Glu Lys Cys Glu Trp Leu Ile Gln Ala Pro Glu Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Ile Asp Gly Glu Asn Glu Gly
                85                  90                  95

Gly Arg Leu Trp Gly Lys Phe Cys Gly Lys Ile Ala Pro Ser Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Ala Pro Thr Gly Val Ile Lys Ser
145                 150                 155                 160

Pro Gly Phe Pro Glu Lys Tyr Pro Asn Ser Leu Glu Cys Thr Tyr Ile
                165                 170                 175

Ile Phe Ala Pro Lys Met Ser Glu Ile Ile Leu Glu Phe Glu Ser Phe
            180                 185                 190

Asp Leu Glu Gln Asp Ser Asn Pro Pro Gly Gly Met Phe Cys Arg Tyr
        195                 200                 205

Asp Arg Leu Glu Ile Trp Asp Gly Phe Pro Glu Val Gly Pro His Ile
    210                 215                 220

Gly Arg Tyr Cys Gly Gln Lys Thr Pro Gly Arg Ile Arg Ser Ser Ser
225                 230                 235                 240

Gly Val Leu Ser Met Val Phe Tyr Thr Asp Ser Ala Ile Ala Lys Glu
                245                 250                 255

Gly Phe Ser Ala Asn Tyr Ser Val Leu Gln Ser Ser Ile Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Gly Thr Asn Trp Ser Val Glu
    290                 295                 300
```

-continued

```
Arg Ser Arg Leu Asn Tyr Pro Glu Asn Gly Trp Thr Pro Gly Glu Asp
305                 310                 315                 320

Ser Tyr Lys Glu Trp Ile Gln Val Asp Leu Gly Leu Leu Arg Phe Val
            325                 330                 335

Thr Ala Val Gly Thr Gln Gly Ala Ile Ser Lys Glu Thr Lys Lys Lys
        340                 345                 350

Tyr Tyr Val Lys Thr Tyr Arg Val Asp Ile Ser Ser Asn Gly Glu Asp
                355                 360                 365

Trp Ile Ser Leu Lys Glu Gly Asn Lys Ala Ile Ile Phe Gln Gly Asn
370                 375                 380

Thr Asn Pro Thr Asp Val Val Leu Gly Val Phe Ser Lys Pro Leu Ile
385                 390                 395                 400

Thr Arg Phe Val Arg Ile Lys Pro Val Ser Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
        435                 440                 445

Ala Ser Asn Gln Ala Asp Arg Asn Trp Met Pro Glu Asn Ile Arg Leu
    450                 455                 460

Val Thr Ser Arg Thr Gly Trp Ala Leu Pro Pro Ser Pro His Pro Tyr
465                 470                 475                 480

Thr Asn Glu Trp Leu Gln Val Asp Leu Gly Asp Glu Lys Ile Val Arg
                485                 490                 495

Gly Val Ile Ile Gln Gly Gly Lys His Arg Glu Asn Lys Val Phe Met
            500                 505                 510

Arg Lys Phe Lys Ile Ala Tyr Ser Asn Asn Gly Ser Asp Trp Lys Thr
        515                 520                 525

Ile Met Asp Asp Ser Lys Arg Lys Ala Lys Ser Phe Glu Gly Asn Asn
    530                 535                 540

Asn Tyr Asp Thr Pro Glu Leu Arg Thr Phe Ser Pro Leu Ser Thr Arg
545                 550                 555                 560

Phe Ile Arg Ile Tyr Pro Glu Arg Ala Thr His Ser Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Pro Val Asp Glu Cys Asp Asp Gln Ala
        595                 600                 605

Asn Cys His Ser Gly Thr Gly Asp Asp Phe Gln Leu Thr Gly Gly Thr
    610                 615                 620

Thr Val Leu Ala Thr Glu Lys Pro Thr Ile Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Ser His Ala Gln Leu Arg
            660                 665                 670

Trp Ser Val Leu Thr Ser Lys Thr Gly Pro Ile Gln Asp His Thr Gly
        675                 680                 685

Asp Gly Asn Phe Ile Tyr Ser Gln Ala Asp Glu Asn Gln Lys Gly Lys
    690                 695                 700

Val Ala Arg Leu Val Ser Pro Val Val Tyr Ser Gln Ser Ser Ala His
705                 710                 715                 720
```

```
Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Val Val Gly His Gln Gly Asp His Trp Lys Glu Gly Arg Val
        755                 760                 765

Leu Leu His Lys Ser Leu Lys Leu Tyr Gln Val Ile Phe Glu Gly Glu
    770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Thr Asp Leu Asp
                805                 810                 815

Lys Lys Asn Thr Glu Ile Lys Ile Asp Glu Thr Gly Ser Thr Pro Gly
            820                 825                 830

Tyr Glu Gly Glu Gly Glu Asp Lys Asn Ile Ser Arg Lys Pro Gly
        835                 840                 845

Asn Val Leu Lys Thr Leu Asp Pro Ile Leu Ile Thr Ile Ile Ala Met
850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
                900                 905                 910

Lys Leu Asn Pro Gln Ser Asn Tyr Ser Glu Ala
            915                 920

<210> SEQ ID NO 12
<211> LENGTH: 19
<212> TYPE: PRT
<213> ORGANISM: Homo sapiens

<400> SEQUENCE: 12

Asn Tyr Gln Trp Val Pro Tyr Gln Gly Arg Val Pro Tyr Pro Arg Pro
1               5                   10                  15

Gly Thr Cys

<210> SEQ ID NO 13
<211> LENGTH: 23
<212> TYPE: DNA
<213> ORGANISM: Artificial
<220> FEATURE:
<223> OTHER INFORMATION: PCR primer

<400> SEQUENCE: 13
acaaacgaga aaccagtttc acc                                          23

<210> SEQ ID NO 14
<211> LENGTH: 23
<212> TYPE: DNA
<213> ORGANISM: Artificial
<220> FEATURE:
<223> OTHER INFORMATION: PCR primer

<400> SEQUENCE: 14
ccagcaatat aaagtgtgtc tcg                                          23

<210> SEQ ID NO 15
<211> LENGTH: 25
```

```
<212> TYPE: DNA
<213> ORGANISM: Artificial
<220> FEATURE:
<223> OTHER INFORMATION: PCR primer

<400> SEQUENCE: 15
caatatccgg tttttagagg acgcc                                              25

<210> SEQ ID NO 16
<211> LENGTH: 25
<212> TYPE: DNA
<213> ORGANISM: Artificial
<220> FEATURE:
<223> OTHER INFORMATION: PCR primer

<400> SEQUENCE: 16
cctgctgtct ggacctccac gtcag                                              25
```

THERAPEUTIC AGENT FOR AUTOIMMUNE DISEASES OR ALLERGY, AND METHOD FOR SCREENING FOR THE THERAPEUTIC AGENT

RELATED APPLICATION

This application is a divisional of U.S. application Ser. No. 13/508,192, filed Jul. 16, 2012, which is the National Stage of International Application No. PCT/JP2010/006527, filed Nov. 5, 2010, which claimed priority to Japanese Patent Application No. 2009-254108, filed Nov. 5, 2009; of which all of the disclosures are incorporated herein by reference in their entireties.

TECHNICAL FIELD

Technical Field

The present invention relates to a pharmaceutical composition for preventing or treating autoimmune diseases or allergies, comprising as an active ingredient a substance effective for treating autoimmune diseases or allergies that inhibits binding between NP-1 and Sema3A, such as a Neuropilin-1-Fc (NP-1-Fc), Neuropilin-1 (NP-1) neutralizing antibody, Semaphorin3A (Sema3A) neutralizing antibody or the like. The present invention further relates to a therapeutic method using the pharmaceutical composition, and to a method for screening such inhibitors.

Background Art

Autoimmune diseases involve a specific and continuous adaptive immune response to a self-antigen. Unlike natural immunity and adaptive immunity to external antigens, which ultimately excrete the antigens from the body, adaptive immune responses to self-antigens are continuous because the self-antigen cannot be excreted from its body. Because the self-antigen is supplied continuously, the reaction is further amplified. As a result, the immune system acts on the body's own tissue, causing tissue damage. For example, it is believed that in chronic rheumatoid arthritis and multiple sclerosis, activated T-cells specific to a self-antigen or self-MHC complex cause localized inflammation by activating macrophages, and may even damage tissues directly.

Known organ-specific autoimmune diseases include Basedow's disease and Hashimoto's thyroiditis, which damage the thyroid gland, juvenile-onset diabetes, which results from destruction of the β cells of the islets of Langerhans in the pancreas, Addison's disease, which results from damage to the adrenal cortex, autoimmune hemolytic anemia, idiopathic thrombobocytopenia, demyelinating encephalitis, multiple sclerosis and the like. Known systemic autoimmune diseases include chronic rheumatoid arthritis, systemic lupus erythematosus (SLE), Sjogren's syndrome, Behcet's disease and the like. These diseases are believed to involve autologous antibodies or autoreactive T-cells.

An adaptive autoimmune response is induced by a T-cell response in which specific naive T-cells and some memory cells (hereunder, "naive T-cells and the like") are activated by antigen-presenting cells in the peripheral lymph nodes where naive T-cells and the like are found. Naive T-cells and the like are not usually activated unless they simultaneously receive both a co-stimulatory signal and an antigen-specific stimulatory signal from an antigen-presenting cell. Macrophages and B-cells also have an antigen-presenting function, but it is believed that antigen presentation by dendritic cells plays an important role in T-cell responses.

Mature dendritic cells in the lymph nodes have a strong activation function with respect to naive T-cells. Mature dendritic cells in the lymph tissue have little ability to internalize antigens by phagocytosis, but they express MHC (major histocompatibility complex) class I molecules capable of binding peptides derived from proteins synthesized in the cytoplasm and MHC class II molecules capable of binding peptides derived from proteins in intracellular membrane-bound vesicles constitutively and at a high level. Thus, mature dendritic cells are capable of presenting such antigen-derived peptides. Naive T-cells in the lymph nodes receive antigen-specific stimulatory signals from dendritic cells through T-cell receptors (TCR), and co-stimulatory signals through CD28. When they bind to MHC class I molecules, naive CD8T cells differentiate into cytotoxic T-cells and produce cellular immunity. On the other hand, naive CD4T cells differentiate into Th1 cells, Th2 cells or Th17 cells when they bind to MHC class II molecules. IL-17 production is characteristic of Th17 cells, which are known to be involved in autoimmune disease. Th2 cells (helper CD4T cells) produce humoral immunity by stimulating B cell antibody production.

Allergies are caused by inflammation in response to exogenous antigens, and onset of type IV allergies (also called delayed allergies) is believed to involve activated T-cells and macrophages. As in autoimmune disease, it is believed that dendritic cells and Langerhans cells are primarily responsible for the function of presenting antigens to naive T-cells and the like.

On the other hand, immature dendritic cells, which are normally distributed in peripheral tissue, have some of the antigen presentation function but also have a greater antigen-internalizing ability than mature dendritic cells. Immature dendritic cells internalize by phagocytosis antigens from outside and self-antigens leaked from damaged cells. Immature dendritic cells are stimulated after internalizing the antigen, and migrate from the lymph stream to localized regional lymph nodes (sometimes referred to as "draining lymph nodes" herein, both terms have the same meaning), and mature into dendritic cells and acquire co-stimulatory activity. Thus, in order for dendritic cells to activate naive T-cells in localized regional lymph nodes, stimulated dendritic cells must escape the peripheral tissue and acquire transmigration ability and the ability to interact with lymphoepithelial cells while migrating to the regional lymph. The mechanism by which dendritic cells acquire the ability to migrate to the localized regional lymph nodes is unknown, although it has been reported to involve the complex action of multiple molecules.

For example, expression of CC chemokine receptor 7 (CCR7), which binds to the lymph node/lymphoepithelial cell-derived CC chemokine ligand 21 (CCL21) and also to CCL19, has been shown to play an important role in trafficking of dendritic cells from peripheral tissue to regional lymph nodes (Non-patent Document 1). Moreover, ICAM1 has been shown to play an important role in transmigration across the lymphoepithelial cells (Non-patent Document 2).

On the other hand, it has been reported that non-autoimmune T-cell immunity is reduced in vivo or in vitro when expression of Pleaxin-A1 is suppressed with shRNA in mouse dendritic cell line lymphoma cells (Non-patent Document 3). Plexin-A1 signal analysis in dendritic cells and osteoclasts has also shown that Plexin-A1 forms heteroreceptors with Trem-2 and DAP-12 in the cells. It has also been shown that recombinant soluble Sema6D protein stimulation promotes osteoclast differentiation from precursor cells and expression of IL-12 and other inflammatory cytokines from dendritic cells, and that while Sema6D binds to wild-type dendritic cells, it hardly binds to dendritic cells from Plexin-A1 deficient mice. It has been reported that T-cell immune responses are much weaker in Plexin-A1 deficient mice, which spontaneously develop osteopetrosis caused by abnormal osteoclast differentiation (Non-patent Document 4). Plexin-A1 inhibition with shRNA in mouse dendritic cells has shown that Plexin-A1 controls actin framework localization in the immune synapses of dendritic cells and T-cells via activation of signal transduction factor Rho (Non-patent Document 5).

Plexin-A1 is reported to act as a receptor that exercises various functions by binding with a variety of co-receptors, and to form receptors with VEGF receptor and OFF-Track during heart morphogenesis in chickens, and to act as a nerve repulsion factor by forming a Type 3 Semaphorin receptor together with NP-1, and also to affect axon guidance and cardiac organ formation by acting as a receptor for the Type 6 Semaphorins Sema6C and Sema6D.

The reference documents cited in the specification are as follows. The entire content described in these documents is incorporated herein by reference. None of these documents is admitted to constitute prior art with respect to the present invention.

[Non-patent Document 1] L. Ohl et al., Immunity 21, 279 (2004)
[Non-patent Document 2] L. A. Johnson et al., J. Exp. Med. 203, 2763 (2006)
[Non-patent Document 3] A. W. Wong et al., Nat. Immunol 4, 891 (2003)
[Non-patent Document 4] N. Takegahara et al., Nat. Cell. Biol. 8, 615 (2006)
[Non-patent Document 5] Eun S Y et al., J. Immunol 1774271 (2006)

DISCLOSURE OF THE INVENTION

In light of the circumstances described above, it is an object of the present invention to provide a therapeutic agent for treating autoimmune diseases or allergic diseases in patients who have observed symptoms of autoimmune diseases or allergies.

The inventors has now discovered that Plexin-A1, which is a principal receptor for Class III and Class VI Semaphorins, plays an important role in trafficking of dendritic cells to the lymph nodes, and in antigen-specific T-cell responses. Also discovered is that expression of Sema3A, rather than Sema6C or Sema6D, is required for migration of dendritic cells as they pass through the endothelial cells of the lymph channels, and Sema3A was found to stimulate myosin-II activity and induce actomyosin contraction. Based on these findings, the inventors found that an inhibitor that inhibits binding between Sema3A and an NP-1/Plexin-A1 heteroreceptor expressed in dendritic cells suppresses migration of dendritic cells to regional lymph nodes, thereby controlling T-cell activation in the regional lymph nodes. The inventors also discovered that the inhibitor of the present invention cures or prevents autoimmune diseases and allergic diseases such as contact dermatitis. The inventors further discovered that inhibition of binding between Sema3A and a NP-1/Plexin-A1 heteroreceptor expressed in dendritic cells can be used as a marker to screen for therapeutic agents for autoimmune diseases, allergic diseases such as contact dermatitis, and other cellular immune diseases.

The present invention provides the following:

[1] A therapeutic agent for treating a cellular immune disease, comprising as an active ingredient a substance that inhibits binding between a Neuropilin-1/Plexin-A1 heteroreceptor and Sema3A,

[2] The therapeutic agent according to [1], wherein the substance is a Sema3A neutralizing antibody,

[3] The therapeutic agent according to [1], wherein the neutralizing antibody is an antibody that binds to a peptide having the sequence of amino acids Nos. 363 to 381 in SEQ ID No: 1,

[4] The therapeutic agent according to [3], wherein the sequence of the peptide is NYQWVPYQGRVPYPRPGTC,

[5] The therapeutic agent according to [1], wherein the substance is a Neuropilin-1 neutralizing antibody,

[6] The therapeutic agent according to [5], wherein the neutralizing antibody is an antibody that binds to a peptide having the sequence of amino acids Nos. 265 to 857 in SEQ ID No: 2,

[7] The therapeutic agent according to any of [2] to [6], wherein the neutralizing antibody is a polyclonal antibody,

[8] The therapeutic agent according to any of [2] to [6], wherein the neutralizing antibody is a monoclonal antibody,

[9] The therapeutic agent according to [1], wherein the substance is soluble Neuropilin-1,

[10] The therapeutic agent according to [9], wherein the soluble Neuropilin-1 is:
  (1) a polypeptide comprising amino acids Nos. 23 to 589 in SEQ ID NO: 2,
  (2) a polypeptide comprising amino acids Nos. 23 to 857 in SEQ ID NO: 2,
  (3) a polypeptide that has an amino acid sequence comprising one or more amino acid deletions, additions or substitutions in the amino acid sequence of the polypeptide of (1) or (2), while retaining Plexin-A1-Sema3A binding activity,
  (4) a polypeptide encoded by a polynucleotide that hybridizes under high stringent conditions with a polynucleotide sequence coding for the polypeptide of (1) or (2), and having Plexin-A1-Sema3A binding activity, and
  (5) a polypeptide that is coded by a polynucleotide that hybridizes under high stringent conditions with the polynucleotide sequence represented by SEQ ID NO: 5, and has Plexin-A1-Sema3A binding activity,

[11] The therapeutic agent according to [1], wherein the substance is a soluble Neuropilin-1 derivative,

[12] The therapeutic agent according to [1], wherein the soluble Neuropilin-1 derivative is a fused polypeptide between Fc and the soluble Neuropilin-1 according to [10],

[13] The therapeutic agent according to [12], wherein the Fc comprises a polypeptide of an amino acid sequence according to any of SEQ ID NOS: 7, 8, 9 and 10,

[14] The therapeutic agent according to [1], wherein the soluble Neuropilin-1 derivative is a polypeptide comprising a polyethylene glycol (PEG) chain added to the soluble Neuropilin-1 according to [10],

[15] The therapeutic agent according to [1] to [14], wherein the cellular immune disease is an autoimmune disease,

[16] The therapeutic agent according to [15], wherein the autoimmune disease is an organ-specific autoimmune disease,

[17] The therapeutic agent according to [16], wherein the organ-specific autoimmune disease is anemia (aplastic anemia, hemolytic anemia, autoimmune hemolytic anemia, idiopathic thrombocytopenia), autoimmune hepatitis, iridocyclitis, scleritis, uveitis, orchitis, idiopathic thrombocytopenia purpura, Basedow's disease, Hashimoto's thyroiditis, juvenile-onset diabetes, inflammatory bowel disease, Addison's disease, demyelinating encephalitis or multiple sclerosis,

[18] The therapeutic agent according to [15], wherein the autoimmune disease is a systemic autoimmune disease,

[19] The therapeutic agent according to [18], wherein the systemic autoimmune disease is atopic dermatitis, chronic rheumatoid arthritis or other arthritis, systemic lupus erythematosus, Sjogren's syndrome, undifferentiated connective tissue disease, antiphospholipid syndrome, various forms of vasculitis (polyarteritis nodosa, allergic granulomatosis and angitis), Wegener's granulomatosis, Kawasaki disease, hypersensitive angitis, Henoch-Schonlein purpurea, Behcet's disease, Takayasu's arteritis, giant cell arteritis, thromboangitis obliterans, polymyalgia rheumatica, essential (mixed) cryoglobulinemia, psoriasis, psoriasis vulgaris and psoriatic arthritis, diffuse fascitis with or without eosinophilia, recurrent panniculitis, recurrent polychondritis, lymphomatoid granulomatosis, erythema nodosum, ankylosing spondylitis, Reiter's syndrome, or various forms of inflammatory dermatitis,

[20] The therapeutic agent according to [1] to [14], wherein the cellular immune disease is a delayed-type allergic disease,

[21] The therapeutic agent according to [20], wherein the delayed-type allergic disease is contact dermatitis, metal dermatitis, allergic contact dermatitis, Sjogren's syndrome, infectious allergy, drug-induced pneumonia or Guillan-Barre syndrome,

[22] A method for screening a therapeutic agent for treating a cellular immune disease comprising the steps (a), (b) and (c):
 (a) bringing a Sema3A polypeptide into contact with a polypeptide having a Neuropilin-1 extracellular domain in the presence of a test substance;
 (b) measuring a signal produced by the interaction between the Sema3A polypeptide and the polypeptide having a Neuropilin-1 extracellular domain in the presence of the test substance, and comparing the same with a signal (control) produced by the interaction between the Sema3A polypeptide and the polypeptide having a Neuropilin-1 extracellular domain in the absence of the test substance; and
 (c) selecting a test substance that reduces the signal in comparison with the control based on the comparative results obtained in the step (b),

[23] A method for screening a therapeutic agent for treating a cellular immune disease comprising the steps (a), (b) and (c):
 (a) bringing a Sema3A polypeptide into contact with eukaryotic cells expressing Neuropilin-1 and Plexin-A1 in the presence of a test substance;
 (b) measuring a signal produced by the interaction between the Sema3A polypeptide and the eukaryotic cells expressing Neuropilin-1 and Plexin-A1 in the presence of the test substance, and comparing the same with a signal (control) produced by the interaction between the Sema3A polypeptide and the eukaryotic cells expressing Neuropilin-1 and Plexin-A1 in the absence of the test substance; and
 (c) selecting a test substance that reduces the signal in comparison with the control based on the comparative results obtained in the step (b),

[24] The method according to [23], wherein the cells are dendritic cells,

[25] The method according to [23] or [24], wherein the dendritic cells are cells fractionated and induced from peripheral blood,

[26] The method according to [23] or [24], wherein the dendritic cells are cells of a cell line,

[27] The method according to [23] to [26], wherein the signal is activation of Rho kinase,

[28] The method according to [23] to [26], wherein the signal is phosphorylation of myosin-II,

[29] A method according to [23] to [26], wherein the signal is actomyosin contraction,

[30] A method according to [24] to [26], wherein the signal is transmigration of the dendritic cells,

[31] A method for inhibiting activation of Rho kinase in dendritic cells expressing Neuropilin-1 and Plexin-A1, comprising inhibiting binding between Sema3A and Neuropilin-1 expressed on the surface of human dendritic cells,

[32] A method for inhibiting phosphorylation of myosin-II in dendritic cells expressing Neuropilin-1 and Plexin-A1, comprising inhibiting binding between Sema3A and Neuropilin-1 expressed on the surface of human dendritic cells,

[33] A method for inhibiting actomyosin contraction in dendritic cells expressing Neuropilin-1 and Plexin-A1, comprising inhibiting binding between Sema3A and Neuropilin-1 expressed on the surface of human dendritic cells.

In another aspect, the present invention provides a method for treating cellular immune diseases by administering a substance that inhibits binding between Sema3A and a Neuropilin-1/Plexin-A1 heteroreceptor. Preferably, the substance is selected from the group consisting of a Sema3A neutralizing antibody, a Neuropilin-1 neutralizing antibody, soluble Neuropilin-1 and a soluble Neuropilin-1 derivative. Examples of cellular immune diseases that can be treated by the method of the present invention include anemia (aplastic anemia, hemolytic anemia, autoimmune hemolytic anemia, idiopathic thrombocytopenia), autoimmune hepatitis, iridocyclitis, scleritis, uveitis, orchitis, idiopathic thrombocytopenia purpura, Basedow's disease, Hashimoto's thyroiditis, juvenile-onset diabetes, inflammatory bowel disease, Addison's disease, demyelinating encephalitis, multiple sclerosis, atopic dermatitis, chronic rheumatoid arthritis or other arthritis, systemic lupus erythematosus, Sjogren's syndrome, undifferentiated connective tissue disease, antiphospholipid syndrome, various forms of vasculitis (polyarteritis nodosa, allergic granulomatosis and angitis), Wegener's granulomatosis, Kawasaki disease, hypersensitive angitis, Henoch-Schonlein purpurea, Behcet's disease, Takayasu's arteritis, giant cell arteritis, thromboangitis obliterans, polymyalgia rheumatica, essential (mixed) cryoglobulinemia, psoriasis, psoriasis vulgaris and psoriatic arthritis, diffuse fascitis with or without eosinophilia, recurrent panniculitis, recurrent polychondritis, lymphomatoid granulomatosis, erythema nodosum, ankylosing spondylitis, Reiter's syndrome, various forms of inflammatory dermatitis, contact dermatitis, metal dermatitis, allergic contact dermatitis, Sjogren's syndrome, infectious allergy, drug-induced pneumonia and Guillan-Barre syndrome.

In another aspect, the present invention provides an inhibitor of binding between Sema3A and a Neuropilin-1/Plexin-A1 heteroreceptor, for use as a therapeutic agent for treating a cellular immune disease. Preferably, the substance is selected from the group consisting of a Sema3A neutralizing antibody, a Neuropilin-1 neutralizing antibody, soluble Neuropilin-1 and a soluble Neuropilin-1 derivative.

BRIEF DESCRIPTION OF THE DRAWINGS

FIG. 1 shows the involvement of Plexin-A1 in dendritic cell trafficking.

FIG. 2 shows a decrease in the ability of Plexin-A1$^{-/-}$ dendritic cells to pass through lymph channels.

FIG. 3 shows the involvement of Sema3A-NP-1-Plexin-A1 interaction in dendritic cell trafficking.

FIG. 12 shows the migration capability of dendritic cells from Plexin-A1knockout mice.

PREFERRED EMBODIMENT OF THE INVENTION

Figure 4A:
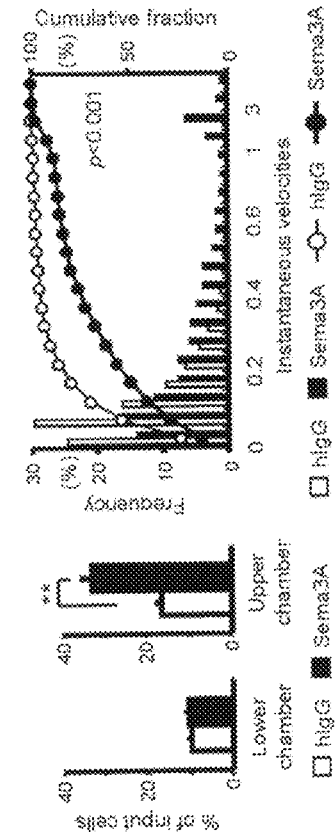
FIG. 4 shows induction of MLC phosphorylation and promotion of actomyosin contractions by Sema3A.

The following definitions are provided to facilitate understanding of the present invention as explained in the description.

The term "antibody" or "antibody peptide" means a full-length antibody (sometimes referred to as a "full-length immunoglobulin" herein) or a binding fragment thereof that competes with the full-length antibody in terms of specific binding, and includes chimera antibodies, humanized antibodies and complete human antibodies. In a specific embodiment, a binding fragment is prepared by recombinant DNA techniques. In another embodiment, a binding fragment is prepared by enzymatic cleavage or chemical cleavage of a full-length antibody. Binding fragments include, but are not limited to, Fab, Fab', F(ab')2 and Fv fragments and single-chain antibodies.

The term "isolated antibody" means an antibody that has been identified and isolated and/or collected from components of its natural environment. Contaminating components of the natural environment are materials that are believed to interfere with the diagnostic and therapeutic use of the antibody, and may include enzymes, hormones, and other proteinaceous or non-proteinaceous soluble materials. In a preferred embodiment, the antibody is purified (1) until the purity exceeds 95 wt % or more, preferably 99 wt % of the antibody, as determined by the Lowry method, (2) sufficiently for determination of at least 15 amino acid residues of the N-terminal or internal amino acid sequence using a spinning cup sequencer, or (3) until it is homogenous according to SDS-PAGE under reducing or non-reducing conditions using Coomassie blue or preferably a silver stain. Isolated antibodies include in situ antibodies inside recombinant cells, where it is believed that at least one kind of component of the natural environment of the antibody is not present. Isolated antibodies are typically prepared with at least one purification stage.

As used herein, a "variant" anti-NP-1 receptor antibody or "variant" anti-Sema3A antibody is a molecule that has an amino acid sequence that differs from that of the parent anti-Neuropilin-1 receptor antibody or parent anti-Sema3A rector antibody by the addition, deletion and/or substitution of one or more amino acid residues in the "parent" antibody sequence. In a preferred embodiment, a variant comprises one or more amino acid substitutions in one or more hypervariable regions of the parent antibody. For example, a variant may comprise at least one substitution, such as about 1 to 10 or preferably about 2 to 5 substitutions, in one or more hypervariable regions of the parent antibody. Typically, a variant has an amino acid sequence having at least 75%, or preferably at least 80%, or more preferably at least 85%, or still more preferably at least 90%, or most preferably at least 95% amino acid sequence identity with a heavy chain variable domain sequence or light chain variable domain sequence of the parent antibody. As used herein, the identity or homology of the amino acid sequences is defined as the percentage of amino acid residues in a candidate sequence which are identical to residues of the parent antibody, as determined by aligning the sequences with inserting gaps as necessary in order to achieve the maximum percent sequence homology. N-terminal, C-terminal or internal elongations, deletions or insertions in the antibody sequence are not considered to affect the identity or homology of the sequence. A variant maintains the ability to bind to a Neuropilin-1 receptor or Sema3A receptor, while preferably having properties superior to those of the parent antibody. For example, a variant may have stronger binding affinity and an enhanced ability to inhibit immune cell stimulation induced by a Neuropilin-1 receptor or Sema3A receptor. Of particular interest are variant antibodies that exhibit at least about 10 times or preferably at least about 20 times or more preferably at least about 50 times the biological activity of the parent antibody.

The term "parent antibody" as used herein means an antibody having an amino acid sequence that is used in preparing a variant. Preferably, a parent antibody has a human framework region, and also has a human antibody constant region if exists. For example, a parent antibody may be a humanized antibody or a complete human antibody.

The term "receptor" is used herein to indicate a cell-associated protein that binds to a bioactive molecule ("ligand") and mediates the action of the ligand on the cell, or a polypeptide subunit of such a protein. The term "receptor polypeptide" is used to indicate complete receptor polypeptide chains comprising isolated functional domains (such as ligand binding domains), and parts of such chains.

The term "modulator" means any compound that modulates the activity, activation or function of a target molecule, including proteins, polypeptides, peptides, antibodies, antibody fragments, large molecules and small molecules (less than 10 kD). For example, when expressed in or brought into contact with dendritic cells, a NP-1 function modulator, NP-1/Pleaxin-A1 heterodimer receptor function modulator or Sema3A function modulator will modulate the function of NP-1, a NP-1/Pleaxin-A1 heterodimer receptor or Sema3A, respectively, with respect to dendritic cells.

The term "antagonist" means any compound that reduces the activity, activation or function of a target molecule, including proteins, polypeptides, peptides, antibodies, antibody fragments, large molecules and small molecules (less than 10 kD). For example, when expressed in or brought into contact with dendritic cells, a NP-1 antagonist, NP-1/Pleaxin-A1 heterodimer receptor antagonist or Sema3A antagonist will cause a reduction in the function of NP-1, the NP-1/Pleaxin-A1 heterodimer receptor or Sema3A, respectively, with respect to dendritic cells. Specific examples of the function include inhibition of Rho kinase activation in dendritic cells, inhibition of myosin-II phosphorylation in dendritic cells, inhibition of actomyosin expansion and contraction in dendritic cells, and inhibition of dendritic cell transmigration and the like.

The term "agonist" means any compound that enhances the activity, activation or function of a target molecule, including proteins, polypeptides, peptides, antibodies, antibody fragments, large molecules and small molecules (less than 10 kD). For example, when expressed in or brought into contact with dendritic cells, a NP-1 agonist, NP-1/Pleaxin-A1 heterodimer receptor agonist or Sema3A agonist will cause an increase in the function of NP-1, a NP-1/Pleaxin-A1 heterodimer receptor or Sema3A, respectively, with respect to dendritic cells.

The term "a chimeric antibody" or "chimeric antibodies" means an antibody or antibodies in which genes coding for the light chain and heavy chain are constructed, typically by genetic engineering methods, from an immunoglobulin variable region gene and constant region gene derived from different species. For example, variable segments of genes from mouse monoclonal antibodies may be linked to γ1, γ3 and other human constant segments to obtain chimera antibodies. Thus, a typical therapeutic chimera antibody is a hybrid protein constructed from a mouse antibody-derived variable region or antigen-binding domain and a human antibody-derived constant region, but other mammalian species can also be used.

The term "epitope" includes any protein determinant capable of binding specifically to an immunoglobulin or T-cell receptor. An epitope determinant typically consists of amino acids, sugar side chains or other chemically active surface groups of a molecule, and generally has specific three-dimensional structural characteristics and specific charge characteristics. More specifically, the term "NP-1 epitope", "NP-1/Pleaxin-A1 heterodimer receptor epitope" or "Sema3A epitope" as used herein refers to a part of a NP-1 polypeptide, NP-1/Plexin-A1 heterodimer receptor or Sema3A polypeptide that has antigenic activity or immunogenic activity in animals, preferably in mammals, and more preferably in mice or humans. An epitope having immunogenic activity is a part of a NP-1 polypeptide, NP-1/Pleaxin-A1 heterodimer receptor or Sema3A polypeptide that induces an immune response in an animal. An epitope having antigenic activity is a part of a NP-1 polypeptide, NP-1/Pleaxin-A1 heterodimer receptor or Sema3A polypeptide to which an antibody binds immunospecifically as determined by immunoassay, using any method well known in the art. An antigen epitope may not necessarily be immunogenic.

As used herein, "epitope tagged" refers to an anti-NP-1 antibody, anti-NP-1/Pleaxin-A1 heterodimer receptor antibody or anti-Sema3A antibody fused with an "epitope tag". An epitope tag polypeptide has enough residues to provide an epitope capable of inducing antibody production, but is sufficiently short so that it does not inhibit the activity of the anti-NP-1 antibody, anti-NP-1/Pleaxin-A1 heterodimer receptor antibody or anti-Sema3A antibody. An epitope tag is preferably highly specific, meaning that an antibody to the epitope does not effectively cross-react with other epitopes. A suitable tag polypeptide generally has at least 6 amino acid residues, and typically has between about 8 to 50 (preferably about 9 to 30) amino acid residues. Examples include the flu HA tag polypeptide and its antibody 12CA5 (Field et al., Mol. Cell. Biol. (1988) 8, 2159-2165), the c-myc tag and the 8F9 antibody, 3C7 antibody, 6E10 antibody, G4 antibody, B7 antibody and 9E10 antibody to the tag (Evan et al., Mol. Cell. Biol. (1985) 5(12), 3610-3616, 1985), and the Herpes Simplex virus glycoprotein D (gD) tag and its antibody (Paborsky et al., Protein Engineering (1990) 3(6), 547-553). In a specific embodiment, an epitope tag is a "salvage receptor binding epitope". The term "salvage receptor binding epitope" as used herein refers to an epitope of the Fc region of an IgG molecule (such as IgG1, IgG2, IgG3 or IgG4) that is responsible for increasing the in vivo serum half-life of the IgG molecule.

The term "fragment" as used herein means a peptide or polypeptide comprising an amino acid sequence of at least 5 continuous amino acid residues, at least 10 continuous amino acid residues, at least 15 continuous amino acid residues, at least 20 continuous amino acid residues, at least 25 continuous amino acid residues, at least 40 continuous amino acid residues, at least 50 continuous amino acid residues, at least 60 continuous amino acid residues, at least 70 continuous amino acid residues, at least 80 continuous amino acid residues, at least 90 continuous amino acid residues, at least 100 continuous amino acid residues, at least 125 continuous amino acid residues or at least 150 continuous amino acid residues of the amino acid sequence of a NP-1 or Sema3A polypeptide or the amino acid sequence of an antibody that binds immunospecifically to a NP-1 or Sema3A polypeptide.

As used herein, the term "immunoglobulin" means a protein consisting of one or more polypeptides substantially encoded by an immunoglobulin gene. One form of immunoglobulin constitutes the basic structural units of an antibody. This form is a tetramer, consisting of two identical pairs of immunoglobulin chains having one light chain and one heavy chain in each pair. In each pair, the variable regions of the light and heavy chains are together responsible for binding to the antigen, while the constant regions are responsible for antibody effector functions.

In the "light chain" (about 25 Kd or 214 amino acids) of a full-length immunoglobulin, the NH2 terminal is encoded by a variable region gene (about 110 amino acids), while the COOH terminal is encoded by the κ or λ constant region gene. Similarly, the "heavy chain" (about 50 Kd or 446 amino acids) of a full-length immunoglobulin is encoded by a variable region gene (about 116 amino acids) and one of the other constant region genes described above (about 330 amino acids). Heavy chains are classified as γ, μ, α, δ or ε, and the antibody isotype of each is defined as IgG, IgM, IgA, IgD and IgE, respectively. Within the light and heavy chains, the variable and constant regions are linked by "J" regions consisting of about 12 or more amino acids, and the heavy chain comprises a "D" region consisting of about 10 or more amino acids (for general reference, see Fundamental Immunology Chapter 7, Paul, W. Ed., 2nd Edition, Raven Press, NY, 1989).

The variable region of the light chain or heavy chain of an immunoglobulin consists of a "framework" region of three interposed hypervariable regions. Thus, the term "hypervariable region" means a region of amino acid residues of an antibody responsible for antigen binding. A hypervariable region contains amino acid residues derived from a "complementarity-determining region" or "CDR" (that is, residues 24 to 34 (CDRL1), 50 to 56 (CDRL2) and 89 to 97 (CDRL3) in the light chain variable domain and residues 31 to 35 (CDRH1), 50 to 65 (CDRH2) and 95 to 102 (H3) in the heavy chain variable domain) (Kabat et al., Sequences of Proteins of Immunological Interest, 5th Edition, Public Health Service, National Institutes of Health, Bethesda, Md. (1991)), and/or residues derived from a "hypervariable loop" (that is residues 26 to 32 (CDR' L1), 50 to 52 (CDR L2) and 91 to 96 (CDR' L3) in the light-chain variable domain and residues 26 to 32 (CDR'H1), 53 to 55 (CDR' H2) and 96 to 101 (CDR' H3) in the heavy-chain variable domain) (Chothia and Lesk, J. Mol. Biol. (1987) 196, 901-917). A "framework region" or "FR" residue is a variable domain residue other than a hypervariable region residue as defined herein. The sequences of the framework regions of different light chains or heavy chains are relatively conserved within species. Thus, a "human framework region" is a framework region that is substantially (about 85% or more, or typically 90% to 95% or more) identical to the framework region of a natural human immunoglobulin. The framework region of an antibody is a framework region combining a light chain and a heavy chain that are components of the immunoglobulin, and is useful in placing and arranging the CDRs. The CDRs are mainly responsible for binding the antigen to the epitope.

The term "humanized" immunoglobulin means immunoglobulin comprising a human framework region and one or more CDRs derived from non-human (typically mouse or rat) immunoglobulin. The non-human immunoglobulin providing the CDR is called a "donor", while the human immunoglobulin providing the framework is called an "acceptor". A constant region is not essential, but when present it must be substantially identical, or in other words at least about 85% to 90% or preferably about 95% or more identical to a human immunoglobulin constant region. Thus, in all the parts of the humanized immunoglobulin, possibly except for the CDRs, are substantially identical to the portions corresponding to a natural human immunoglobulin sequence. A "humanized antibody" is an antibody comprising humanized light-chain immunoglobulin and humanized heavy-chain immunoglobulin. For example, it is believed that humanized antibodies do not encompass typical chimera antibodies as defined above because the entire variable region of a chimera antibody is from non-human.

As used herein, the term "human antibody" includes antibodies having human immunoglobulin amino acid sequences, and antibodies that have been isolated either from human immunoglobulin libraries or from animals that are transgenic with respect to one or more human immunoglobulin species and do no express endogenous immunoglobulin, as explained by, for example, Kucherlapati in U.S. Pat. No. 5,939,598.

The term "genetically modified antibody" means an antibody the amino acid sequence of which has been altered from the sequence of the native antibody. Because antibody preparation involves recombinant DNA technology, the amino acid sequence need not be the same as those found in natural antibodies. An antibody can be re-designed to obtain desired characteristics. Various mutations will be available, for example, by changing one or a few amino acids or by completely re-designing the variable region or constant region. Changes in the constant region are generally made with the aim of improving or modifying complement binding, interactions with membranes, other effector functions and other characteristics. Also various modifications can be implemented as necessary, as discussed below, including modifications that decrease binding of an IgG1 antibody against a Fcγ receptor (WO 99/58572), modifications that lower the isoelectric point of an IgG1 antibody and increase retention in blood, modifications that lower its immunogenicity, and modifications that increase binding with FcRn (WO 2009072604), or modification that reduce the heterogeneity of an IgG2 antibody, modifications that reduce its immunogenicity, and modifications that increase its stability under acidic conditions, or techniques that reduce the heterogeneity of an IgG4 antibody, modifications that reduce its binding to a Fcγ receptor, and modifications that increase its stability under acidic conditions (see WO 2009041613). Changes in the variable region are made in order to improve the antigen binding properties.

In addition to antibodies, immunoglobulins can exist in a variety of other forms (see Hood et al., "Immunology", Benjamin, N.Y., 2nd Edition (1984) and Hunkapiller and Hood, Nature (1986), 323, 15-16), including single chains or Fv, Fab and (Fab')$_2$ fragments, diabodies, linear antibodies, and polyvalent or polyspecific hybrid antibodies (see above and in detail in Lanzavecchia et al., Eur. J. Immunol. (1987) 17, 105), and as single chains (see for example Huston et al., Proc. Natl. Acad. Sci. USA (1988) 85, 5879-5883 and Bird et al., Science (1988) 242, 423-426).

As used herein, the term "single-chain Fv", "single-chain antibody", "Fv" or "scFv" means an antibody fragment that comprises variable regions derived from both heavy and light chains in a single polypeptide chain, but lacks a constant region. In general, a single-chain antibody also comprises a polypeptide linker between the VH domain and VL domain, allowing the formation of a desired structure that is required for antigen binding. Single-chain antibodies are discussed in detail by Pluckthun in The Pharmacology of Monoclonal Antibodies, Vol. 113, Rosenburg and Moore, Eds., Springer-Verlag, New York, pp. 269-315 (1994). Also see WO 88/01649 and U.S. Pat. Nos. 4,946,778 and 5,260, 203. In a specific embodiment, a single-chain antibody may also be a dual-specific and/or a humanized one.

A "Fab fragment" is composed of the CH1 and variable regions of one heavy chain and one light chain. The heavy chain of a Fab molecule cannot form disulfide bonds with another heavy chain molecule.

A "Fab" fragment" comprises one light chain together with one heavy chain that includes a longer constant region placed between the CH1 domain and the CH2 domain so that an interchain disulfide bond can be formed between two heavy chains, allowing the formation of a F(ab')2 molecule.

A "F(ab')2 fragment" comprises two light chains together with two heavy chains each including part of the constant region placed between the CH1 domain and the CH2 domain so that an interchain disulfide bond can be formed between the heavy chains.

The term "diabody" means a small antibody fragment having two antigen binding sites, and the fragment comprises a heavy-chain variable domain (VH) connected to a light-chain variable domain (VL) in the same polypeptide chain (VH-VL). Using a linker that is too short to allow pairing between the two domains on the same chain forces these domains to pair with the complementary domains of another chain, and to create two antigen-binding sites. Diabodies are explained in detail in, for example, EP 404, 097, WO 93/11161, and Hollinger et al., Proc. Natl. Acad. Sci. USA (1993) 90, 6444-6448.

The term "linear antibody" means an antibody explained in Zapata et al., Protein Eng. (1995) 8(10), 1057-1062. Briefly, such an antibody comprises a pair of tandem Fd segments (VH-CH1-VH-CH1) that form a pair of antigen-binding domains. A linear antibody may be bispecific or monospecific.

As used herein, an "immunologically functional immunoglobulin fragment" is a polypeptide fragment comprising at least the variable domains of the immunoglobulin heavy and light chains. An immunologically functional immunoglobulin fragment of the present invention is capable of binding to a ligand, preventing binding of the ligand to a receptor, blocking a biological reaction caused by binding of a ligand to a receptor, or any combination thereof. Preferably, an immunologically functional immunoglobulin fragment of the present invention binds specifically to NP-1, a NP-1/Plexin-A1 heterodimer receptor or Sema3A."

As used herein, the term "monoclonal antibody" is not limited to those antibodies prepared by hybridoma technology. The term "monoclonal antibody" means an antibody derived from a single clone, including any eukaryotic clone, prokaryotic clone or phage clone, without regard for its preparation method.

The present invention also encompasses a genetically modified antibody that is functionally equivalent to the aforementioned antibodies. A modified antibody that provides improved stability and/or therapeutic effectiveness is preferred. Examples of modified antibodies include those having conservative substitutions in amino acid residues and one or more amino acid deletions or additions that do not seriously detract from the effectiveness of antigen binding. As long as its therapeutic utility is maintained, substitutions may range from changes or modifications to one or more amino acid residues to a complete re-design of a region. The antibody of the present invention may be modified after translation (by acetylation and phosphorylated for example), or may be synthetically modified (for example by coupling with a marker group).

Genetically modified antibodies include chimera antibodies derived from anti-NP-1 antibodies, anti-NP-1/Plexin-A1 heterodimer receptor antibodies or anti-Sema3A antibodies. Preferably, a chimera antibody comprises a variable region from a rat or mouse and a constant region from a human, and thus has a longer half-life and less immunogenicity when administered to a human subject. Methods of preparing chimera antibodies are known in the art. Desired chimera antibodies can be formed by linking the variable regions of these antibodies to constant regions of human IgG.

Preferably, the genetically modified anti-NP-1 antibodies, anti-NP-1/Plexin-A1 heterodimer receptor antibodies or anti-Sema3A antibodies used in the present invention include the humanized forms of antibodies explained herein. In a specific embodiment, a humanized antibody comprises a mouse donor immunoglobulin CDR and the heavy chain and light chain frameworks of human acceptor immunoglobulin. Methods for preparing humanized antibodies are disclosed in U.S. Pat. Nos. 5,301,101, 5,585,089, 5,693,762 and 6,180,370. Next, the CDRs of these antibodies can be grafted onto any human frameworks known in the art to prepare a desired humanized antibody.

The antibody of the present invention can be described or specified in terms of epitopes or parts of the polypeptides that they specifically recognize or bind to. As discussed herein, an epitope or polypeptide part can be specified by its N-terminal position and C-terminal position, or by the size of the continuous amino acid residues. The antibody of the present invention can also be described or specified in terms of its cross-reactivity. Antibodies that do not bind to any other analog, ortholog or homolog of the polypeptide of the present invention are also included.

Epitope binning means the use of a competitive binding assay method to identify pairs of antibodies that either can or cannot bind simultaneously to a NP-1 receptor polypeptide, NP-1/Plexin-A1 heterodimer receptor or Sema3A polypeptide, and thereby identify antibodies that bind to the same epitope or to epitopes in a common part of the polypeptide or receptor. Next, a family (or bin) of antibodies having the same binding specificity can be used to define specific epitopes on the NP-1 receptor polypeptide, NP-1/Plexin-A1 heterodimer receptor or Sema3A polypeptide. Epitope binning test provides proof of the existence of epitopes with different antigenicities. However, the test itself cannot identify a specific amino acid sequence or position on the NP-1 receptor polypeptide, NP-1/Plexin-A1 heterodimer receptor or Sema3A polypeptide, or "locate" the epitope on the sequence.

Competition in the binding can be evaluated for any pair of antibodies or fragments. For example, a detection reagent can be used to compare the binding specificity of an antibody or binding fragment from any species or source with the binding specificity of a monoclonal antibody disclosed herein. Epitope binning can be performed using an "isolated antibody" or cell culture supernatant. Binning is often performed using the initial clone supernatant in order to aid selection of clones for further development. The antibodies being compared should have antigen-binding domains from substantially the same species.

The present invention features both a NP-1 receptor-specific antibody and a Sema3A ligand-specific antibody. In addition to identifying competitive antibody binding, epitope binning can be used to identify antibodies against either ligands or receptors that competitively block binning of ligands and their receptors, and substances that inhibit their binding. A useful characteristic of an antibody family (or bin) can often be associated with binding to a specific epitope defined by epitope binning.

Although a competitive binding test does not directly measure binding affinity, the tested antibodies must bind sufficiently strongly to function as competitors. In general, the test conditions are designed to minimize the effects of differences in binding affinity.

The specific binding of the antibody of the present invention can be analyzed by any method known in the art. Many different competitive binding assay systems can be used for epitope binning. Examples of immunoassays that can be used include competitive and non-competitive assay systems using techniques such as Western blotting, radioimmunoassay, ELISA (enzyme-linked immunosorbent assay), "sandwich" immunoassay, immunoprecipitation assay, precipitation reactions, gel diffusion, immunodiffusion assay, agglutination assay, complement binding assay, immunoradiometric assay, fluorescent immunoassay, protein A immunoassay and the like, but these are only a few examples and are not limiting. Such assay methods are common and well-known in the art (see for example Ausubel et al. Eds., 1994, Current Protocols in Molecular Biology, Vol. 1, John Wiley & Sons, Inc., New York). Typical immunoassay methods are explained in brief below (but are not limiting). A common cross-blocking assay method such as that described in Antibodies, A Laboratory Manual, Cold Spring Harbor Laboratory, Ed Harlow and David Lane (1988) can also be implemented.

Biacore is one of many assay systems that are conventionally used for epitope binning of panels of monoclonal antibodies. Many reference documents (for example, The Epitope Mapping Protocols, Methods in Molecular Biology, Vol. 6.6, Glenn E. Morris Ed.) explain alternative methods that can be used for antibody binning, and is expected to provide the same information about antibody binding specificity with respect to the NP-1 receptor, NP-1/Plexin-A1 heterodimer receptor or Sem3A polypeptide. When using a Biacore system, an epitope binning test is performed using a native antigen. Epitope binning studies can be performed using a Biacore 1000™ system (Biacore, Uppsalla, Sweden). BIAlogue™ Version 1.2 software can be used preferably for programming the test methods. For example, when using Biacore for binning mouse monoclonal antibodies produced against NP-1, polyclonal goat anti-mouse IgG Fc antibodies (Jackson ImmunoResearch Laboratories, West Grove, Pa.) can be fixed by covalent binding to a Biacore™ CM5 sensor chip, and used to bind (capture) monoclonal primary antibodies of a test line on the same chip. Next, a polyclonal IgG Fc fragment (Jackson ImmunoResearch Laboratories, West Grove, Pa.) is used to block the open Fc binding sites on the chip. The NP-1 receptor is then injected and bound specifically to the captured monoclonal primary antibodies. The Biacore equipment can measure the amount of protein bound to the sensor chip, and determine binding of both the primary antibody and the NP-1 receptor antigen for each cycle. After the primary antibody and antigen have bound to the chip, a soluble secondary antibody is injected and bound to the previously bound antigen. When the monoclonal secondary antibody is capable of binding to the NP-1 receptor antigen at the same time as the monoclonal primary antibody, its binding is detected by Biacore. However, when the monoclonal secondary antibody cannot bind to the NP-1 receptor antigen at the same time as the monoclonal primary antibody, further binding is not detected. Each monoclonal antibody is tested against itself as a negative control, and the level of the background signal (without binding) is determined.

Label-free competitive ELISA (LFC-ELISA) can also be used for antibody binning. This method is explained in Nagata et al., J. Immuno. Methods (2004) 292, 141-155. A biotin-labeled NP-1 receptor, NP-1/Plaxin-A1 heterodimer receptor or Sema3A polypeptide can be used for epitope binning by the method. For example, when binning mouse monoclonal antibodies produced against the NP-1 receptor, NP-1/Plaxin-A1 heterodimer receptor or Sema3A polypeptide, a microtiter plate is coated with 100 μL/well of goat anti-mouse IgG Fc-γ specific antibody (Jackson ImmunoResearch) diluted 1 μg/mL in ELISA B (PBS, 0.1% Tween 20, 1% BSA). After the coating antibody has been bound for 3 hours at ambient temperature, each conditioned medium containing the monoclonal antibody is diluted with ELISA buffer to an antibody concentration of about 0.5 μg/mL, and bound overnight at 4° C. to the plate coated with the goat anti-mouse IgG (primary antibody). At the same time, a second set of conditioned medium (secondary antibody) is diluted in ELISA buffer in a polystyrene test tube to an antibody concentration of about 0.5 μg/mL, mixed with 50 ng/mL of a biotin label, and incubated overnight at 4° C. After the primary antibody has been incubated with the coating antibody, the plate is blocked with an unrelated antibody, occupying the open binding sites on the plate. A secondary antibody-biotin-NP-1 rector, secondary antibody-biotin-NP-1/Plaxin-A1 heterodimer receptor or secondary antibody-biotin-Sema3A polypeptide mixture is added and bound to the plate. As a (non-competitive) control for the assay, a NP-1 receptor, NP-1/Plaxin-A1 heterodimer receptor or Sema3A polypeptide antigen labeled with 50 ng/mL of biotin (not pre-incubated with the secondary antibody) is added directly to a well containing the fixed primary antibody. After incubation with the secondary antibody complex of the biotin-labeled NP-1 receptor, NP-1/Plaxin-A1 heterodimer receptor or Sema3A polypeptide, 0.5 μg/mL of streptavidin-HRP (Pierce, Rockford Ill.) is added to the plate. These plates are color developed with TMB substrate (BioFX Laboratories, Owings Mills, Md.), and the absorbency of each well at 450 nm is measured with a plate reader (Molecular Devices SpectraMax™ 340, Sunnyvale, Calif.). When the primary antibody binds to a different epitope than the secondary antibody, it indicates that the biotin-labeled secondary antibody complex of the NP-1 receptor, NP-1/Plaxin-A1 heterodimer receptor or Sema3A polypeptide binds to the plate, resulting in a higher measured value for absorbency. When the primary antibody binds to the same epitope as the secondary antibody, it indicates that the biotin-labeled secondary antibody complex of the NP-1 receptor, NP-1/Plaxin-A1 heterodimer receptor or Sema3A polypeptide does not bind to the plate, resulting in a lower measured value for absorbency.

The antibody of the present invention acts as a NP-1 receptor or NP-1/Plaxin-A1 heterodimer receptor antagonist. For example, the present invention encompasses an antibody that partially or completely disrupts the receptor/ligand interaction of the NP-1 receptor or NP-1/Plaxin-A1 heterodimer receptor with Sema3A. The present invention features a receptor-specific antibody, and also features a receptor-specific antibody that does not block ligand binding but does block receptor activation. Receptor activation (that is, signal transduction) can be determined by techniques that are explained herein or known in the art. For example, receptor activation can preferably be determined by detecting phosphorylation (for example, tyrosine or serine/threonine) of the receptor or its myosin-II or other substrate by immunoprecipitation and subsequent Western blotting analysis. In a specific embodiment, an antibody is provided which reduces ligand or receptor activity to at least 90%, or at least 80%, or at least 70%, or at least 60%, or at least 50% of activity observed in the absence of the antibody.

The present invention also features a receptor-specific antibody that prevents both ligand binding and receptor activation, and an antibody that recognizes a receptor-ligand complex. Similarly, the present invention also includes a neutralizing antibody that binds to a ligand and prevents binding of the ligand to a receptor, and an antibody that binds to a ligand and prevents it from activating a receptor, but does not prevent binding of the ligand to the receptor. These antibodies can be specified as antagonists to biological activity such as the specific biological activity of a peptide of the present invention.

The present invention also provides a method for screening "functional modulators" of Sema3A, which regulate binding between Sema3A and the NP-1/Plaxin-A1 heteroreceptor. A test substance used in the screening method can be an anti-NP-1 antibody, anti-NP-1/Plaxin-A1 heterodimer receptor antibody or anti-Sema3A antibody, an organic or inorganic chemical substance, or a biochemical molecule or composition as appropriate.

The present invention also provides a method for designing a Sema3A "functional modulator" that regulates binding between Sema3A and the NP-1/Plaxin-A1 heteroreceptor, and also provides the modulator. Preferably, a Sema3A functional modulator may be designed that comprises as a constituent element a polypeptide comprising an extracellular domain of NP-1 that are necessary for binding with Sema3A. A polypeptide comprising the extracellular domains of NP-1 that are necessary for binding with Sema3A can be used as a functional modulator. Derivatives prepared from such polypeptides may also be used.

As long as it regulates binding between Sema3A and the NP-1/Plexin-A1 heteroreceptor, a "derivative" of the present invention may be a substance having a known modification as described below for purposes of in vivo stabilization. The term "derivative" is used in the specification and in the Claims in a way that encompasses modifications for purposes of in vivo stabilization unless it is clear from the context that it is not the case.

"Hybridization under high stringent conditions" as used herein means that a polynucleotide codes for an equivalent of a specific polynucleotide sequence to be hybridized, and the polypeptide encoded by the equivalent is equivalent to the polypeptide encoded by the specific polynucleotide to be hybridized. Thus, a polynucleotide that "hybridizes under high stringent conditions" may be a polynucleotide that does not hybridize under moderately stringent conditions. The hybridization conditions can be set with reference to known conditions (Current Protocols in Molecular Biology, John Wiley & Sons, 6.3.1-6.3.6, 1999). The conditions for hybridization under high stringent conditions might be washing one or more times with 6×SSC (sodium chloride/sodium citrate) at 45° C. followed by 0.2×SSC/0.1% SDS at 50 to 65° C. Hybridization under moderately stringent conditions might involve washing one or more times with 2×SSC at 30° C. followed by 1×SSC/0.1% SDS at 30 to 50° C.

Preparation of Anti-Neuropilin-1 Antibody, Anti-NP-1/Plexin-A1 Heterodimer Receptor Antibody and Anti-Sema3A Antibody NP-1 (also referred to as "NP-1 receptor" herein, both terms have the same meaning), an NP-1/Plexin-A1 polypeptide or other NP-1/Plexin-A1 heterodimer receptor, or Sema3A can be used to prepare antibodies that bind to an epitope, peptide or polypeptide within the antigen. A particularly useful anti-NP-1 antibody is one that "binds specifically" to NP-1. A particularly useful anti-NP-1/Plexin-A1 heterodimer receptor antibody is one that "binds specifically" to an NP-1/Plexin-A1 heterodimer receptor. A particularly useful anti-Sema3A antibody is one that "binds specifically" to Sema3A. Binding is said to be specific when it exhibits at least one of the following two properties: (1) there is a threshold level of binding activity, and (2) there is no significant cross-reaction with related polypeptide molecules.

Regarding the first property, a threshold level of binding is determined when an anti-NP-1 antibody, anti-NP-1/Plexin-A1 heterodimer receptor antibody or anti-Sema3A antibody binds, respectively, to an NP-1 polypeptide, peptide or epitope, an NP-1/Plexin-A1 heterodimer receptor polypeptide, peptide or epitope, or a Sema3A polypeptide, peptide or epitope with at least 10 times the binding affinity as with a control peptide. The antibody preferably exhibits binding affinity (Ka) of at least $10^6 M^{-1}$, or more preferably at least $10^7 M^{-1}$, or still more preferably at least $10^8 M^{-1}$, or most preferably at least $10^9 M^{-1}$. The binding affinity of an antibody can be easily determined by those skilled in the art based on Scatchard, G., Ann. NY Acad. Sci. (1949) 51, 660-672.

Regarding the second property, if the antibody detects a NP-1 polypeptide, Sema3A polypeptide or other polypeptide in standard Western blot analysis, but does not detect other presently-known related polypeptides, the antibody does not cross-react with other related polypeptide molecules. Examples of known related polypeptides may include those disclosed in the prior art, such as known orthologs and paralogs, as well as similar known members of the protein family.

Screening can be carried out using non-human NP-1, a non-human NP-1/non-human Plexin-A1 heterodimer receptor or non-human Sema3A, and human NP-1, a human NP-1/human Plexin-A1 heterodimer receptor or human Sema3A.

Antibodies can also be screened against known related polypeptides to isolate those which bind specifically to NP-1 or Sema3A. For example, antibodies produced in response to NP-1 or Sema3A are adsorbed by related polypeptides attached to an insoluble matrix. Antibodies specific to N-1 or Sema3A will pass through the matrix under suitable buffer conditions. Polyclonal antibodies and monoclonal antibodies that do not cross-react with known, closely-related polypeptides can be isolated by the screening process (Antibodies: A Laboratory Manual, Harlow and Lane (Eds.), Cold Spring Harbor Laboratory Press, 1988; Current Protocols in Immunology, Cooligan et al. (Eds.), National Institutes of Health, John Wiley and Sons, Inc., 1995). Screening and isolation of a specific antibody is well-known in the art (see Fundamental Immunology, Paul (Ed.), Raven Press, 1993; Getzoff et al., Adv. in Immunol. (1988) 43, 1-98; Monoclonal Antibodies: Principles and Practice, Goding, J. W. (Ed.), Academic Press Ltd., 1996; Benjamin et al., Ann. Rev. Immunol. (1984) 2, 67-101). A specific anti-NP-1 antibody or anti-Sema3A antibody can be detected by various methods known in the art and disclosed below.

An antibody against an antigen comprising antigenic NP-1 that is similar to NP-1, NP-1/Plexin-A1 heterodimer receptor or Sema3A, or an antibody against an antigen comprising NP-1/Plexin-A1 heterodimer receptor or Sema3A can be prepared using antigenic NP-1 that is similar to NP-1, NP-1/Plexin-A1 heterodimer receptor or Sema3A, or NP-1/Plexin-A1 heterodimer receptor or Sema3A. The preparation can be accomplished by inoculating animals with antigenic NP-1 that is similar to NP-1, NP-1/Plexin-A1 heterodimer receptor or Sema3A, or NP-1/Plexin-A1 heterodimer receptor or Sema3A as an antigen (immunogen), and inducing an immune response in the animals. A person skilled in the art should be aware that a polypeptide having an antigenic epitope comprises a sequence of at least 6, or preferably at least 9, or still more preferably at least 15 to about 30 consecutive amino acid residues of NP-1, a NP-1/Plexin-A1 heterodimer receptor or Sema3A (for example, SEQ ID NO:1, SEQ ID NO:2, SEQ ID NO:3). Polypeptides comprising additional portions of NP-1, a NP-1/Plexin-A1 heterodimer receptor or Sema3A, or in other words polypeptides comprising from 30 to 100 residues or up to the entire length of the amino acid sequence, are also included. As explained below, antigens or immunogenic epitopes can preferably include bound tags, adjuvants, and carriers. In the case of NP-1, for example, suitable antigens comprise the sequence of amino acids Nos. 265 (Leu) to 857 (Ile) (SEQ ID NO:2) in the NP-1 polypeptide encoded by SEQ ID NO:2, or amino acid fragments comprising 9 to 592 consecutive amino acid residues of this sequence. Desirable peptides for use as antigens are the coagulation factor V/VII domain and MAM domain disclosed herein and NP-1 hydrophilic peptides such as those predicted by a person skilled in the art from hydrophobic plotting, which is determined, for example, from a Hopp/Woods hydrophilic profile based on a 6-residue sliding window by ignoring the buried G residue, S residue and T residue and the exposed H residue, Y residue and W residue. Suitable antigens include, for example, polypeptides having antigenic epitopes predicted by Jameson-Wolf plotting using a DNASTAR Protean program (DNASTAR, Inc., Madison, Wis.). In the case of Sema3A, for example, suitable antigens comprise the sequence of amino acids Nos. 363 (Asn) to 381 (Cys) in the Sema3A polypeptide encoded by SEQ ID NO:1, or amino acid fragments comprising 9 to 19 consecutive amino acid residues of this sequence. A peptide having the sequence NYQWVPYQGRVPYPRPGTC (SEQ ID NO:12) may preferably used. Conserved motifs and variable regions between conserved motifs of NP-1 and Sema3A are also suitable antigens. Suitable antigens also include, for example, polypeptides that incorporate an extracellular domain other than Plexin-A1, such as the VEGF receptor. These include the NP-1/VEGF receptor heterodimer receptor, which is similar to the NP-1/Plexin-A1 heterodimer receptor described above. The corresponding region of the mouse NP-1 polypeptide (residues 265 (Leu) to 857 (Ile), SEQ ID NO:11) can also be used to prepare antibodies against mouse NP-1. An antibody produced by the immune reaction can also be isolated and purified as explained in the description. Methods for preparing and isolating polyclonal antibodies and monoclonal antibodies are well known in the art (see for example Current Protocols in Immunology, Cooligan et al. (Eds.): National Institutes of Health, John Wiley and Sons, Inc., 1995; Sambrook et al., Molecular Cloning: A Laboratory Manual, 2nd Ed., Cold Spring Harbor, N.Y., 1989; and Hurrell, J. G. R. Ed., Monoclonal Hybridoma Antibodies: Techniques and Applications, CRC Press, Inc., Boca Raton, Fla., 1982).

A polyclonal antibody against a polypeptide comprising recombinant NP-1 or an NP-1 polypeptide isolated from a natural source, or a polyclonal antibody against a recombinant Np-1/Plexin-A1 heterodimer receptor or an NP-1/Plexin-A1 heterodimer receptor isolated from a natural source, can be prepared by those skilled in the art using well-known methods. Similarly, a polyclonal antibody against a polypeptide comprising recombinant Sema3A or a Sema3A polypeptide isolated from a natural source can be prepared by those skilled in the art using well-known methods (see for example Green et al.: "Production of Polyclonal Antisera", Imuunochemical Protocols (Manson Ed.), p. 1-5 (Humana Press 1992); and Williams et al.: "Expression of foreign proteins in *E. coli* using plasmid vectors and purification of specific polyclonal antibodies", DNA Cloning 2: Expression Systems, 2nd Edition, Glover et al. (Ed), p. 15 (Oxford University Press, 1995)). The immunogenicity of a NP-1 polypeptide, NP-1/Plexin-A1 heterodimer receptor or Sema3A polypeptide can be enhanced using an adjuvant such as alum (aluminum hydroxide), Freund's complete adjuvant or Freund's incomplete adjuvant. Polypeptides that are useful for immunization also include fused polypeptides, such as fused products of NP-1 or parts thereof or Sema3A or parts thereof with immunoglobulin polypeptides or maltose binding proteins. A polypeptide immunogen may be a full-length molecule or a part thereof. When a polypeptide part is "hapten-like", such a part is considered advantageous for binding or linking to a macromolecule carrier (for example, keyhole limpet hemocyanin (KLH), bovine serum albumin (BSA), tetanus toxoid or the like) for purposes of immunization.

Polyclonal antibodies are typically produced in animals such as horses, cows, dogs, chickens, rats, mice, rabbits, guinea pigs, goats or sheep, but the anti-NP-1 antibody, anti-NP-1/Plexin-A1 heterodimer receptor antibody or anti-Sema3A antibody of the present invention can also be derived from an anthropoid primate. Conventional techniques for producing diagnostically and therapeutically useful antibodies in baboons can be found for example in WO 91/11465 (Goldenberg et al.) and Losman et al., Int. J. Cancer (1990) 46, 310.

Alternatively, anti-NP-1 monoclonal antibody, anti-NP-1/Plexin-A1 heterodimer receptor monoclonal antibody or anti-Sema3A monoclonal antibody can be prepared. Rodent monoclonal antibody against a specific antigen can be obtained by methods known in the art (see for example Kohler et al., Nature (1975) 256, 495; Coligan et al. (Eds.), Current Protocols in Immunology, Vol. 1, pp. 2.5.1-2.6.7 (John Wiley & Sons, 1991) ["Coligan"]; Picksley et al.: "Production of monoclonal antibodies against proteins expressed in *E. coli*", DNA Cloning 2: Expression Systems, 2nd Edition, Glover et al (Eds.), p. 93 (Oxford University Press, 1995)).

Briefly, anti-NP-1 monoclonal antibody and anti-Sema3A monoclonal antibody can be obtained by injecting a composition comprising the NP-1 receptor or Sema3A into mice, collecting serum samples to determine the presence of antibody, removing spleens and collecting B-lymphocytes, and fusing the B-lymphocytes to myeloma cells to prepare hybridomas which are then cloned. Positive clones that produce an antibody against the antigen are selected, clones that produce the antibody against the antigen are cultured, and the antibody is isolated from the resulting hybridoma culture.

An anti-NP-1 antibody, anti-NP-1/Plexin-A1 heterodimer receptor antibody or Sema3A antibody of the present invention can also be derived from human monoclonal antibodies. A human monoclonal antibody can be obtained from a transgenic mouse that has been manipulated to produce a specific human antibody in response to antigen inoculation. Using this technology, elements of genetic loci of human heavy chain and human light chain are introduced into a mouse strain derived from an embryonic stem cell line comprising targeted damage to gene loci of the endogenous heavy chain and light chain. The transgenic mouse can synthesize a human antibody specific to a human antigen, and the mouse can also be used to prepare a hybridoma that secretes a human antibody. Methods for obtaining a human antibody from a transgenic mouse are described for example in Green et al., Nature Genet. (1994) 7, 13; Lonberg et al., Nature (1994) 368, 856 and Taylor et al., Int. Immun. (1994) 6, 579.

Monoclonal antibodies can be isolated and purified from hybridoma culture by various well established techniques. Such isolation techniques include affinity chromatograph using protein-A sepharose, size exclusion chromatography, and ion-exchange chromatography (see for example Coligan above, p. 2.7.1-2.7.12 and 2.9.1-2.9.3; and Baines et al.: "Purification of Immunoglobulin G (IgG)", Methods in Molecular Biology, Vol. 10, pp. 79-104 (The Humana Press, Inc. 1992)).

For specific applications, it may be desirable in some cases to prepare a fragment of an anti-NP-1 antibody, anti-NP-1/Plexin-A1 heterodimer receptor antibody or Sema3A antibody. Such an antibody fragment can be obtained for example by proteolytic hydrolysis of an antibody. An antibody fragment can be obtained by pepsin digestion or papain digestion of a full-length antibody by conventional methods. For example, an antibody fragment can be prepared by enzymatic cleavage of an antibody with pepsin, so as to provide a 5S fragment denoted F(ab')2. This fragment can be further cleaved using a thiol reducing agent to produce a 3.5S Fab' monovalent fragment, and optionally a blocking group for the sulfhydryl groups resulting from cleavage of disulfide linkages. As an alternative method, two monovalent Fab fragments and one Fc fragment can be produced directly by enzymatic cleavage using pepsin. These methods are disclosed in Goldenberg, U.S. Pat. No. 4,331,647; Nisonoff et al., Arch. Biochem. Biophys. (1960) 89, 230; Porter, Biochem. J. (1959) 73, 119; Edelman et al., Methods in Enzymology, Vol. 1, p. 422 (Academic Press 1967); and Coligan above, pp. 2.8.1-2.8.10 and 2.10-2.10.4.

Other methods of cleaving antibodies, such as separation of heavy chains to form monovalent light-heavy chain fragments, further cleavage of fragments, or other enzymatic, chemical or genetic techniques may also be used as long as the fragments bind to the antigen that is recognized by the intact antibody.

As an example, Fv fragments may comprise associated VH and VL chains. The association may be non-covalent, as explained by Inbar et al., Proc. Nat'l Acad. Sci. USA (1972) 69, 2659. Alternatively, these variable chains can be linked by an intermolecular disulfide bond, or cross-linked by a chemical substance such as glutaraldehyde (see for example Sandhu, Crit. Rev. Biotech. (1992) 12, 437).

Fv fragments may comprise VH and VL chains connected by a peptide linker. A single-chain antigen-binding protein (scFv) is prepared by constructing a structural gene comprising DNA sequences encoding the VH and VL domains connected by an oligonucleotide. The structural gene is inserted into an expression vector, and the vector is then introduced into a host cell such as E. coli. The recombinant host cells synthesize a single polypeptide chain having a linker peptide bridging two V domains. Methods for preparing scFvs are explained for example in Whitlow et al., Methods: A Companion to Methods in Enzymology 2, 97 (1991) (also see Bird et al., Science (1988) 242, 423; Ladner et al., U.S. Pat. No. 4,946,776; Pack et al., Bio/Technology (1993) 11, 1271; and Sandhu, above).

For example, scFV can be obtained by exposing lymphocytes to an NP-1 polypeptide, NP-1/Plexin-A1 heterodimer receptor or Sema3A polypeptide in vitro, and selecting scFV from an antibody displaying library of antibodies displayed in phage vectors or similar vectors (for example, using a fixed or labeled NP-1 polypeptide, NP-1/Plexin-A1 heterodimer receptor or Sema3A polypeptide). A gene encoding a latent NP-1 binding polypeptide, NP-1/Plexin-A1 heterodimer receptor binding polypeptide or Sema3A binding polypeptide can be obtained by screening a library of random peptides displayed on phages (phage display) or bacteria such as E. coli. Nucleotide sequences encoding the polypeptides can be determined by a number of methods, such as random mutagenesis and random polynucleotide synthesis. Techniques for preparing and screening such random peptide display libraries are known in the art (Ladner et al., U.S. Pat. No. 5,223,409; Ladner et al., U.S. Pat. No. 4,946,778; Ladner et al., U.S. Pat. No. 5,403,484; Ladner et al., U.S. Pat. No. 5,571,698; and Kay et al., Phage Display of Peptides and Proteins (Academic Press, Inc. 1996)). Random peptide display libraries and kits for screening such libraries are commercially available for example from Clontech Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). A sequence comprising a NP-1 polypeptide disclosed herein can be used to screen a random peptide display library to identify a polypeptide that binds to a NP-1 polypeptide, NP-1/Plexin-A1 heterodimer receptor or Sema3A polypeptide.

Another embodiment of the antibody fragment is a peptide encoding one complementarity-determining region (CDR). A CDR peptide ("minimal recognition unit") can be obtained by constructing a gene encoding a CDR of the antibody of interest. Such a gene can be prepared for example by using a polymerase chain reaction to synthesize a variable region using RNA from the antibody-producing cell (see for example Larrick et al., Methods: A Companion to Methods in Enzymology (1991) 2, 106; Courtenay-Luck, "Genetic Manipulation of Monoclonal Antibodies", Monoclonal Antibodies: Production, Engineering and Clinical Application, Ritter et al. (Eds.), p. 166 (Cambridge University Press, 1995); and Ward et al., "Genetic Manipulation and Expression of Antibodies", Monoclonal Antibodies: Principles and Applications, Birch et al. (Eds.), p. 137 (Wiley-Liss, Inc. 1995)).

Alternatively, a "humanized" monoclonal antibody can be used appropriately as an anti-NP-1 antibody, anti-NP-1/Plexin-A1 heterodimer receptor antibody or anti-Sema3A antibody. A humanized monoclonal antibody is prepared by introducing a mouse complementarity-determining region derived from the variable chains of the heavy and light chains of mouse immunoglobulin into a human variable domain. Next, relevant residues of the human antibody are substituted for the corresponding mouse framework region. Potential problems associated with the immunogenicity of the mouse constant region may be avoided by using antibody constituents derived from humanized monoclonal antibodies. Conventional techniques for cloning mouse immunoglobulin variable domains are described for example in Orlandi et al., Proc. Nat'l Acad. Sci. USA (1989) 86, 3833. Techniques for preparing humanized monoclonal antibodies are described for example in Jones et al., Nature (1986) 321, 522; Carter et al., Proc. Nat'l Acad. Sci. USA (1992) 89, 4285; Sandhu, Crit. Rev. Biotech. (1992) 12, 437; Singer et al., J. Immun. (1993) 150, 2844; Sudhir (Ed.), Antibody Engineering Protocols (Humana Press, Inc., 1995), Kelley, "Engineering Therapeutic Antibodies"; Protein Engineering: Principles and Practice, Cleland et al. (Eds.), pp. 399-434 (John Wiley & Sons, Inc., 1996); and Queen et al., U.S. Pat. No. 5,693,762 (1997).

The anti-NP-1 antibody, anti-NP-1/Plexin-A1 heterodimer receptor antibody or anti-Sema3A antibody of the present invention or an antibody fragment thereof can preferably be PEG-modified using methods known in the art and explained in the description.

The antibody of the present invention also includes modified antibodies, or in other words derivatives comprising any type of molecule covalently bound to the antibody so as not to interfere with inhibition of receptor activation or binding of the antibody against an NP-1 polypeptide, NP-1/Plexin-A1 heterodimer receptor or Sema3A polypeptide. For example, such antibody derivatives include, but are not limited to, antibodies modified with glycosylation, acetylation, PEG-modification, phosphylation, amidation, or derivatization by known protective/blocking groups, proteolytic cleavage, or linkage to cellular ligands or other proteins. Any of a number of chemical modifications can be accomplished by known techniques including, but not limited, too, specific chemical cleavage, acetylation, formylation, and metabolic synthesis of tunicamycin. A derivative may also comprise one or more non-natural amino acids.

Functional Screening of Sema3A Function Modulators

The inventors have found that NP-1 is the other part of a Plexin-A1 heteroreceptor involved in migration of dendritic cells to regional lymph nodes, that its ligand is Sema3A, and that formation of a ligand-receptor complex between the Sema3A ligand and the NP-1/Plexin-A1 heterodimer receptor causes actomyosin contractions via phosphorylation of myosin-II by Rho kinase in the dendritic cells, inducing dendritic cell trafficking. Based on the finding that NP-1 is the other receptor of a heterodimer receptor comprising Plexin-A1 that is involved in dendritic cell trafficking, and that the ligand is Sema3A, the inventors here demonstrate that the NP-1/Plexin-A1 heterodimer receptor and the Sema3A ligand may be used to screen for modulators that could be used as therapeutic agents for cellular immune diseases caused by cytotoxic T-cells and macrophages that are stimulated by antigens presented by dendritic cells in the regional lymph nodes.

The present invention provides a method of screening for modulators of the Sema3A functions of dendritic cell transmigration, differentiation or activation, comprising bringing a composition comprising a Sema3A polypeptide into contact with dendritic cells with or without a candidate drug;

measuring dendritic cell transmigration and changes in an intracellular signal with and without the drug; and identifying a candidate drug as a modulator of Sema3A function with respect to dendritic cells based on the measurement results with and without the candidate drug.

In a related embodiment, the present invention provides a method of screening for a modulator of Sema3A function pertaining to the NP-1/Plexin-A1 heterodimer receptor and the Sema3A ligand, as substantially described above. Actual methods of screening for modulators of Sema3A function can be generally classified into methods where the Sema3A polypeptide or its derivative is brought into contact with a test substance in vitro, and methods where the test substance is administered to a non-human animal in vivo. Among these methods, the following three methods are given as specific examples of the method of the present invention for screening for a Sema3A function modulator that involve bringing the Sema3A polypeptide or its derivative into contact with a test substance in vitro.

1) Methods Using Cells Expressing the NP-1/Plexin-A1 Heterodimer Receptor

Specifically, the following methods are given as examples of methods of screening of the present invention using cells expressing the NP-1/Plexin-A1 heterodimer receptor. To screen for a Sema3A function modulator that is an antagonist, a fused polypeptide (Sema3A-AP) of Sema3A and alkaline phosphatase (AP) is prepared as described below. A transformant expressing the NP-1/Plexin-A1 heterodimer receptor on the cell surface is also prepared. Next, binding of the Sem3A-AP to cells is detected by the alkaline phosphatase activity when (i) Sema3A-AP is added, and (ii) Sema3A-AP and a test substance are added. If AP activity is lower in situation (ii) in comparison with situation (i) or not detected, the test substance is suggested to be an antagonist of Sema3A.

In another embodiment of the present invention, dendritic cells and a dendritic cell line induced by fractionation from peripheral blood can preferably be used as cells expressing the NP-1/Plexin-A1 heterodimer receptor. Dendritic cells prepared in vitro by culturing mononuclear cells fractionated from peripheral blood together with GM-CSF or IL-4 may be used as the dendritic cells. In vitro methods of preparing dendritic cells from peripheral blood are known (see for example Eur. Cytokine Netw. (1995) 6(4), 245-52). In another embodiment of the present invention, JAWSII and other (ATCC, CRL-11904) mouse-derived dendritic cell lines can also be used.

Alternative to the above methods where binding of Sema3A to NP-1/Plexin-A1 heterodimer receptor-expressing cells is determined by the alkaline phosphatase activity of Sema3A-AP bound to the NP-1/Plexin-A1 heterodimer receptor, it is also possible to use dendritic cells expressing the NP-1/Plexin-A1 heterodimer receptor. In this method, Sema3A is added to cells expressing the NP-1/Plexin-A1 heterodimer receptor in a similar experiment and inhibition of cell alterations by the test substance is observed. "Cell changes" here mean changes in Rho kinase activation, intracellular myosin-II phosphorylation, and cell contraction and transmigration functions and the like.

To screen for agonists of Sema3A, changes in NP-1/Plexin-A1 heterodimer receptor-expressing cells, such as Rho kinase activation, intracellular myosin-II phosphorylation, and cell contraction and transmigration functions are compared when (i) Sema3A-AP is added and (ii) a test substance is added, or Sema3A-AP and a test substance are added to a transformant expressing the NP-1/Plexin-A1 heterodimer receptor on the cell surface. When cell changes in situation (i) are similar to those in situation (ii) when only the test substance is added, the test substance is shown to be a Sema3A agonist. When the effect of Sema3A after addition of Sema3A-AP is augmented by addition of the test substance, the test substance is also shown to be an agonist.

To screen for the antagonist described above, a transformant expressing the NP-1/Plexin-A1 heterodimer receptor on the cell surface, as well as dendritic cells isolated from peripheral blood and induced, or a dendritic cell line can preferably be used.

Specific detection methods are not particularly limited as long as they can detect the presence or absence of a signal generated by the interaction between Sema3A and an extracellular domain of the NP-1/Plexin-A1 heterodimer receptor. Sema3A binding to the NP-1/Plexin-A1 heterodimer receptor may be measured as the marker as described above. The screening method of the present method can also be accomplished by measuring cell transmigration function (see examples below), or by detecting intracellular Rho kinase activation or intracellular myosin-II phosphorylation.

A kit available from Cytoskelton (Denver, Colo., USA) (RhoA G-LISA Activation Assay colorimetric format or luminescence format, or G-LISA activation assay Biochem Kit) can be suitable used of screening based on the detection of intracellular Rho kinase activation. As a screening method based on myosin-II phosphorylation, cells expressing the NP-1/Plexin-A1 heterodimer receptor may be stained with an anti-MLC (myosin light chain) antibody and anti-phospho-MLC antibody labeled with two different-colored dyes, and the images can be captured and analyzed with an image analyzer. Such methods are described in Biochem. Biophys. Res. Commun. (2008) 374(2), 356-60.

The assay can also be performed as a high throughput screening (HTS) method. HTS relates to a test system in which multiple compounds are tested continuously. Preferably, the HTS system can be performed on a microplate, and may be partially or fully automated, and may be connected to a computer or other electronic device for purposes of data storage, analysis, and interpretation by bioinformatics. Preferably, the aforementioned automation may include a robot capable of manipulating multiple microplates and performing thousands of tests per day. Preferably, test compounds that are known to exhibit the desired modulating function or inhibiting function should be included in the assay as positive controls. The term HTS encompasses ultrahigh throughput screening (UHTS). Preferably, the UHTS system can be implemented with a 384-well or 1536-well microplate, a microliter or smaller or nanoliter or smaller pipetter, an improved plate reader, and a means of evaporation treatment. HTS methods are described for example in the specification of U.S. Pat. Nos. 5,876,946 and 5,902,732. Those skilled in the art can adapt such methods to HTS or UHTS systems without the need for excessive trial and error.

2) Methods Using Cell Membranes Expressing NP-1/Plexin-A1 Heterodimer Receptor

The screening of the present invention can also be performed by methods similar to those under Section 1) above using cell membranes prepared from cells expressing the NP-1/Plexin-A1 heterodimer receptor on the cell surface, instead of the whole cell. In this case, binding to the NP-1/Plexin-A1 heterodimer receptor is measured.

3) Methods Using Isolated and Purified Proteins Having Extracellular Domains of NP-1/Plexin-A1 Heterodimer Receptor The screening of the present invention can also be accomplished using a NP-1/Plexin-A1 heterodimer receptor that has been isolated and purified as above. In this case, binding to the NP-1/Plexin-A1 heterodimer receptor is also measured.

Sema3A function modulators can be screened by screening methods described above, and the test substances supplied for screening may be the anti-Neuropilin-1 antibodies, anti-NP-1/Plexin-A1 heterodimer receptor antibodies and anti-Sema3A antibodies as described above.

Domains that are important for binding between Sema3A and NP-1 have been identified in experiments of interactions between Sema3A and NP-1 associated with nerve axon induction. Based on the fact that polyclonal antibodies obtained using a polypeptide fragment comprising amino acids Nos. 265 (Leu) to 857 (Ile) of the NP-1 polypeptide encoded by SEQ ID NO:2 as the antigen show neutralization activity (He Z et al., Cell (1997) 90, 739-51), a Sema3A functional antagonist can preferably be obtained from anti-NP-1 antibodies that bind to a polypeptide consisting of amino acids Nos. 265 (Leu) to 857 (Ile) of the NP-1 polypeptide.

Since a polyclonal antibody obtained using a polypeptide comprising amino acids Nos. 363 (Asn) to 381 (Cys) of the Sema3A polypeptide encoded by SEQ ID NO:1 exhibited neutralization activity (Luo Y et al., Cell (1993) 75, 217-27), a Sema3A functional antagonist can preferably be obtained from anti-Sema3A antibodies that bind to a polypeptide consisting of amino acids Nos. 363 (Asn) to 381 (Cys) of the Sema3A polypeptide.

In addition to the anti-Neuropilin-1 antibodies, anti-NP-1/Plexin-A1 heterodimer receptor antibodies and anti-Sema3A antibodies as described above, an organic or inorganic chemical, a biological molecule, or a composition may be used as a test substance subjected to the screening. The most desirable modulators are molecules with limited toxicity since they must be capable of being administered as therapeutic agents. However, toxicity of the compound can be tested by another, subsequent assay, and can be "excluded by design" by a pharmaceutical chemist. Screening may be carried out using a natural extract library or chemical library maintained historically by a pharmaceutical company, or a combinatorial library, peptide library or the like.

Design of Sema3A Function Modulator

In addition to the screening methods described above, a Sema3A function modulator can be designed that comprises soluble Neuropilin-1 (NP-1), or in other words a polypeptide comprising the extracellular domains of NP-1 necessary for binding to Sema3A. A polypeptide having the extracellular domains of NP-1 necessary for binding to Sema3A and derivatives prepared from the polypeptide can be used as a function modulator.

Preferred examples of soluble Neuropilin-1 (NP-1), or in other words the extracellular domains of NP-1 necessary for binding to Sema3A, include a polypeptide consisting of amino acids Nos. 23 (Arg) to 589 (Thr) of the NP-1 polypeptide represented by SEQ ID NO:2, and a polypeptide consisting of amino acids Nos. 23 (Arg) to 857 (Ile) of the NP-1 polypeptide represented by SEQ ID NO:2. Moreover, for the object of the present invention, a polypeptide comprising the amino acid sequences of the polypeptide in which one or more amino acids are deleted, added or substituted while maintaining binding activity between Plexin-A1 and Sema3A can also be used. Amino acid residues that are necessary for maintaining binding activity with Sema3A, and methods of specifying such residues, are described in, for example, Gu C et al., (2002) 277(20), 18069-76, and can be designed appropriately based on the information in the reference.

In addition, substitutions with maintaining the function and immunological identity of a polypeptide may be accomplished by selecting substituents which are substantially different in terms of these effects while maintaining (a) the structure (sheet or spiral arrangement for example) of the polypeptide framework of the regions adjacent to the substituted amino acids, (b) the charge or hydrophobicity of the target site, or (c) the size of the side chain. Naturally occurring residues can be classified into groups based on their common side chain characteristics:

(i) hydrophobic: Norleucine, met, ala, val, leu, ile;
(ii) neutral hydrophilic: cys, ser, thr;
(iii) acidophilic: asp, glu;
(iv) basic: asn, gln, his, lys, arg;
(v) residues affecting chain orientation: gly, pro; and
(vi) aromatic: trp, tyr, phe.

Non-conservative substitutions require that a member of one of these classes be replaced with a member of another class. Such a substituted residue can be introduced into a conservative substitution site, or preferably a remaining (non-conservative) site. Mutations can be prepared using well known methods in the art, such as oligonucleotide-mediated (site-specific) mutagenesis, alanine scanning, PCR mutagenesis (Carter et al., Nucl. Acids Res. (1986) 13, 4331; Zoller et al., Nucl. Acids Res. (1987) 10, 6487), cassette mutagenesis (Wells et al., Gene (1985), 34, 315), limited selection mutagenesis (Wells et al., Philos. Trans. R. Soc. London SerA (1986) 317, 415) and the like. Mutant DNA can be prepared by engineering the cloned DNA by known techniques.

The present invention also provides a polypeptide encoded by a polynucleotide that hybridizes under high stringent conditions with a polynucleotide sequence encoding a polypeptide consisting of amino acids Nos. 23 (Arg) to 589 (Thr) of the NP-1 polypeptide represented by SEQ ID NO:2 or a polypeptide consisting of amino acids Nos. 23 (Arg) to 857 (Ile) of the NP-1 polypeptide represented by SEQ ID NO:2, which are polypeptides having binding activity with Plexin-A1 and Sema3A.

Desirable examples of such derivatives include those having a sugar chain or polyethylene glycol (PEG) chain added to the polypeptide in order to increase the stability of the polypeptide in vivo, those comprising D-amino acids for at least part of the amino acids constituting the polypeptide, and fused polypeptides comprising an Fc sequence of the constant region of the antibody fused in-frame to a carboxyl terminal or amino terminal of an extracellular domain of NP-1 necessary for binding to Sema3A.

By adding a sugar chain or PEG chain, making a fused polypeptide with Fc, or introducing D-amino acids for at least part of the amino acids constituting the polypeptide, the polypeptide having the extracellular domains of NP-1 that are necessary for binding with Sema3A will become more resistant to peptidase degradation, and extends its half-life in vivo. A "derivative" of the present invention may be one having such known modifications for purposes of in vivo stabilization while maintaining its therapeutic or preventative activity against cellular immune disease. The term "derivative" as used in the specification and in the Claims encompasses those with modifications introduced to enhance the in vivo stabilization, unless it is clear from the context that it is not the case.

Sugar chain additions to polypeptides are well known and are described in, for example, Sato M. et al., J. Am. Chem. Soc. (2004), 126(43), 14013-22 and Sato M., Angew Chem. Int. Ed. Engl. (2004), 43(12), 1516-20. A sugar chain can be attached to the N-terminus, the C-terminus or any amino acid residues between them, but is preferably attached to the N-terminus or C-terminus so as not to interfere with the polypeptide activity. The number of chains added is preferably one or two, or more preferably one. A sugar chain is preferably a monosaccharide to tetrasaccharide chain, or more preferably a disaccharide or trisaccharide. A sugar chain can be attached to a free amino group or carboxyl group on the polypeptide, either directly or via a spacer structure such as a $C_{1-10}$ methylene chain or the like.

Additions of PEG chains to polypeptides are also well known and are described for example in Ulbricht K. et al., Clin. Nephroi. (2006) 65(3), 180-90 and Dharap S S et al., Proc. Natl. Acad. Sci. USA (2005), 102(36), 12962-7 and the like. A PEG chain can be attached to the N-terminus, the C-terminus or an amino acid residues between them, and typically one or two PEG chains are attached to a free amino group or a carboxyl group on the polypeptide. The molecular weight of the PEG chain is not particularly limited, but is typically about 3000 to 7000, or preferably about 5000.

Fc to be fused with a polypeptide comprising the extracellular domains of NP-1 necessary for binding to Sema3A is a heavy chain part of a constant domain of the antibody produced by digestion with trypsin enzyme. More specifically, in the case of antibody Fc from humans, it may be but not limited to a polypeptide having an amino acid sequence represented by SEQ ID NO:7, 8, 9 or 10.

For example, it is known in the art that the Fc sequence of an IgG1-type antibody at the amino acids Nos. 233, 234, 235, 236, 327, 330 and/or 331 (based on EU numbering) is substituted with the corresponding sequence of IgG2-type or IgG4-type to modify the characteristics of the IgG1-type antibody such that it does not bind to a Fcγ receptor (WO 99/58572). There are also well-known techniques for lowering the isoelectric point of an IgG1-type antibody to improve retention in blood, reducing its immunogenicity, and improving binding to FcRn by modifying amino acid residues in the Fc sequence of the IgG1-type antibody (WO 2009072604). Moreover, techniques for lowering the heterogeneity of an IgG2-type antibody, lowering its immunogenicity and improving stability under acidic conditions by modifying amino acid residues in the Fc sequence of the IgG2-type antibody are also known. Also techniques for lowering the heterogeneity of an IgG4-type antibody, lowering its binding to a Fcγ receptor, and improving its stability under acidic conditions by modifying amino acid residues in the Fc sequence of the IgG4-type antibody are known (WO 2009041613). In the present invention, soluble Neuropilin-1 derivatives include fused polypeptides of soluble Neuropilin-1 with modified Fc, which comprises the amino acid sequences of SEQ ID NOS:7, 8, 9 and 10 and is modified to confer characteristics such as non-binding to the Fcγ receptor, retention in blood, decreased immunogenicity, improved binding activity with FcRn, and improved stability under acidic conditions described above.

Pharmaceutical Composition

The present invention may also include a pharmaceutical composition comprising a polypeptide or antibody of the present invention, together with a pharmacologically acceptable carrier. For example, a pharmaceutical composition may comprise a protein or polypeptide having a desired biological activity. Examples of such proteins include abrin, lysine A, and *Pseudomonas* exotoxin, diphtheria toxin and other toxins; tumor necrosis factors, α-interferon β-interferon, nerve growth factor, platelet-derived growth factor, tissue plasminogen activator, thrombotic compounds or anti-angiogenic compounds, and angiostatins, endostatins and other proteins for example; or lymphokines, interleukin-1 ("IL-1"), interleukin-2 ("IL-2"), interleukin-4 ("IL-4"), interleukin-6 ("IL-6"), granulocyte macrophage colony stimulation factor ("GM-CSF") or granulocyte colony stimulation factor ("G-CSF") for example; and other growth factors or other biological response modulators.

For therapeutic purposes, the polypeptide or antibody of the present invention and a pharmacologically acceptable carrier are administered to a patient at a therapeutically effective dose. The combination of the therapeutic molecule of the present invention and the pharmacologically acceptable carrier is said to be administered at a "therapeutically effective dose" when the administered amount is physiologically significant. An active substance is physiologically significant when detectable changes in the physiological function of a patient are observed. For example, an active substance used to treat a cellular immune disease is physiologically significant if the cellular immune disease response is alleviated.

A pharmaceutical composition comprising a polypeptide or antibody of the present invention can be provided in liquid form, as an aerosol or in solid form. Examples of liquid forms are injectable solutions and oral suspensions. Typical solid forms include capsules, tablets, and controlled-release forms. Examples of the last one are mini osmotic pumps and implants (Bremer et al., Pharm. Biotechnol. (1997) 10, 239; Ranade: "Implants in Drug Delivery", Drug Delivery Systems, Ranade and Hollinger (Eds.), pp. 95-123 (CRC Press 1995); Bremer et al.: "Protein Delivery with Infusion Pumps", Protein Delivery: Physical Systems, Sanders and Hendren (Eds.), pp. 239-254 (Plenum Press 1997); Yewey et al.: "Delivery of Proteins from a Controlled Release Injectable Implant", Protein Delivery: Physical Systems, Sander and Hendren (Eds.), pp. 93-117 (Plenum Press 1997)).

A liposome provides a means for delivering a therapeutic polypeptide to a subject intravenously, intraperitoneally, intrathecally, intramuscularly, subcutaneously, or by oral administration, inhalation, or intranarial administration. Liposome is a microscopic vesicle consisting of one or more lipid bilayers surrounding a water-soluble fraction (in general, see Bakker-Woudenberg et al., Eur. J. Clin. Microbiol. Infect. Dis. 12 (1993) (Addendum 1): S61; Kim, Drugs (1993) 46:618; and Ranade, "Site-Specific Drug Delivery Using Liposomes as Carriers", Drug Delivery Systems, Ranade and Hollinger (Eds.), pp. 3-24 (CRC Press 1995)). A liposomes is similar in composition to the cell membrane, and is therefore safe to administer and biodegradable. Depending on the preparation method, a liposome may be of single layer or multiple layers, and may be of various sizes, ranging from 0.02 μm to above 10 μm in diameter. Various active substances can be encapsulated in a liposome. Hydrophobic active substances are distributed in the bilayer, while hydrophilic active substances are distributed in the inner water-soluble space (see for example Machy et al., Liposomes in Cell Biology and Pharmacology (John Libbey 1987) and Ostro et al., American J. Hosp. Pharm. (1989) 46:1576). By changing the liposome size, number of bilayers, lipid composition, and the charge and surface characteristics of the liposome, it is possible to regulate the therapeutic effectiveness of the encapsulated active substance.

Antibodies, antibody fragments, carbohydrates, vitamins, transport proteins and various other targeting ligands can also be attached to the surface of liposomes. For example, a liposome can be modified with branched galactosyllipid derivatives and targeted at asialoglycoprotein (galactose) receptors, which are expressed solely on the surface of liver cells (Kato and Sugiyama, Crit. Rev. Ther. Drug Carrier Syst. (1997) 14, 287; Murahashi et al., Biol. Pharm. Bull. (1997) 20, 259). Similarly, Wu et al., (Hepatology (1998) 27, 772) show that when a liposome is labeled with asialofetuin, the plasma half-life of the liposome is reduced, and uptake of the asialofetuin-labeled liposome by liver cells is greatly increased. On the other hand, liver accumulation of liposomes containing branched galactosyllipid derivatives can be inhibited by pre-administration of asialofetuin (Murahashi et al., Biol. Pharm. Bull. (1997) 20, 259). Polyalconitylated human serum albumin liposomes provide another approach to targeting liver cells with liposomes (Kamps et al., Proc. Nat'l Acad. Sci. USA (1997) 94, 11681). Moreover, U.S. Pat. No. 4,603,044 (Geho et al.) describes a liposome vesicle delivery system targeting liver cells, and having specificity for a hepatobiliary tract receptor associated with special metabolic cells of the liver.

Polypeptides and antibodies can be encapsulated in a liposome using standard techniques of protein microcapsulation (see for example Anderson et al., Infect. Immun. (1981) 31, 1099; Anderson et al., Cancer Res. (1990) 50, 1853; Cohen et al., Biochim. Biophys. Acta (1991) 1063, 95; Alving et al.: "Preparation and Use of Liposomes in Immunological Studies", Liposome Technology, 2nd Edition, Vol. 3, Gregoriadis (Ed.), p. 317 (CRC Press 1993); and Wassef et al., Meth. Enzymol. (1987) 149, 124). As discussed above, a therapeutically useful liposome may contain various components. For example a liposome may contain a lipid derivative of poly(ethylene glycol) (Allen et al., Biochim. Biophys. Acta (1993) 1150, 9).

Degradable polymer microspheres have been designed to maintain a high systemic level of a therapeutic protein. Microspheres are prepared from degradable polymers such as poly(lactide-co-glycolide) (PLG), polyanhydrides, poly (orthoesters), non-biodegradable ethyl vinyl acetate polymer and the like, with the protein being enclosed in the polymer (Gombotz and Pettit, Bioconjugate Chem. (1995) 6, 332; Ranade: "Role of Polymers in Drug Delivery", Drug Delivery Systems, Ranade and Hollinger (Eds.), pp. 51-93 (CRC Press 1995); Roskos and Maskiewicz: "Degradable Controlled Release Systems Useful for Protein Delivery", Protein Delivery: Physical Systems, Sanders and Hendren (Eds.), pp. 45-92 (Plenum Press 1997); Bartus et al., Science (1998) 281, 1161; Putney and Burke, Nature Biotechnology (1998) 16, 153; and Putney, Curr. Opin. Chem. Biol. (1998) 2, 548). Nanospheres coated with polyethylene glycol (PEG) can also provide a carrier for intravenous administration of therapeutic proteins (see for example Gref et al., Pharm. Biotechnol. (1997) 10, 167).

Other dosage forms can be devised by those skilled in the art, as shown for example in Ansel and Popovich, Pharmaceutical Dosage Forms and Drug Delivery Systems, 5th Edition, (Lea & Febiger 1990), Gennaro (Ed.), Remington's Pharmaceutical Sciences, 19th Edition (Mack Publishing Company 1995), and Ranade and Hollinger, Drug Delivery Systems (CRC Press 1996).

Pharmaceutical compositions can be provided as a kit comprising a container comprising an anti-NP-1 antibody, an anti-NP-1/Plexin-A1 heterodimer receptor antibody and an anti-Sema3A antibody as well as an NP-1 derivative. A therapeutic polypeptide can be provided in the form of an injection solution for single or multiple administration, or as a sterile powder to be dissolved before injection. Such a kit may also comprise a dry powder dispersion device, liquid aerosol-generating device or nebulizer for administering the therapeutic polypeptide. Such a kit may also comprise written information regarding indications and methods of using the pharmaceutical composition.

Pharmaceutical compositions comprising an anti-NP-1 antibody, an anti-NP-1/Plexin-A1 heterodimer receptor antibody, an anti-Sema3A antibody and an NP-1 derivative can be provided in liquid, aerosol or solid form. Examples of liquid forms are injection solutions, aerosols, drops, topological liquids and oral suspensions. Typical solid forms include capsules, tablets, and controlled-release forms. Examples of the last one are mini osmotic pumps and implants (Bremer et al., Pharm. Biotechnol. (1997) 10, 239; Ranade: "Implants in Drug Delivery", Drug Delivery Systems, Ranade and Hollinger (Eds.), pp. 95-123 (CRC Press 1995); Bremer et al., "Protein Delivery with Infusion Pumps", Protein Delivery: Physical Systems, Sanders and Hendren (Eds.), pp. 239-254 (Plenum Press 1997); Yewey et al., "Delivery of Proteins from a Controlled Release Injectable Implant", Protein Delivery: Physical Systems, Sander and Hendren (Eds.), pp. 93-117 (Plenum Press 1997)). Other solids forms include creams, pastes, and other topical applications.

Therapeutic Applications of Anti-NP-1 Antibodies, Anti-NP-1/Plexin-A1 Heterodimer Receptor Antibodies, Anti-Sema3A Antibodies and NP-1 Derivatives Anti-NP-1 antibodies, anti-NP-1/Plexin-A1 heterodimer receptor antibodies, anti-Sema3A antibodies and NP-1 derivatives are believed to be useful for treating and preventing autoimmune diseases, allergic diseases and other cellular immune diseases because they inhibit binding between NP-1 or the NP-1/Plexin-A1 heterodimer receptor and Sema3A. The antagonistic activity and binding activity of the anti-NP-1 antibodies, anti-NP-1/Plexin-A1 heterodimer receptor antibodies, anti-Sema3A antibodies and NP-1 derivatives of the present invention can be analyzed by measuring Rho kinase activity, Myosin-II phosphorylation activity and actomyosin contractions in dendritic cells, or by measuring dendritic cell transmigration, or by other biological assay methods described herein.

A therapeutically effective dose of an anti-NP-1 antibody, anti-NP-1/Plexin-A1 heterodimer receptor antibody, anti-Sema3A antibody or NP-1 derivative is the amount of the antibody that is effective in preventing, delaying, reducing or inhibiting symptoms or biological activity associated with disease or damage upon administrated to a subject. Administration may comprise single administration or multiple administrations, and the agent can be administered in combination with another pharmaceutical composition.

Autoimmune Diseases

In more detail, organ-specific autoimmune diseases include various forms of anemia (aplastic anemia, hemolytic anemia, autoimmune hemolytic anemia, idiopathic thrombocytopenia), autoimmune hepatitis, iridocyclitis, scleritis, uveitis, orchitis, idiopathic thrombocytopenia purpura, Basedow's disease, Hashimoto's thyroiditis, juvenile-onset diabetes, which results from destruction of the β cells of the islets of Langerhans in the pancreas, inflammatory bowel disease, Addison's disease, which results from damage to the adrenal cortex, demyelinating encephalitis, multiple sclerosis and the like.

Systemic autoimmune diseases include atopic dermatitis, chronic rheumatoid arthritis or other arthritis, system lupus erythematosus (SLE), Sjogren's syndrome, undifferentiated connective tissue disease, antiphospholipid syndrome, various forms of vasculitis (polyarteritis nodosa, allergic granulomatosis and angitis), Wegener's granulomatosis, Kawasaki disease, hypersensitive angitis, Henoch-Schonlein purpurea, Behcet's disease, Takayasu's arteritis, giant cell arteritis, thromboangitis obliterans, polymyalgia rheumatica, essential (mixed) cryoglobulinemia, psoriasis, psoriasis vulgaris and psoriatic arthritis, diffuse fascitis with or without eosinophilia, recurrent panniculitis, recurrent polychondritis, lymphomatoid granulomatosis, erythema nodosum, ankylosing spondylitis, Reiter's syndrome, and various forms of inflammatory dermatitis.

A more broad-ranging list of disorders includes undesirable immune responses and inflammations, hepatic fibrosis, cirrhosis of the liver or other liver diseases, thyroiditis or other thyroid diseases, glomerular nephritis or other kidney and urological diseases, otitis or other ear, nose and throat diseases, dermatitis or other skin diseases, periodontal disease or other dental diseases, testicular inflammation, orchitis and orchitis/epididymitis, infertility, testicular trauma or other immune-associated testicular diseases, placental dysfunction, placental failure, recurrent miscarriage, eclampsia, pre-eclampsia and other immune and/or inflammation-associated gynecological diseases, posterior uveitis, intermediate uveitis, anterior uveitis, conjunctivitis, chorioretinitis, uveoretinitis, optic neuritis, intraocular inflammations such as retinitis or cystoid macular edema, sympathetic opthalmia, scleritis, retinitis pigmentosa, immune and inflammatory components of degenerative fundus disease, inflammation accompanying autoimmune disease, symptoms or disorders in which immune and/or inflammatory suppression is beneficial in the central nervous system (CNS) and other organs, Parkinson's disease, complications and/or side-effects of Parkinson's disease treatment, HIV encephalopathy complicated by AIDS-related dementia, Devic disease, Sydenham chorea, Alzheimer's disease and other CNS degenerative diseases, symptoms or disorders, inflammatory components of cerebral infarction, post-polio syndrome, immune and inflammatory components of mental disorders, spinal inflammation, encephalitis, subacute sclerosing panencephalitis, encephalomyelitis, acute neurological disorders, subacute neurological disorders, chronic neurological disorders, Guillan-Barre syndrome, pseudotumor cerebri, Down's syndrome, Huntington's disease, amyotrophic lateral sclerosis, inflammatory components of CNS compression, CNS damage or CNS infection, inflammatory components of muscular atrophy or muscular dystrophy, and immune and inflammatory-associated diseases, symptoms and disorders of the central nervous system and peripheral nervous system.

Allergic Diseases

A composition and method comprising a Neuropilin-1-Fc, NP-1 neutralizing antibody, Sema3A neutralizing antibody or other inhibitor of binding between NP-1 and Sema3A provided by the present invention can be used for treating allergic diseases including delayed (also referred to as Type IV) allergic diseases. Delayed (Type IV) allergic diseases include metal dermatitis, contact dermatitis, allergic contact dermatitis, Sjogren's syndrome, infectious allergy, drug-induced pneumonia or Guillan-Barre syndrome.

Contact Dermatitis

Allergic contact dermatitis is defined as a T-cell immune reaction to an antigen that contacts the skin. Because allergen-dependent T-cell responses are largely limited to CLA+ cell populations, it is believed that CLA+ T-cell clusters are involved in the onset of dermatitis (Santamaria-Babi, L. F., et al., J. Exp. Med. (1995) 181, 1935). Recent data have shown that it is only the memory (CD45RO+) CD4+ CLA+ T-cells, not CD8+ T-cells, that proliferate in response to nickel (a common contact hypersensitivity allergen) and produce both Type 1 (IFN-γ) cytokines and Type 2 (IL-5) cytokines. Moreover, cells that express CLA in combination with CD4, CD45RO (memory) or CD69 proliferate after nickel-specific stimulation, and express chemokine receptors CXCR3, CCR4 and CCR10 but not CCR6 (see Moed H. et al., Br. J. Dermatol. (2004) 51, 32).

It has been proven in animal models that allergic contact dermatitis is T-cell dependent, and that allergy responsive T-cells migrate to sites of allergen application (see in general Engeman T. M. et al., J. Immunol. (2000) 164, 5207; Feguson T. A. and Kupper T. S., J. Immunol. (1993) 150, 1172; and Gorbachev A. V. and Fairchild R. L., Crit. Rev. Immunol. (2001) 21, 451).

Atopic Dermatitis

The incidence of atopic dermatitis (AD), an inflammatory skin condition that recurs chronically, has increased dramatically in the past 10 years. Clinically, AD exhibits a chronic pattern of recurrence, characterized by severe itching and often by scraped-off patches and papular rash. Diagnosis of AD is mainly based on major clinical findings and minor clinical findings (see Hanifin J. M., Arch. Dermatol (1999) 135, 1551). Histopathology shows spongiosis, hyperparakeratosis, and localized parakeratosis in acute lesions, while hyperparakeratosis, parakeratosis, acanthosis/hypergranulosis and obvious epidermal hyperplasia with perivascular invasion of the dermis by lymphocytes and large quantities of mast cells are characteristics of chronic lesions.

T-cells play a central role in initiating localized immune responses in tissue, and evidence has suggested that skin-infiltrating T-cells play a particularly important role in initiating and maintaining unregulated immune responses in the skin. About 90% of infiltrating T-cells in skin inflammation sites express cutaneous lymphocyte-associated Ag (CLA+), which binds to E-selectin, an induced adhesion molecule on the endothelium (see Santamaria-Babi L. F. et al., Eur. J. Dermatol. (2004) 14, 13). A significant increase in CLA+ T-cells in circulating blood has been shown in AD patients in comparison with control individuals (see Teraki Y. et al., Br. J. Dermatol (2000) 143, 373), and other researchers have shown that CLA+ memory T-cells from AD patients respond preferentially to an allergen extract in comparison with a CLA− population (see Santamaria-Babi, L. F. et al., J. Exp. Med. (1995) 181, 1935). In humans, the cause of atopic skin disorders has been linked to an increase in $CLA^+$ T-cells expressing high levels of Th-2 cytokines similar to IL-5 and IL-13 (see Akdis M. et al., Eur. J. Immunol. (2000) 30, 3533 and Hamid Q. et al., J. Allergy Clin. Immunol. (1996) 98, 225).

When NC/Nga mice are kept at 6 to 8 weeks old under conditions with a specific pathogen (non-SPF), they spontaneously develop AD-like lesions that are similar to human AD in many respects including clinical progress, clinical signs, tissue pathology and immune pathology. On the other hand, NC/Nga mice raised under SPF conditions do not develop skin lesions. However, spontaneous skin lesions and scratching behavior can be induced simultaneously in NC/Nga mice raised in an SPF facility by injecting a natural dust mite allergen subcutaneously on a weekly basis (see Matsuoka H. et al., Allergy (2003) 58, 139). Thus, onset of AD in NC/Nga mice is a useful model for evaluating novel therapeutic substances for treating AD.

In addition to NC/Nga models of spontaneous AD, mouse skin sensitization with OVA can also be used as a model for inducing antigen-dependent epidermal thickening and dermal thickening with a mononuclear infiltrate in the skin of sensitized mice. In this case a simultaneous increase in the serum levels of total IgE and a specific IgE is generally observed, but pruritis and functional failure of the skin barrier do not occur in this model (see Spergel J. M. et al., J. Clin. Invest. (1998) 101, 1614). This protocol can be modified in order to induce pruritis and accommodative failure of the skin barrier by sensitizing DO 11.10 OVA TCR transgenic mice with OVA. When the number of antigen-specific T-cells that recognize the sensitizing antigen is increased, the inflammation level of the skin increases, and visible scratching behavior and lichenification/desquamation of the skin may be induced.

Arthritis

Deforming arthritis, rheumatoid arthritis, and arthritis encompassing joints that have become arthritic due to injury are common inflammatory conditions that are thought to benefit from the therapeutic use of anti-inflammatory antibodies and binding polypeptides. For example, rheumatoid arthritis (RA) is a systemic disease affecting the entire body, and is one of the most common forms of arthritis. It is characterized by inflammation of the membranes covering the insides of the joints, causing pain, stiffness, heat sensations, redness and swelling. Inflammatory cells release enzymes that may digest bone and cartilage. As a result of rheumatoid arthritis, the inner layer or synovium of an inflamed joint infiltrates and damages bone and cartilage, and can cause joint deterioration and severe pain along with other physiological effects. The affected joints loss their shape and alignment, and pain and decreased migration may result.

Rheumatoid arthritis (RA) is an immune-mediated disorder that causes severe disability and increased death rates, and is especially characterized by inflammation and subsequent tissue damage. Various cytokines are produced locally in rheumatic joints. Various studies have shown that two prototype inflammation-inducing cytokines, IL-1 and TNF-α, play important roles in mechanisms associated with synovial inflammation and advanced joint damage. In fact, when inhibitors of TNF-α and IL-1 are administered to RA patients, there was dramatic improvement in biological signs and clinical signs of inflammation, and a reduction in radiological signs of bone erosion and cartilage damage. Despite these promising results, however, a large percentage of patients do not respond to these active substances, so it has been suggested that other mediators are also involved in the pathophysiology of arthritis (Gabay, Expert. Opin. Biol. Ther. (2002) 2, 2, 135-149).

A number of animal models of rheumatoid arthritis are also known in the art. For example, in the collagen-induced arthritis (CIA) model, mice develop chronic inflammatory arthritis that is similar to human rheumatoid arthritis. Because CIA has immunological characteristics and pathological characteristics that are similar to those of RA, it is an ideal model for screening potential human anti-inflammatory compounds. The CIA model is a well-known mouse model that depends on both an immune response and an inflammatory response. The immune response comprises an interaction between CD4+ T-cells and B cells in response to collagen administrated as an antigen, and also causes production of anti-collagen antibodies. The inflammatory phase is the result of a tissue response caused by inflammatory mediators when some of these antibodies cross-react with the mouse's own collagen, activating a complement cascade. The advantage of using a CIA model is that the basic causative mechanisms are well known. The T-cell and B-cell associated epitopes on type II collagen have been identified, and the various immunological parameters (for example, delayed hypersensitivity and anti-collagen antibodies) and inflammatory parameters (for example, cytokines, chemokines, and matrix-degrading enzymes) associated with immune-mediated arthritis have been determined, and can be used to evaluate the effectiveness of test compounds in the CIA model (Wooley, Curr. Opin. Rheum. (1999) 3, 407-20; Williams et al., Immunol. (1992) 89, 9784-8; Myers et al., Life Sci. (1997) 61, 1861-78; and Wang et al., Immunol. (1995) 92, 8955-9).

Inflammatory Bowel Disease (IBD)

About 500,000 people in the United States suffer from inflammatory bowel disease (IBD), a disease that can attack the colon and rectum (ulcerative colitis) or both the small and large intestines (Crohn's disease). The causes of these diseases are unknown, but they are accompanied by chronic inflammation of the affected tissues. Ulcerative colitis (UC) is an inflammatory disease of the large intestine (commonly called the colon), characterized by inflammation and ulcers of the mucous membranes or innermost walls of the colon. The inflammation causes frequent elimination from the colon, resulting in diarrhea. Symptoms include loose stool, painful spasms of the adjacent abdomen, fever and weight loss. The exact causes of UC are unknown, but recent research suggests that the body's natural protective system acts against a protein in the body recognized as a foreign substance ("autoimmune reaction"). It is likely that these proteins resemble bacterial proteins in the intestines, and therefore excite or stimulate an inflammatory process that starts to destroy the inner wall of the colon. As the inner wall of the colon is destroyed, ulcers form and release mucous, pus, and blood. The disease normally starts in the rectal area, but can ultimately spread to the entire large intestine. As repeated episodes of inflammation occur, the walls of the intestine and rectum become thickened by scar tissue. Colon tissue death or blood poisoning can occur when the disease is severe. The severity of ulcerative colitis symptoms varies, and onset may be gradual or sudden. Onset may be caused by numerous factors including respiratory infection and stress.

There is presently no effective treatment method for UC, but the focus of therapy has been on suppressing the abnormal inflammatory process in the inner colon walls. Corticosteroid immune suppressants (for example azathioprine, mercaptopurine and methotrexate) and therapeutic drugs comprising aminosalicylic acid can be used to treat the disease. However, long-term use of immune suppressants such as corticosteroids and azathioprine can lead to serious side-effects including bone thinning, cataracts, infections and effects on the liver and bone marrow. In patients for whom current therapies are ineffective, surgery is an option. Surgery includes removal of the entire colon and rectum.

Animal models exist that can partially reproduce chronic ulcerative colitis. The most widely used model is the 2,4,6-trinitrobenesulfonic acid/ethanol (TNBS)-induced colitis model, which induces chronic inflammation and ulcers in the colon. When TNBS is introduced into the colons of highly sensitive mice by intrarectal drip infusion, it induces a T-cellular immune response in the mucous membranes of the colon, and a broad-ranging mucosal inflammation characterized by dense infiltration of T-cells and macrophages occurs throughout the walls of the large intestine. The histopathological disease profile accompanies a clinical profile of progressive weight loss (weakness), blood diarrhea, rectal prolapse and thickening of the large intestine walls (Neurath et al., Intern. Rev. Immunol. (2000) 19, 51-62).

Another colitis model uses dextran sodium sulfate (DSS), which induces acute colitis developing into bloody diarrhea, weight loss, colon contractions, and mucosal ulcers with neutrophil infiltration. Histologically, DSS-induced colitis is characterized by lymphoid hyperplasia, localized cryptic damage and epithelial ulcers, together with infiltration of inflammatory cells into the lamina propria. These changes stem from the toxic effects of DSS on the epithelium, and are thought to occur due to phagocytosis of the lamina propria cells and production of TNF-α and IFN-γ. Although it is commonly used, there are some problems regarding the mechanisms of DSS in human disease that have yet to be resolved. Because it is observed in SCID mice and other T-cell deficient animals, the DSS model is not considered to be T-cell dependent.

Administration of an inhibitor of binding between NP-1 and Sema3A to such a TNBS model, DSS model or CD4 introduction model can be used as a means of evaluating whether symptoms of gastrointestinal disease are alleviated and whether the progress of the disease is altered by the use of the inhibitor of binding between NP-1 and Sema3A.

Psoriasis

Psoriasis is a chronic skin disease that affects more than 7 million Americans. Psoriasis occurs when skin cells proliferate abnormally, old skin is not shed at the normal rate, inflammation occurs, and areas of bumpy, scaly skin develop. The most common form is psoriasis vulgaris, which is characterized by inflamed areas of skin ("lesions") covered with silver-white scales. Psoriasis may be limited to a few plaques, or may encompass moderate to large areas of skin, and occurs most often on the head, knees, elbows and torso. Although highly conspicuous, psoriasis is not an infectious disease spread by contact. The cause of these symptoms is related to chronic inflammation of affected tissue. The inhibitor of binding between NP-1 and Sema3A of the present invention may function as a useful therapeutic substance for reducing inflammation and pathological effects in cases of psoriasis, other inflammatory skin disease, skin allergies and mucous allergies and associated conditions.

Psoriasis is an inflammatory T-cell disorder of the skin that may cause extreme discomfort. There is no cure, and the disease may occur in people of every age. Psoriasis affects about 2% of the population in Europe and North America. Individuals suffering from mild psoriasis can often control it with topical drugs, but over a million patients throughout the world require UV therapy or systemic immunosuppression therapy. Unfortunately, ultraviolet radiation is inconvenient and risky, while many therapies are toxic and are therefore limited in duration of use. Moreover, psoriasis normally recurs, and in some cases may return to its original state soon after interruption of immunosuppression therapy. Substances that inhibit binding between NP-1 and Sema3A can be tested using a recently developed psoriasis model based on the CD4+ CD45RB introduction model (Davenport et al., Internat. Immunopharmacol. (2002) 2, 653-672).

In addition to other disease models explained in the description, the activity of an inhibitor of binding between NP-1 and Sema3A in inflamed tissue from human psoriasis lesions can be measured in vivo using a severe combined immunodeficiency (SCID) mouse model. A number of mouse models have been developed with human cells transplanted into immunodeficient mice (generally called xeno-transplantation models) (see for example Cattan A R, Douglas E, Leuk. Res. (1994) 18, 513-22 and Flavell, D J, Hematological Oncology (1996) 14, 67-82). One in vivo xenotransplantation model of psoriasis involves transplanting human psoriasis skin tissue into SCID mice, and challenge inoculating with a suitable antagonist. Other psoriasis animal models known in the art can also be used to evaluate substances that inhibit binding between NP-1 and Sema3A, such as for example transplanting human psoriasis skin grafts into an AGR129 mouse model, and challenge inoculating with a suitable antagonist (see for example Boyman, O. et al., J. Exp. Med. (2004) 199, 5, 731-736). Similarly, tissue or cells from human colitis, IBD, arthritis or other inflammatory lesions can be used in an SCID model to evaluate the anti-inflammatory properties of an inhibitor of binding between NP-1 and Sema3A as explained in the description.

Using well-known methods in the art, the effectiveness of therapy can be monitored in terms of increased anti-inflammatory effects over time in a treated group, and evaluated statistically. Some typical methods involve, but are not limited to, measuring the thickness of the epidermis, the number of inflammatory cells in the upper dermis, and the grade of parakeratosis in psoriasis. Such methods are known in the art, and are explained in the description. See for example Zeigler, M. et al., Lab. Invest. (2001) 81, 1253; Zollner, T. M. et al., J. Clin. Invest. (2002) 109, 671; Yamanaka, N. et al., Microbiol. Immunol. (2001) 45, 507; Raychaudhuri, S. P. et al., Br. J. Dermatol. (2001) 144, 931; Boehncke, W. H. et al., Arch. Dermatol. Res. (1999) 291, 104; Boehncke, W. H. et al., J. Invest. Dermatol. (2001) 116, 596; Nickoloff, B. J. et al., Am. J. Pathol. (1995) 146, 580; Boehncke, W. H. et al. (1997.) J. Cutan. Pathol. 24, 1; Sugai, J. M. et al., J. Dermatol. Sci. (1998) 17, 85 and Villadsen, L. S. et al., J. Clin. Invest. (2003) 112, 1571. It is also possible to monitor inflammation over time by a known method such as flow cytometry (or PCR), and to assay the number of inflammatory cells or damaged cells in a sample, the score for IBD (weight loss, diarrhea, rectal bleeding, length of colon), the foot disease score for a CIA RA model, and the inflammation score.

Systemic Lupus Erythematosus

Systemic lupus erythematosus (SLE) is an immune complex-associated disorder characterized by chronic IgG antibody (such as anti-dsDNA) production in response to a ubiquitous self-antigen. The effects of SLE are systemic but not localized in a specific organ. Multiple chromosomal loci are associated with the disease, and may be responsible for various aspects of the disease, including anti-dsDNA antibodies and glomerular nephritis. CD4+ T-cells have been shown to play an active role in an SLE mouse model (Horwitz, Lupus (2001) 10, 319-20; Yellin and Thienel, Curr. Rheumatol. Rep. (2000) 2, 24-37). The role of CD8+ T-cells has not been clearly defined, but there is evidence to suggest that "suppressor" CD8+ T-cell function is disabled in lupus patients (Filaci et al., J. Immunol. (2001) 166, 6452-7; Sakane et al., J. Immunol. (1986) 137, 3809-13).

As used herein, embodiments expressed with the term "comprising" encompass embodiments expressed with the term "essentially consisting of" and embodiments expressed with the term "consisting of".

All patents and reference documents that are explicitly cited in this application are incorporated herein by reference.

The present invention is explained using the following examples, but is not limited by these examples.

EXAMPLES

Example 1

Methods

Mice

Plexin-A1$^{-/-}$, Sema3K$^{-/-}$, Sema6c$^{-/-}$ and NP-1 knock-in mice with a C57BL/6 background have already been established. OT-IITg mice were provided by Mr. W. R. Heath.

For the Sema6D$^{-/-}$, a 0.6 kbp fragment comprising the second exon with start codon and the third exon were replaced with a neo resistance cassette, and a herpes simplex virus thymidine kinase (HSY-TK) gene was inserted for selecting a targeting vector from random integration. Linearized targeting plasmid DNA was transfected into embryonic stem (ES) cells by electroporation. After double selection with G418 and ganciclovir, 320 resistant clones were screened for homologous recombination of Sema6D alleles by PCR and Southern blot analysis. For the Southern blot analysis, genome DNA was isolated from wild-type and Sema6D-target ES cells and digested with EcoRI, and separated by agarose gel electrophoresis. The DNA was transferred to a nylon blotting membrane (HybondN) in accordance with the manufacturer's protocols. The filter was hybridized overnight with a radiolabeled probe. The filter was then washed for 1 hour at 65° C. with 0.1×SSC containing 0.1% SDS, and analyzed by autoradiography. Three clones having homologous recombination were identified and isolated. ES cells from three independent Sema6D mutant clones were injected separately into blastocysts from C57BL/6 mice. The blastocysts were transplanted into pseudopregnant ICR surrogate mothers, and the chimera males were then back-crossed with C57BL/6 or BALB/c females. Heterozygous mice were mated to produce homozygous mice. For purposes of immunological analysis, the homozygous mice were back-crossed for eight generations or more with C57BL/6 or BALE/c mice. The germline transmission and genotypes of the Sema6D target alleles were evaluated by Southern blotting and PCR analysis. PCR was performed in 35 cycles consisting of 60 seconds at 94° C., 60 seconds at 60° C. and 60 seconds at 72° C., using the primers (5'-acaaacgagaaaccagtttcacc-3') (SEQ ID NO:13) and (5'-ccagcaatataaagtgtgtctcg-3') (SEQ ID NO:14).

For RT-PCR analysis, RNA was isolated from spleens with RNeasykits (Qiagen) and treated with DNaseI (Invitrogen), and the genome DNA was removed. cDNAs was synthesized with a SuperScript IIc DNA synthesis kit (Invitrogen), and RT-PCR was performed in 35 cycles consisting of 30 seconds at 94° C., 30 seconds at 60° C. and 30 seconds at 72° C., using the primers (5'-caatatccggttttagaggacgcc-3') (SEQ ID NO:15) and (5'-cctgctgtctggacctccacgtcag-3') (SEQ ID NO:16). The mice were maintained in a special sterile environment, and used at the age of 8 to 12 weeks. All test procedures were in accordance with the guidelines of our organization.

Cell Culture

As described above, bone marrow-derived cells (BMDC) were produced by culturing bone marrow cells for 6 to 8 days in the presence of GM-CSF. SVEC4-10 (mouse lymphatic endothelial cell line, from ATCC) was cultured in DMEM medium containing 10% FCS. Human lymphatic microvascular endothelial cells (HMVEC-dLy, Lonza) were cultured in an Endothelial Cell Medium Bullet Kit (Lonza).

Antibodies, Reagents and Fluorescent Dyes

The following reagents were used: LPS, Oxazolone (4-ethoxymethylene-2-phenyl-2-oxazolin-5-one), FITC isomer, blebbistatin, ML-7 (Sigma), Y-27632 (Carbiochem), collagenase D (Roche), calcein AM, CFSE (5-(and 6)-carboxyfluorescein diacetate succinimidyl ester), CMFDA (5-chloromethylfluorescein diacetate), CMTMR (5-(and 6)-(((4-chloromethyl)benzoyl)amino)tetramethylrhodamine), phalloidin 488, phalloidin 546 (Invitrogen), recombinant human Sema3A-Fc, recombinant mouse GM-CSF, mouse CCL19, mouse CCL21 (R & D), mouse CXCL12, mouse TNFα (PeproTech) and mouse CD40 (HM40-3) (BD Biosciences). The following antibodies were used in immunohistochemical tests: rabbit anti-MLC, rabbit anti-phosphorylated MLC (Cell Signaling Technologies), mouse anti-B-actin (Sigma), rabbit anti-Plexin-A1 (provided by Y. Yoshida), biotinylated anti-mouse LYVE-1 (R & D), Cy3-anti-rabbit IgG (Jackson), ECL-anti-rabbit IgG-POD, ECL-anti-mouse IgG-POD, streptavidin-POD (GE Healthcare). FITC/APC-anti-CD4 (GK1.5, eBioscience), APC-Cy7-anti-CD8a (53-6.7), PE-anti-B220 (RA3-6B2), FITC/APC-anti-CD11c (HL3), FITC/PE-anti-1-A$^b$ (25-9-17, BD Biosciences), Alexa 647-anti-CCR7 (4BI2, Biolegend), Alexa 647-anti-CXCR4, anti-mouse CD49a (HA31/8), anti-mouse CD49e (5H10-27, BD Biosciences), anti-mouse CD11a (M17/4), anti-mouse CD51 (RMV-7, eBioscience), anti-mouse VLA-1 (MAB1997, Chemicon), anti-mouse CD18 (M18/2) and anti-mouse CD61 (2C9, G2, eBioscience) were used for cell staining in flow cytometry. Anti-Sema6D mAb (natsuclone) was established by immunizing Sema6D-deficient mice with a recombinant Sema6D-Fc protein.

In Vivo Monitoring of Proliferative Response of Antigen-Specific T-Cells

For the CFSE-dilution assay, CD4$^+$ T-cells isolated from OT-II mice were labeled with CFSE (Lyons and Parich, J. Immunol. Methods 1994). In brief, 10$^7$/ml of cells were incubated for 10 minutes with 1 μM of CFSE in PBS (pH 7.4). 2×10$^6$ cells were injected intravenously into a recipient mouse. After 2 hours, OVA (Grade VI, Sigma) in complete Freund's adjuvant (CFA) was injected subcutaneously into a hind foot pad to immunize the mouse. The mouse was sacrificed after 72 hours. The proliferative response of the antigen-specific T-cells in the draining lymph nodes was analyzed by flow cytometry, and shown as dilution of CFSE fluorescent intensity.

For T-cell priming, a mouse was immunized by injecting 100 μg of keyhole limpet hemocyanin (KLH) in CFA into a hind foot pad. 5 days after immunization, CD4$^+$ T-cells isolated from the draining lymph nodes were stimulated for 72 hours with various concentrations of KLH. For the proliferation assay, the cells were stimulated with 2 μCi of $^3$H-thymidine during the last 14 hours. Secretion of IL-2, IFNγ and IL-17 was measured with Cytokine Plex (Bio-Rad).

Adoptive Transfer Test

BMDC cells were labeled for 10 minutes at room temperature with 5 μM of CFSE in PBS, and washed with PBS. 1×10$^6$ DC cells in 50 μl of PBS were injected subcutaneously into a hind foot pad of a recipient mouse. Popliteal lymph nodes were collected from 24 to 48 hours after injection and treated for 30 minutes at 37° C. with 1 mg/ml of collagenase D, and the cells were counted and analyzed by flow cytometry. The percentage of migrating dendritic cells corresponds to the ratio of fluorescent dendritic cells to total lymph node cells.

Two-Photon Microscopy

BMDC cells (1×10$^6$) were pulsed with OT-II peptide, labeled with 5 μM of CMTMR, and injected into a hind foot pad of a wild-type recipient mouse. 18 hours after dendritic cell injection, 2×10$^7$ OT-IITg mouse-derived CD4$^+$ T-cells labeled with 5 μM of CMFDA were injected intravenously. Anti-CD62L antibodies were administered at 1 hour to block inflow of new T-cells into the lymph nodes through the HEV. After 10 hours, the popliteal lymph nodes were excised, and maintained at 37° C. in washing medium (superfused medium) bubbled with 95% O$_2$/5% CO$_2$. A MaiTaiTi: sapphire laser (Spectra Physics, Mountain View, Calif.) was adjusted to 875 nm for second harmonic generation and two-photon excitation of CMFDA and CMTMR. For four-dimensional analysis of cell migration, spading of seven x-y sections with a z of 5 µm were taken every 30 seconds, to produce a volume image with a depth of 30 µm in 30 minutes. Three fluorescent channels were separated using 440, 510 and 560 nm two-color mirrors in combination with 400/40 (second harmonic signal), 535/26 (CMFDA) or 600/100 (CMTMR) nm bandpass filters, and detected with a non-descanned detector using an 0.8 NA 40× submerged objective lens.

FITC Skin Painting

Emigration of epidermal dendritic cells was induced in vivo by applying 50 µl of 2 mg/ml FITC in a carrier solution (1:1 v/v acetone:dibutylphthalate) to shaved shoulders. The control animals were given the same amount of carrier solution without FITC. 24 and 48 hours later the mice were sacrificed, the brachial lymph nodes were excised, and the frequency of $CD11c^+$ $FITC^+$ dendritic cells was evaluated by flow cytometry. The number of endogenous DC cells that had migrated to the brachial lymph nodes was calculated as follows: (number of endogenous dendritic cells)=(total cell count)×(% of $CD11c^+$ $FITC^+$ cells).

Transwell Test

An uncoated Transwell (pore diameter 5.0 µm; Corning) was placed in a 24-well plate containing CCL21 or CSCL12 in 0.6 ml of RPMl containing 0.1% BSA. $1 \times 10^5$ dendritic cells in 0.1 ml of solution were added to the upper well of the Transwell, and incubated for 3 hours at 37° C. The cells in the upper chamber were ablated for 5 minutes with 5 mM PBS-EDTA, and counted by Guava. Fibronectin (10 mg/ml), type 1 collagen (3.0 mg/ml) or lymphatic endothelial cells were laid over the membrane of the top chamber for purposes of in vitro migration assay. In brief, $2 \times 10^4$ SVEC4-10 or HMVEC-dLy cells were seeded on the top or bottom surface of a Transwell insert coated with 2 µg/ml of fibronectin. After 2 days of culture, the integrity of the confluent layer was investigated by phalloidin staining. A migration assay was performed for 6 hours. Inhibition of myosin II and Rho activity in the dendritic cells was accomplished by 30 minutes of treatment at 37° C. with 50 µM blebbistatin (Sigma) or 30 µM Y-27632 (Calbiochem).

In Vivo Migration of Dendritic Cells

To observe the outflow of dendritic cells from the periphery, contact hypersensitivity was induced by application of oxazolone to the abdomen. 6 days after sensitization, oxazolone was applied to the ear. 8 hours after the challenge, $10^6$ CMFDA-labeled BMDC cells were injected through the skin. After 24 hours the animals were sacrificed, and the ear tissue was fixed with paraformaldehyde. The lymph channels were detected by whole mount staining using biotinylated anti-LYVE-1+streptavidin-Cy3. Images were obtained by confocal z-stack imaging, and the number of cells retained at the periphery was counted.

Two-Dimensional Migration Assay

To analyze the chemotaxis of dendritic cells in a Zigmond chamber, LPS-treated dendritic cells were made to adhere to a fibronectin-coated (2 µg/ml) cover slip for 30 minutes. The cover slip was placed in a Zigmond chamber, and an aliquot (0.1 ml) of a solution (RPMI containing 0.1% BSA) was added to one side of the chamber, while the same solution containing CCL21 (5 µg/ml) was added to the other side. Images were recorded every 30 seconds with an inverted confocal microscope (LSM 5 Exciter, HAL100, Zeiss) equipped with an environment chamber for temperature, humidity and $CO_2$. A Zeiss EC-plan Neofluar 20× object lens (0.5 NA) was used for imaging.

To analyze the effect of Sema3A on dendritic cell migration, a chemotaxis test was performed in an EZ-Taxiscan chamber in accordance with the manufacturer's protocols (Effector Cell Institute). EZ-Taxiscan is an optically accessible chemotaxis chamber. A chamber containing CCL21 (5 µg/ml) in one compartment and cells and recombinant Sema3A-Fc (5 µg/ml) or IgG in another compartment was connected to a microchannel. Phase contrast images of the migrating cells were taken at 30-second intervals.

Two-Dimensional Migration Assay in 3D Collagen Matrix

Bone marrow-derived dendritic cells that had been treated for 12 hours with LPS (500 ng/ml) were suspended in type I collagen (3 mg/ml) (BD Biosciences) containing 2% FCS and control IgG (5 µg/ml) or Sema3A-Fc (5 µg/ml) and cast on one side of a Zigmond chamber, and the stage was covered with gel and polymerized by 30 minutes of incubation at 37° C. Next, RPMI containing 0.5% BSA and CCL21 (5 µg/ml) was added to the other side. After 20 minutes of incubation, the migration of the dendritic cells was assessed at 1 minute intervals using a confocal time-lapse video microscope recorder as described above.

Chemotaxis Assay Analysis

To compare the migration velocities of the dendritic cells in the collagen matrix, a random sample of single cells was tracked manually using the Image J Manual Tracking Plug-in or the Metamorph offline software Track-point. The cells were tracked for 2 hours. The velocity and direction parameters were calculated, and the resulting data were analyzed for chemotaxis to obtain a visible plot. The average velocity and instantaneous velocity of migration were calculated by excluding the resting part.

Dendritic Cell-Endothelial Cell Interactions $1 \times 10^4$ BMDC cells were added to an endothelial cell monolayer derived from normal human skin lymphatic microvascular endothelial cells (HMVEC-dLy). After 30 minutes of incubation, images were recorded at 30-second intervals with an inverted confocal microscope (LSM 5 Exciter, HAL100, Zeiss) equipped with an environment chamber for temperature, humidity and $CO_2$. A Zeiss EC-plan Neofluar 20× object lens (0.5 NA) was used for imaging. $1 \times 10^4$ CFSE-labeled BMDC cells were added to the HMVEC-dLy endothelial cell monolayer for purposes of 3D imaging. After 45 minutes of incubation, the cells were fixed with 4% PFA, and stained with phalloidin Alexa 546.

Confocal microscope images were obtained with an inverted microscope (LSM 5 Exciter, Zeiss) using a Zeiss Plan-Apochromat 63× oil DIC lens (1.4 NA) with an optical section spacing (z-spacing) of 0.22 µm. Using Imaris 3D software, 12 z-stack images were reconstructed to make a three-dimensional image. To evaluate the statistical analysis, the dendritic cells were classified into two groups: DC cells that could be detected only at the tips of the endothelial cells in a confocal microscope, and dendritic cells that could be detected throughout the endothelial cells from the tips to the base. The percentage of dendritic cells that could be detected throughout the endothelial cells was calculated as a percentage of the total dendritic cells.

RT-PCR

For RT-PCR analysis, RNA was isolated from immature bone marrow-derived dendritic cells, mature dendritic cells (CD40; 1 µg/ml, TNFα; 50 ng/ml), SVEC4-10 and HMVEC-dLy using RNeasykits (Qiagen), and treated with DNaseI (Invitrogen) to remove genome DNA. cDNAs was synthesized using a SuperScript IIc DNA synthesis kit (Invitrogen).

Adhesion Assay

A 96-well dish (BD Biosciences) coated with fibronectin, laminin, type I collagen, type IV collagen and poly-L-lysine (PLL) was blocked for 30 minutes with 0.5% BSA in RPMI. $5 \times 10^4$ BMDC cells labeled with 1 µM of calcein AM were added to each well. After 30 minutes of incubation at 37° C., the plate was shaken for 15 seconds at 1100 rpm and washed 3 times with PBS. The cells were solubilized with 0.2% triton-X in PBS, and fluorescent intensity was measured at 460 nm with an Arvo (Perkin Elmer). The absorbency of a cell lysate from the total volume of the added cells was given as 100%. To determine the adhesion activity of dendritic cells to endothelial cells, $1\times10^5$ BMDC cells labeled with 1 µM of calcein AM were added to an endothelial cell monolayer in a 24-well plate. After 30 minutes of incubation at 37° C., the cells were fixed with 4% PFA, and thoroughly washed. Images were taken with a fluorescence microscope (Nikon eclipse TE2000-E) using a Nikon Plan Fluor 10×DIC objective lens (NA 0.3), and the number of adhering cells was counted with NIS-elements AR 3.0 software.

Immunohistology

LPS-treated BMDC cells ($2\times10^4$) were affixed for 30 minutes at 37° C. to fibronectin-coated glass (10 µg/ml). Non-adhering cells were removed, and the dendritic cells were incubated for 10 minutes with Sema3A-Fc (5 µg/ml) or control IgG (5 µg/ml), fixed for 30 minutes at 4° C. with 4% PFA, incubated for 1 hour with a blocking solution (30% normal goat serum, containing 2% BSA in PBS), and stained overnight with rabbit anti-Plexin-A1 or rabbit anti-pMLC with anti-rabbit Cy3 and phalloidin Alexa 488. Images were taken by confocal z-stack imaging (0.5 µm intervals) with an inverted microscope (LSM 5 Exciter, Zeiss) using a Zeiss Plan-Apochromat 63× oil DIC objective lens (1.4 NA).

ELISA Assay

BMDC cells were cultured on plates coated with sema6D-Fc (5 µg/ml) and control IgG (5 µg/ml), with or without LPS (200 ng/ml). After 48 hours of incubation, the culture supernatant was isolated, and TNFα and pro-MMP9 (R & D) were assayed by ELISA.

Analysis of Dendritic Cell Subsets in Lymph Nodes

The cervical, brachial, central, groin and popliteal lymph nodes were isolated from non-inflamed 8-week-old mice and digested for 30 minutes at 37° C. with HANKS containing 400 µ/ml of collagenase D, and single-cell suspensions were prepared from the digested tissue, stained with antibodies against CD11c, B220, CD4, CD8a and I-$A^b$, and analyzed by flow cytometry after gate setting for the CD11c$^+$ B220$^-$ population.

Statistical Analysis

If the data were found to meet the standard, a Student's t-test and one-way ANOVA were performed. In other cases, a Mann-Whitney U-test was performed. When ANOVA was significant, a Tukey test was performed as a post hoc analysis. The data were analyzed with Statce 12.

Results

Diminished Dendritic Cell Migration to Draining Lymph Nodes in Plexin-A1$^{-/-}$ Mice We reported previously that antigen-specific T-cell production is greatly diminished in Plexin-A1$^{-/-}$ mice. However, the exact role of Plexin-A1 in antigen-specific T-cell priming was unknown. To investigate the mechanisms in more detail, OT-11 cells were activated in wild-type and Plexin-A1$^{-/-}$ mice. In wild-type recipient mice, CFSE-labeled OT-11 cells proliferated well after subcutaneous administration of OVA peptide together with CFA (FIG. 1A). By contrast, the antigen-specific proliferation response was greatly diminished when OT-11T cells were injected into Plexin-A1$^{-/-}$ mice (FIG. 1A). The results show the importance of Plexin-A1 in antigen-specific T-cell responses.

Antigen-specific T-cells are stimulated by contact with dendritic cells that have been pulsed with an antigen in the draining lymph nodes. We therefore investigated the effects of Plexin-A1 deficient dendritic cells on interactions between dendritic cells and T cells in the draining lymph nodes.

To observe cell-cell contact between antigen-specific T-cells and dendritic cells that had been pulsed with antigen in the lymph nodes, wild or Plexin-A1$^{-/-}$ mouse-derived dendritic cells that had been pulsed with CMTMR-labeled OVA were injected into the foot pads of wild-type recipient mice, and the popliteal lymph nodes were analyzed by two-photon microscopy. When wild-type dendritic cells were injected into the foot pads, the CMTMR-labeled dendritic cells were distributed abundantly throughout the T-cell region of the draining lymph nodes (FIG. 1B, top). By contrast, when dendritic cells were injected almost no dendritic cells were found in the draining lymph nodes of the recipient mice (FIG. 1B, bottom), indicating that the cell migration ability was decreased.

In order to quantitatively compare the migration activity of wild-type and Plexin-A1$^{-/-}$ dendritic cells in vivo, CFSE-labeled dendritic cells were injected into the foot pads of wild-type mice, and subsequent arrival of the cells in the draining lymph nodes was investigated. The Plexin-A1$^{-/-}$ dendritic cells were shown to have decreased migration activity in comparison with the wild-type dendritic cells.

Next, the migration ability of endogenous dendritic cells was analyzed. The number of CD11c$^+$MHCII$^{hi}$ and CD11c$^+$ CD4$^-$CD8$^-$ migrating dendritic cell subsets in the draining lymph nodes of the skin in a steady state was lower in Plexin-A1$^{-/-}$ mice (FIG. 5C).

Because Plexin-A1 expression rises as dendritic cells mature, a FITC skin painting test was performed to investigate the effect of Plexin-A1 deficiency on dendritic cell trafficking under inflammation conditions. As shown in FIG. 1D, Plexin-A1$^{-/-}$ mice had significantly fewer migrating FITC-positive dendritic cells than wild-type mice.

In summary, these results show that Plexin-A1 plays a definitive role in dendritic cell trafficking, and suggest that a drop in dendritic cell trafficking is the principal reason for deficient T-cell stimulation in Plexin-A1$^{-/-}$ mice.

Figure 6A:
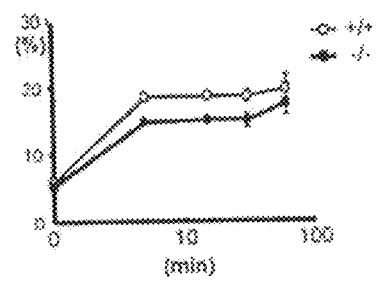
FIG. 6 shows FITC-dextran uptake and response to chemokines in Plexin-A1$^{-/-}$ dendritic cells.
Figure 6B:
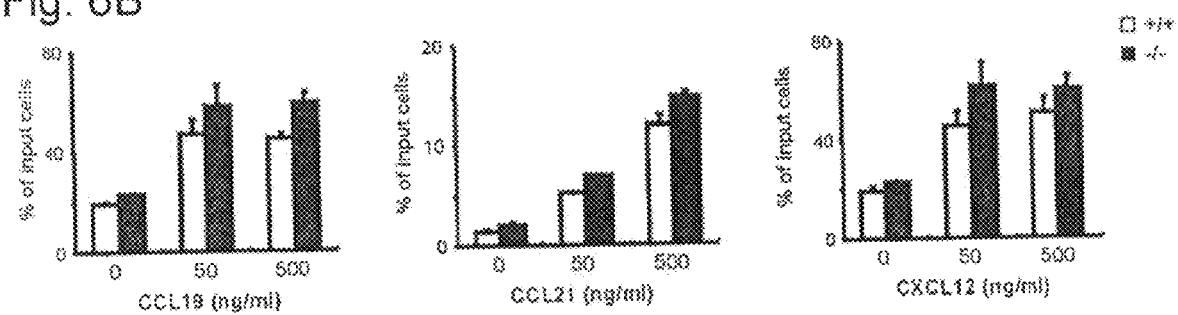
Figure 6C:
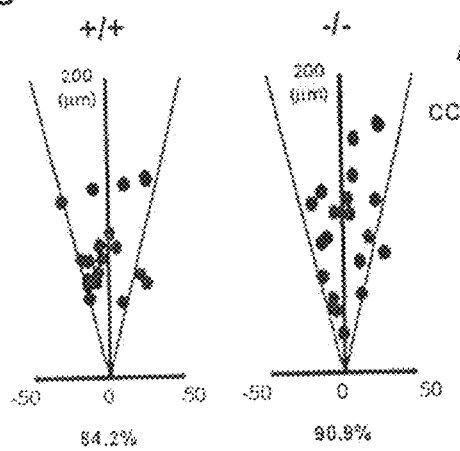
Figure 6D:
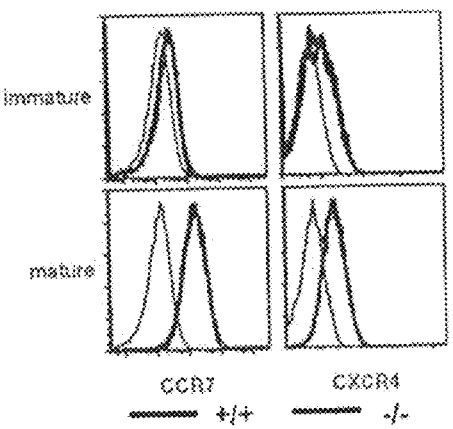

Decreased Migration Ability During Dendritic Cell Trafficking of Plexin-A1$^{-/-}$ Dendritic Cells Dendritic cell trafficking from peripheral tissue to the lymph channels occurs in a number of sequential sages, including antigen uptake, interstitial migration to lymph channels in response to chemokines, and a process of passage through the lymph channels. Each migration stage was investigated in detail to determine which stages require Plexin-A1. In terms of antigen uptake, there was no significant difference between wild-type and Plexin-A1$^{-/-}$ dendritic cells (FIG. 6A). In a Transwell assay, there was no difference in the ability of dendritic cells to migrate in response to CCL19, CCL21 or CXCL12 (FIG. 6B), and there was also no difference in the direction of sensitivity of dendritic cells in a chemokine gradient in a two-dimensional assay using a Zigmond chamber (FIG. 6C). In line with these findings, the expressed level of CCR7 and CXCR4 was similar in wild-type and Plexin-A1$^{-/-}$ dendritic cells (FIG. 6D).

These results show that Plexin-A1 is not necessary for antigen uptake or responsiveness to chemokines during migration.

Our observations suggest that Plexin-A1 plays a definitive roll in migration once these cells have reached the first lymph channel. To investigate the role of Plexin-A1 in the migration process in vivo, wild-type and Plexin-A1$^{-/-}$ dendritic cells labeled with CFSE were adoptively transferred to oxazolone-treated mice, and the fate of the transplanted dendritic cells was investigated.

As shown in FIG. 2A, 24 hours after adoptive transfer almost no wild-type dendritic cells were found around the first lymph channel in the presence of a physiological lymph stream. By contrast, numbers of Plexin-A1$^{-/-}$ dendritic cells were retained along the lymph channels of the skin in recipient mice, and the lymph channels were LYVE-1 positive (FIG. 2A). This shows that the ability to pass through lymph channels was diminished in Plexin-A1$^{-/-}$ dendritic cells.

Next, time-lapse imaging was performed to investigate whether or not Plexin-A1 deficiency in dendritic cells affects initial contact between the dendritic cells and the lymphatic endothelial cells. Wild-type dendritic cells interacted with endothelial cells at the cell-cell junctions of lymphatic endothelial cells, and transmigrated across the endothelial cells (FIG. 2B, top). However, although Plexin-A1$^{-/-}$ dendritic cells moved actively, extended their dendrites and contacted the lymphatic endothelial cells in the same way as wild-type dendritic cells, they were not able to pass through the lymphatic endothelial cells (FIG. 2B, bottom).

Figure 7:
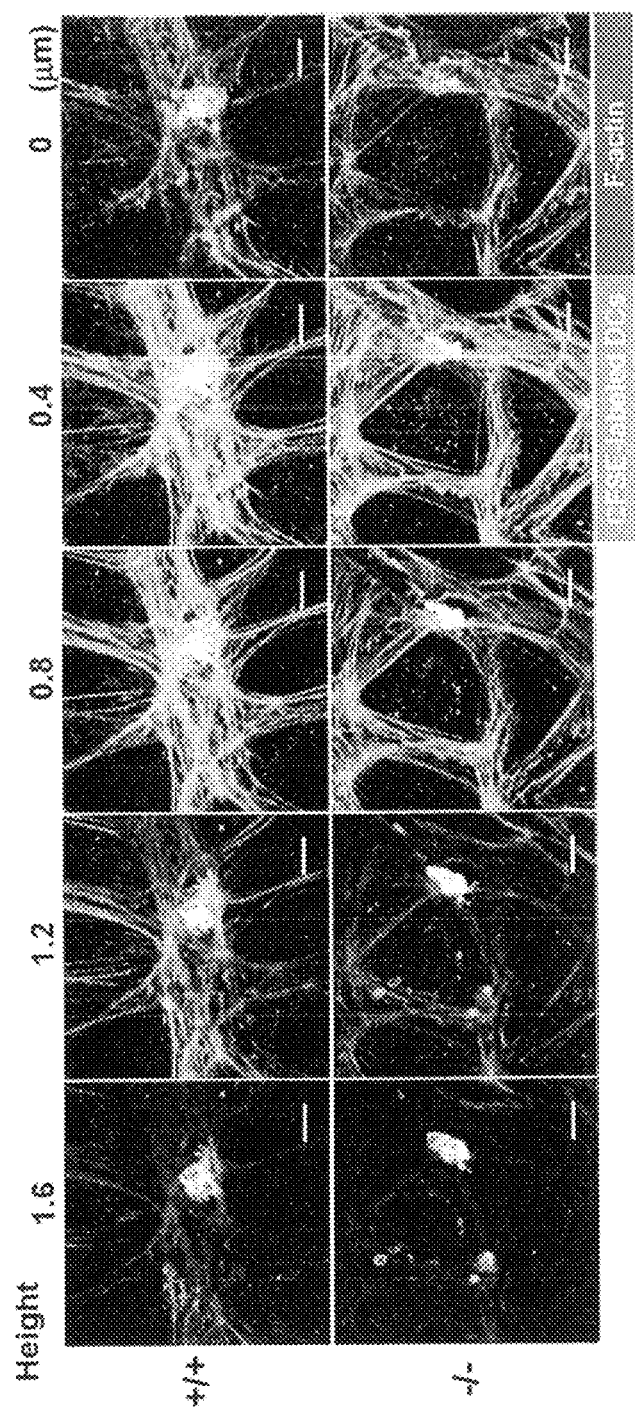
FIG. 7 shows decreased activity of dendritic cells passing through an endothelial cell monolayer in Plexin-A1$^{-/-}$ dendritic cells.

To further verify these findings, CFSE-labeled dendritic cells were applied to a monolayer of lymphatic endothelial cells, stained with the F-actin marker phalloidin, and observed by confocal z-stack imaging. The wild-type dendritic cells were observed throughout the endothelial cells, from the top to the bottom. By contrast, the Plexin-A1$^{-/-}$ dendritic cells adhered to the lymphatic endothelial cells, but were not able to pass through (FIG. 2C, FIG. 7). In a Transwell test, the ability of Plexin-A1$^{-/-}$ dendritic cells to pass through an endothelial cell monolayer was significantly lower (FIG. 2D).

In summary, these results suggest that dendritic cells strongly require Plexin-A1 for the process of passing through the lymph channels.

Figure 8:
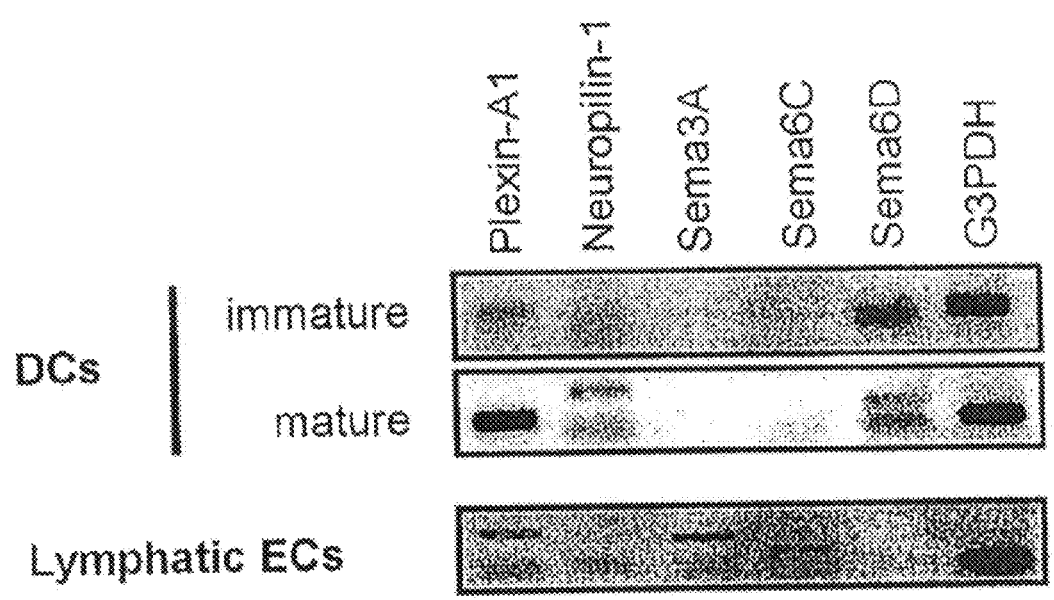
FIG. 8 shows expression profiles for Plexin-A1 and related molecules in dendritic cells and lymphatic endothelial cells.
Figure 9A:
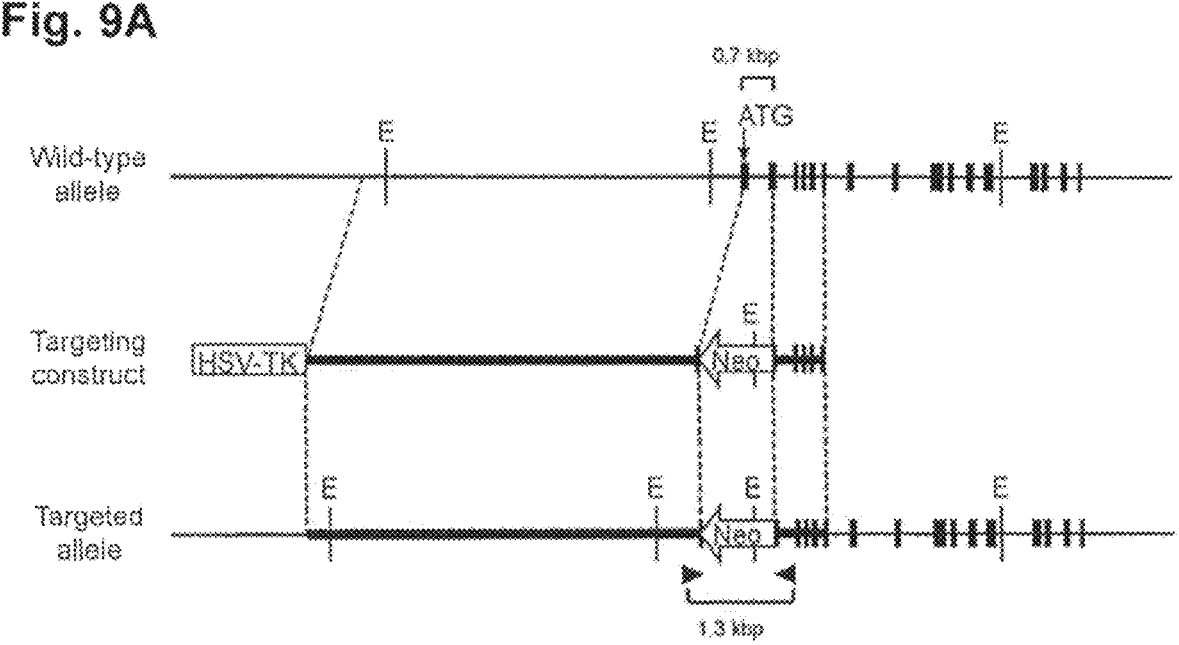
FIG. 9 shows a preparation procedure for Sema6D$^{-/-}$ mice.
Figure 9B:
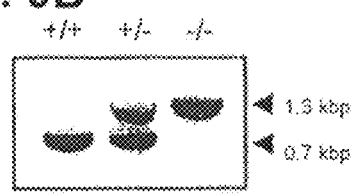
Figure 9C:
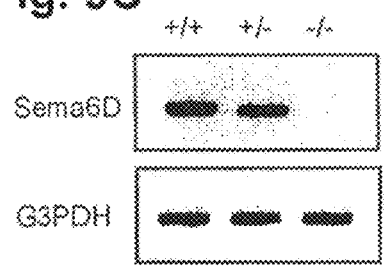
Figure 9D:
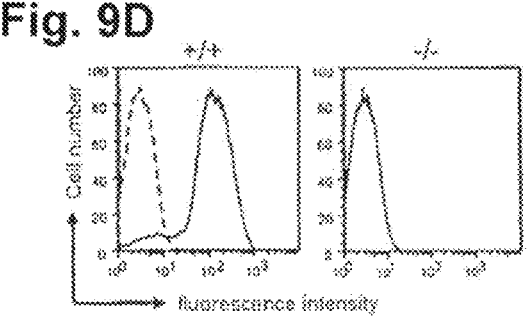

Sema3A, Rather than Sema6C or Sema6D, is Responsible for Plexin-A1-Mediated Dendritic Cell Trafficking Plexin-A1 is a receptor component for two types of semaphorins: Sema3A, a secretory class III semaphorin, and Sema6C and Sema6D, which are class VI transmembrane semaphorins. Thus, we evaluated which interaction causes the deficiency in Plexin-A1$^{-/-}$ dendritic cells. First, we investigated the expression profiles of these molecules in dendritic cells and lymph channels. The Sema3A receptor component NP-1, Plexin-A1, and Sema6D were expressed in dendritic cells, and Sema3A and Sema6C were expressed in lymph channels (FIG. 8). Based on the expression profile, an adoptive transfer assay was performed to clarify which mode is indispensable for dendritic cell trafficking. When dendritic cells from NP-1$^{sema-}$ knockout mice lacking Sema3A binding sites were introduced into wild-type recipient mice, migration to the draining lymph nodes was reduced (FIG. 3A). By contrast, dendritic cells from SEma6D$^{-/-}$ mice (FIG. 9) exhibited the same level of migration activity as those from wild-type mice (FIG. 3A). These results suggest that NP-1 expression in dendritic cells is necessary for dendritic cell trafficking.

To further investigate which semaphorin is necessary in the lymph channels, dendritic cells from wild-type mice were injected into Sema3A$^{-/-}$ recipient mice, and decreased migration of dendritic cells to the draining lymph nodes was observed (FIG. 3B). When dendritic cells from wild-type mice were introduced into Sema6C$^{-/-}$ or Sema6D$^{-/-}$ recipient mice, however, there were no abnormalities in dendritic cell trafficking (FIG. 3B). To confirm these findings in vitro, a migration assay was performed in the presence of a lymphatic endothelial cell monolayer.

As shown in FIG. 3C, dendritic cells from NP-1$^{sema-}$ knockout mice exhibited less migration ability, in the same way as dendritic cells from Plexin-A1$^{-/-}$ mice (FIG. 2D). Moreover, dendritic cells from Sema6D-1 mice exhibited no abnormalities (FIG. 3D). Next, a T-cell priming test was performed using the following Plexin-A1-related mutant mice: Sema3A$^{-/-}$, Sema6C$^{-/-}$, Sema6D$^{-/-}$ and NP-1$^{sema-}$ knockout mice. In line with the previous results, the Sema3A$^{-/-}$ and Np-1$^{sema-}$ knockout mice had the same T-cell priming deficiencies as the Plexin-A1$^{-/-}$ mice, but no antigen-specific T-cell priming abnormalities were observed in the Sema6C$^{-/-}$ or Sema6D$^{-/-}$ mice (FIG. 3D). Taken together, these results show that Sema3A, rather than Sema6C or Sema6D, is a functional ligand of Plexin-A1 in the migration process of dendritic cells to the lymph nodes.

Sema3A induces actomyosin contractions by stimulating myosin II activity. In the nervous system, Sema3A determines the direction and migration of neuronal axon guidance factors. Thus, we hypothesized that Sema3A is also associated with dendritic cell trafficking. We first investigated the localization of Plexin-A1 in migrating dendritic cells. Plexin-A1 expression is localized at the trailing edge of the migrating cells, not at the leading edge where active actin polymerization is observed (FIG. 4A). consistently, migration of dendritic cells in response to chemokines in a Transwell assay was enhanced when Sema3A was added to the upper chamber, but not when it was added to the lower chamber (FIG. 4B, left).

Figure 4B:
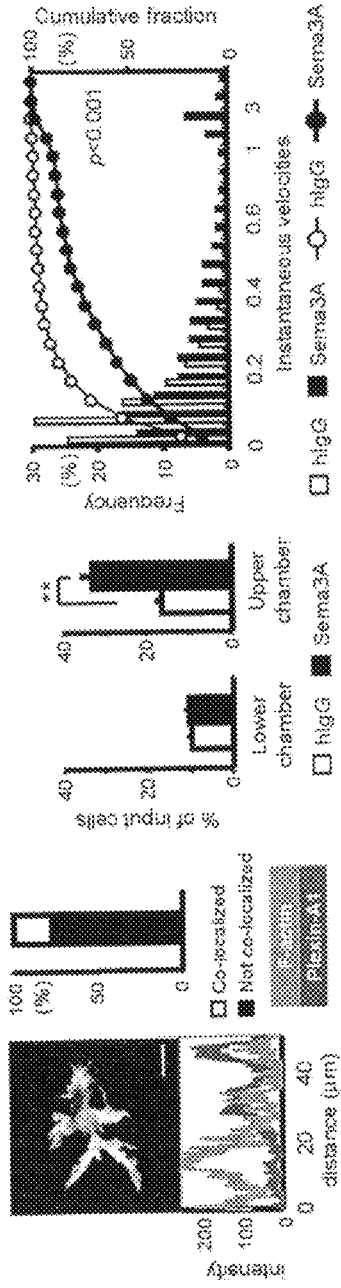

In a two-dimensional directional migration assay evaluated by EZ-taxiscan, Sema3A increased the proportion of motile dendritic cells, and increased the velocity of dendritic cells when applied against the chemokine gradient (FIG. 4B, right). This suggests the importance of Sema3A in the polarity of migrating dendritic cells.

Figure 4C:
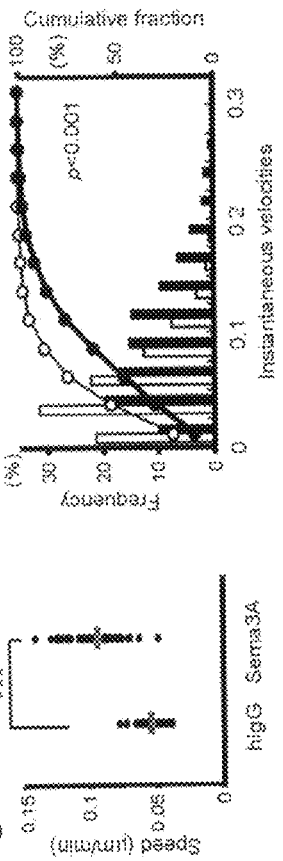
Figure 4D:
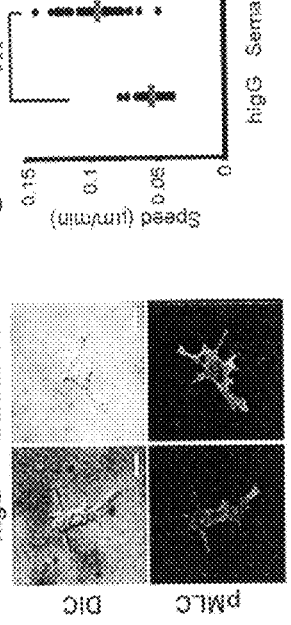
Figure 10A:
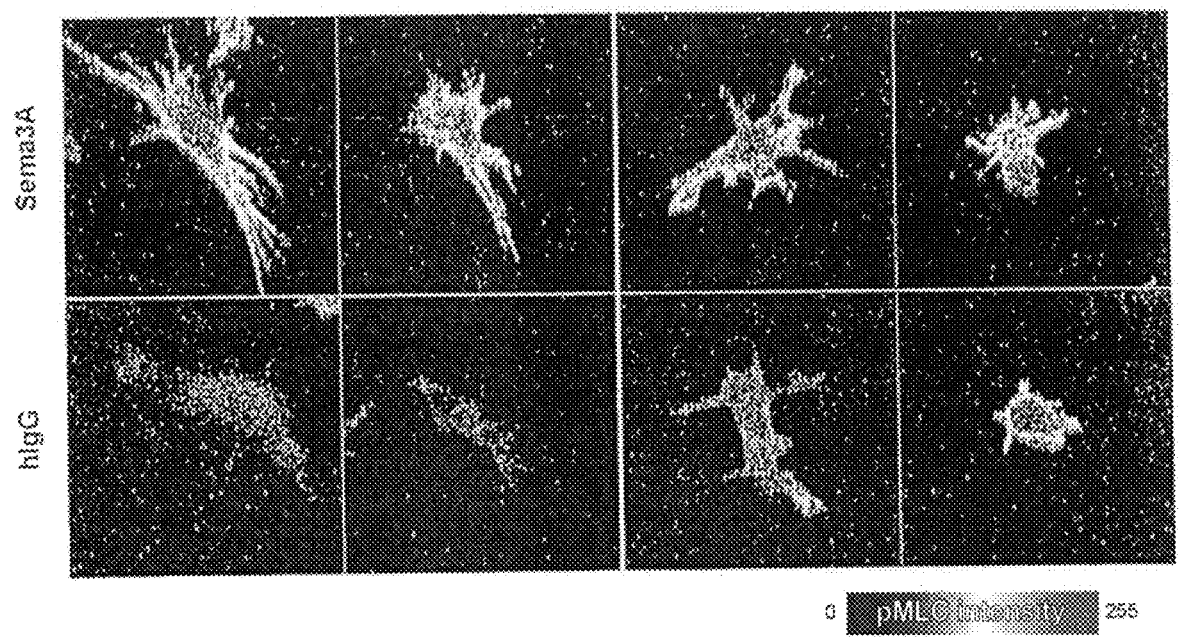
FIG. 10 shows induction of myosin light chain phosphorylation by Sema3A.
Figure 10B:
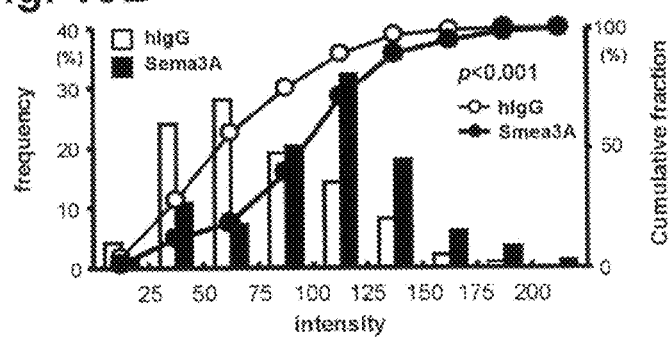
Figure 11A:
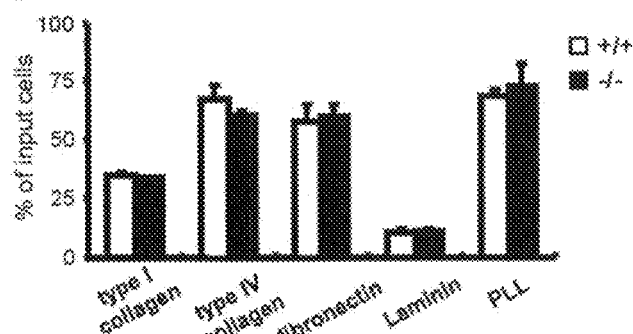
FIG. 11 shows adhesion activity and secretion of TNFα and pro-MMP9 of dendritic cells.
Figure 11B:
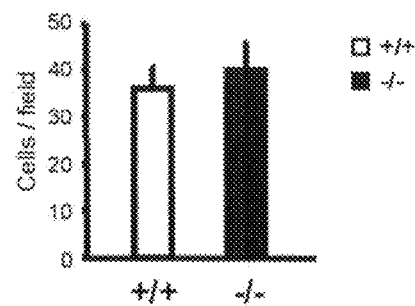
Figure 11C:
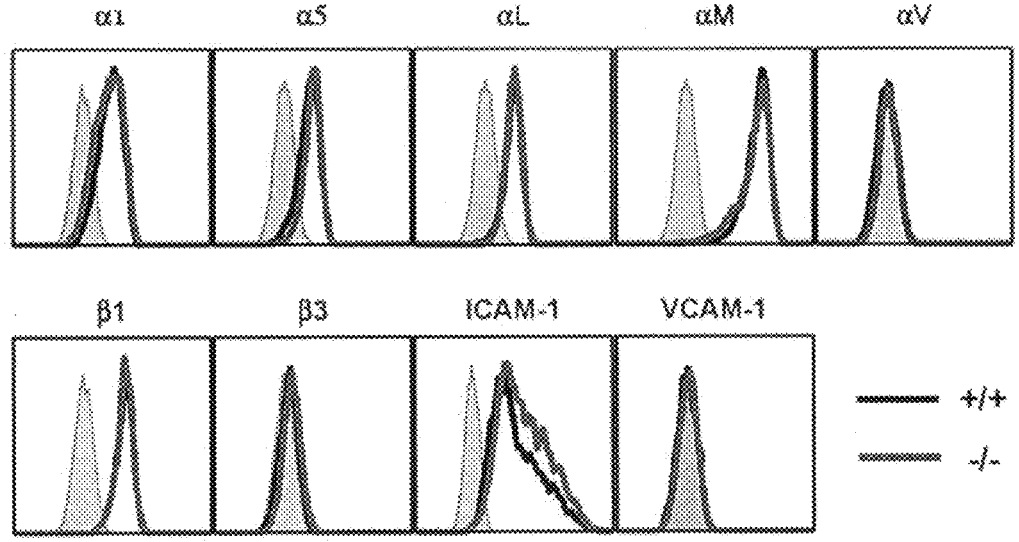
Figure 11D:
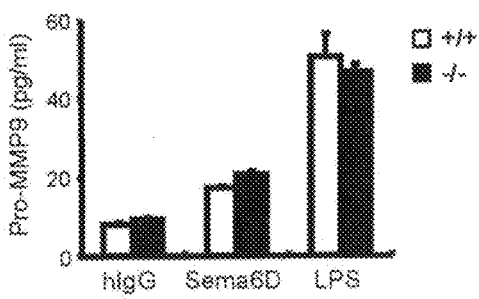
Figure 11E:
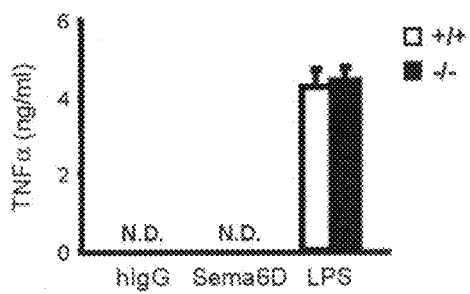

It has recently been suggested that myosin II and small DTPases in the Rho family play a role in dendritic cell trafficking. Localization of these molecules resembles that of Plexin-A1, implying that they are necessary for squeezing the cell body and producing actomyosin contractions as the cell passes through narrow gaps or constricted regions. Myosin light chain (MLC) phosphorylation is also important for myosin II activity, and may be involved in Sema3A-mediated axonal retraction. In light of these previous findings and the abundant expression of Sema3A in the lymph channels, we investigated whether or not Sema3A affects myosin II activity during dendritic cell trafficking. As expected, there was an increase in MLC phosphorylation in dendritic cells stimulated with recombinant Sema3A (FIG. 4C, FIG. 10). Moreover, Sema3A increased the percentage of motile dendritic cells, and the velocity of the dendritic cells in the collagen matrix (which is used as an in vitro model of migration through constricted regions) (FIG. 4D).

Figure 4E:
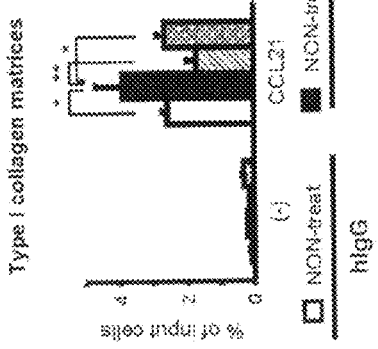

To determine whether the effect of Sema3A on dendritic cell trafficking is dependent on myosin II, myosin II or its upstream activator Rho kinase was inhibited with a drug. As shown in FIG. 4E, dendritic cell trafficking increased significantly when Sema3A was applied to the upper chamber, but this effect disappeared when the DC cells were treated with either the myosin II inhibitor blebbistatin or the Rho kinase inhibitor Y-27632.

Taken together, these results suggest that Sema3A induces actomyosin contractions during dendritic cell trafficking.

FIG. 1. Plexin-A1$^{-/-}$ Mice Exhibit Diminished T-Cell Response Due to Deficient Migration of Dendritic Cells to the Lymph Channels (A) Decreased Production of Antigen-Specific T-Cells in Plexin-A1$^{-/-}$ Mice OT-IICD4$^+$ T-cells labeled with CFSE were injected intravenously into wild-type (+/+) or Plexin-A1$^{-/-}$ (−/−) mice, and OVA peptide in CFA was then injected subcutaneously into the foot pads. After 72 hours, the antigen-specific T-cell response was measured by CFSE dilution. The data for each test are typical examples from three independent experiments.

(B) Decreased Dendritic Cell Trafficking to Draining Lymph Nodes in Plexin-A1$^{-/-}$ Dendritic Cells CMTMR-labeled BMDC cells from wild-type (+/+) or Plexin-A1$^{-/-}$ (−/−) mice were injected into the foot pad of a wild-type recipient mice, and CD4$^+$ OT-IIT cells (green) labeled with CMFDA were injected into the mouse. 24 hours after injection, dendritic cell trafficking to the popliteal lymph nodes was measured with a two-photon microscope.

(C) Decreased Number of Migrating Dendritic Cells in Plexin-A1$^{-/-}$ Mice

CFSE-labeled BMDC cells from wild-type (white bar) or Plexin-A1$^{-/-}$ (black bar) mice were injected into the foot pad of a wild-type recipient mouse. The number of dendritic cells transported to the popliteal lymph nodes was analyzed by the following formula: (% influx cells) (total cells)×(% CFSE+ cells)/(number of influx cells). Average+/−sd, p<0.01, *p<0.001, Mann-Whitney U-Test (D) Decreased Migration Activity of Endogenous Dendritic Cells in Plexin-A1$^{-/-}$ Mice FITC isomer was painted on the shaved shoulders of wild-type (white bar) and Plexin-A1$^{-/-}$ (black bar) mice. Cells were isolated from the brachial lymph nodes at the times indicated, and D11c$^+$ FITC$^+$ cells were counted.

FIG. 2. Decreased Passage Ability of Plexin-A1$^{-/-}$ Dendritic Cells Across Lymph Channels (A) Retention of Dendritic Cells Along Lymph Channels in Plexin-A1$^{-/-}$ Mice CFSE-labeled bone marrow dendritic cells (green) from wild-type (+/+) or Plexin-A1$^{-/-}$ (−/−) mice were injected intracutaneously into the ear tissues of mice that had been sensitized in advance by oxazolone injection. After 24 hours the ears were excised, and the specimen was stained by whole mount staining (top) using biotinylated anti-LYVE-1 antibodies having streptavidin-Cy3 (red), and the residual dendritic cells in the visual field were counted (bottom). ***p<0.001, Mann-Whitney U-test.

(B) Decreased Ability of Dendritic Cells to Pass Through Lymphatic Endothelial Cell Monolayer in Plexin-A1$^{-/-}$ Dendritic Cells BMDC cells from wild-type (+/+) or Plexin-A1$^{-/-}$ (−/−) mice were applied to a lymphatic endothelial cell monolayer, and the interactions between the dendritic cells and the lymphatic endothelial cells were recorded every 30 seconds with a time-lapse video microscope recorder. The yellow dotted lines show the cell junctions of the endothelial cells. White shows dendritic cells in contact with lymphatic endothelial cells. Red shows the migration process observed in wild-type dendritic cells.

(C) Decreased Migration Ability in Plexin-A1$^{-/-}$ Dendritic Cells

CFSE-labeled dendritic cells were applied to an endothelial cell monolayer, incubated and fixed for 45 minutes, and stained with Alexa 546 conjugated phalloidin. Confocal microscope images were obtained with an optical section spacing (z-spacing) of 0.22 μm. Wild-type dendritic cells penetrated from the apex to the base, but Plexin-A1$^{-/-}$ dendritic cells did not reach the basal level (left). In terms of quantity of dendritic cell trafficking (right), the number of dendritic cells adhering to the lymphatic endothelial cell monolayer (white bar) and the number of dendritic cells that migrated across the lymphatic endothelial cell monolayer (black bar) were measured with a confocal microscope. The number of migrating dendritic cells was calculated as a percentage of the total dendritic cells. Average+/−sd, *p<0.001, Student's t-test (D) Decreased Chemokine-Induced Migration Ability in Plexin-A1$^{-/-}$ Dendritic Cells During Passage Through a Lymphatic Endothelial Cell Monolayer Dendritic cells from wild-type (white bar) or Plexin-A1$^{-/-}$ (black bar) mice were applied to the upper chamber of a Transwell (pore diameter: 5 μm) overlaid with lymphatic endothelial cells, and chemotaxis in response to CCL21 was measured. Average+/−sd, *p<0.001, Student's t-test FIG. 3. Sema3A-NP-1-Plexin-A1 Interaction is Responsible for Dendritic Cell Trafficking Via Plexin-A1/NP-1

(A) NP-1 Expressed in Dendritic Cells is Responsible for Dendritic Cell Trafficking Dendritic cells of wild-type (white bar), NP-1 knock-in (Sema3A binding site destroyed) or Sema6D$^{-/-}$ (black bar) mice were adoptively transferred into wild-type recipient mice. Only the dendritic cells from NP-1$^{-/-}$ knock-in mice exhibited diminished dendritic cell trafficking. Average+/−sd, *p<0.05, Mann-Whitney U-test (B) Sema3A Expressed in Lymph Channels is Responsible for Dendritic Cell Trafficking Dendritic cells from wild-type mice were adoptively transferred into wild-type (+/+) and Sema3A$^{-/-}$, Sema6C$^{-/-}$ or Seiha6D$^{-/-}$ mice. Only the Sema3A$^{-/-}$ recipient mice exhibited diminished dendritic cell trafficking. Data were obtained from three independent experiments. Standard error+/−95% confidence interval, **p<0.01, Mann-Whitney U-test (C) Like the Plexin-A1$^{-/-}$ Dendritic Cells, Dendritic Cells with NP-1 Abnormalities Exhibited Diminished Migration (but not with Sema6D)

As discussed above, dendritic cells derived from wild-type (white bar) and NP-1 knock-in or Sema6D$^{-/-}$ (black bar) mice were applied to the upper chamber of a Transwell (pore diameter 5 μm) overlaid with lymphatic endothelial cells, and chemotaxis in response to CCL21 was measured. Average+/−sd, p<0.01, Student's t-test (D) Decreased T-Cell Stimulation was Observed in Sema3A$^{-/-}$ and NP-1 Knock-in Mice, but not in Sema6C$^{-/-}$ and Sema6D$^{-/-}$ Mice To investigate antigen-specific T-cell stimulation, Sema3A$^{-/-}$, NP-1 knock-in, Sema6C$^{-/-}$, Sema6D$^{-/-}$ (black circle) and wild-type (white circle) mice were immunized with KLH in CFA, and the CD4$^+$ T-cell response to KLH was investigated in vitro. Average+/−sd, p<0.01, ***p<0.001, Student's t-test FIG. 4. Sema3A Induces MLC Phosphorylation and Promotes Actomyosin Contractions Necessary for Migration of Dendritic Cells Through Constricted Regions (A) Plexin-A1 is Localized in the Trailing Edge of Dendritic Cells Dendritic cells were fixed, and stained with Alexa 488 conjugated phalloidin (green) and anti-Plexin-A1 polyclonal antibodies+anti-rabbit IgG-Cy3 (red). Scale bar represents 10 μm (top panel). Localization of Plexin-A1 and F-actin was assayed by measuring the fluorescent intensity of the cells shown in the top panel (lower panel). The percentage of non-colocalized cells is shown (right panel). Data are typical examples from three independent experiments.

(B) Sema3A Increases Dendritic Cell Trafficking in Response to Chemokines (Left and Center)

A dendritic cell migration assay was performed. Recombinant Sema3A protein was applied to either the lower (left) or upper (center) chamber, with CCL21 in the lower chamber. Average+/−sd, **$p<0.01$, two-sided Student's t-test.

(Right) Recombinant Sema3A (black bar, black circle) or control IgG (white bar, white circle) was applied to the side opposite the CCL21, and a two-dimensional dendritic cell chemotaxis assay was performed using EZ-taxiscan. The instantaneous velocity of the migrating fraction of dendritic cells was analyzed with MetaMorph software (right panel). ***$p<0.001$, Mann-Whitney U-test. Data are typical examples from three independent experiments.

(C) Sema3A Induces MLC Phosphorylation

Dendritic cells on fibronectin-coated glass were treated with 5 µg/ml of hIgG (left panel) or Sema3A-Fc (right panel). After 10 minutes, the cells were fixed and stained with anti-pMLC antibodies+anti-rabbit IgG-Cy3 (bottom). The confocal microscope image consists of eight z-stack images with an optical section spacing (z-spacing) of 0.2 µm, with the z-stack images projected onto one image. Scale bar represents 10 µm.

(D) Sema3A Accelerates Dendritic Cell Migration Velocity in 3D-Collagen Matrix

The migration velocity of a single dendritic cell in a type I collagen matrix in response to chemokines with or without the presence of Sema3A was analyzed by time-lapse microscope imaging, and the single dendritic cell velocity was determined with MetaMorph software. The average cell velocity (left panel, n=64) and instantaneous velocity distribution (right panel) are shown. ***$p<0.001$, Mann-Whitney U-test. Data represent typical examples from three independent experiments.

(E) Recombinant Sema3A Promotes Dendritic Cell Trafficking, an Effect that is Eliminated by Blocking Myosin II Activity BMDC cells that had been treated for 30 minutes at 37° C. with 50 µM of blebbistatin or 30 µM of Y-27632 were applied to the upper chamber of a Transwell (pore diameter: 5 µm) overlaid with 3 mg/ml of type 1 collagen (left panel) and an HMVEC-dLy monolayer (right panel), and chemotaxis in response to CCL21 was measured in the upper chamber with and without Sema3A. The overall difference between groups was evaluated by one-way ANOVA. Post facto multiple comparison was by Tukey test. *$p<0.05$, **$p<0.01$.

Figure 5A:
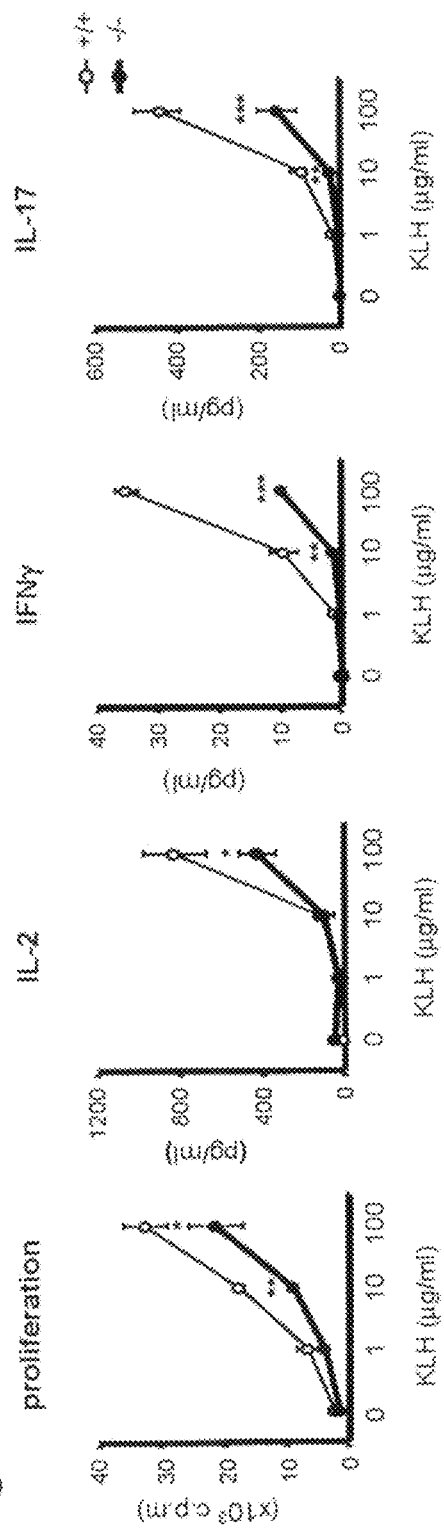
FIG. 5 shows a decrease in antigen-specific T-cell stimulation in Plexin-A1$^{-/-}$ mice.
Figure 5C:
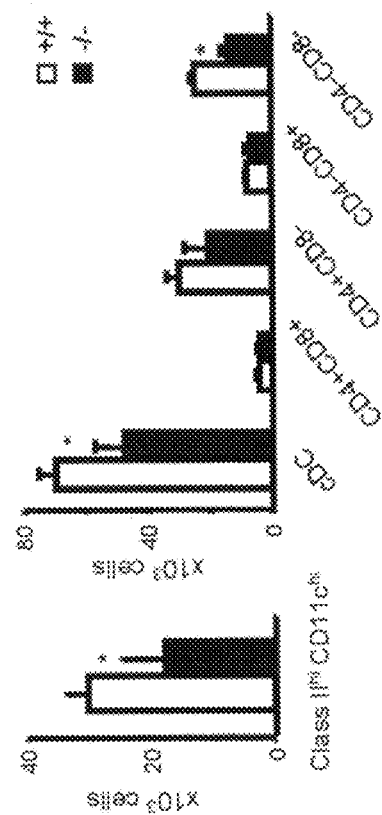
Figure 5B:
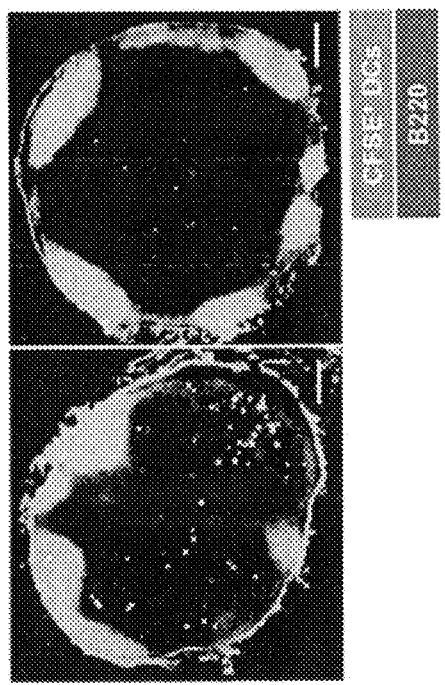

FIG. 5. Diminished Antigen-Specific T-Cell Stimulation in Plexin-A1$^{−/−}$ Mice (A) 100 µg of keyhole limpet hemocyanin (KLH) in CFA was injected into the hind foot pads of wild-type (+/+) and Plexin-A1$^{−/−}$ (−/−) mice to immunize the mice. 5 days after immunization, CD4$^+$ T-cells isolated from the draining lymph nodes were stimulated for 72 hours with various concentrations of KLH and irradiated APC. For the proliferation assay, the cells were pulsed with 2 µCi of $^3$H-thymidine during the last 14 hours. Secretion of IL-2, IFNγ and IL-17 was measured with Cytokine Plex (BioRad). Average+/−sd, *$p<0.05$, $p<0.01$ and *$p<0.001$, two-sided Student's t-test.

(B) Almost No Migrated Dendritic Cells Observed in T-Cell Region 24 hours after injection of CFSE-labeled dendritic cells from wild-type (+/+) or Plexin-A1$^{−/−}$ (−/−) mice, the popliteal lymph nodes were isolated, and stained with phycoerythrin (PE)-conjugated anti-B220. Localization of migrated dendritic cells was observed by fluorescent microscopy. Scale bar shows 100 µm.

(C) Number of Migrating Dendritic Cell Subsets is Lower in Steady-State Draining Lymph Nodes of the Skin in Plexin-A1$^{−/−}$ Mice The draining lymph nodes of the skin were isolated from 8-week-old non-inflamed wild-type mice (white bar) or Plexin-A1$^{−/−}$ mice (black bar) (n=4). Single-cell suspensions were stained with antibodies against CD11c, B220, CD4, CD8a and I-A$^b$, and after gate setting for the CD11c$^+$ B220$^−$ population, the cells were analyzed by flow cytometry. Average+/−S.E.M., *$p<0.05$, two-sided Student's t-test FIG. 6. FITC-Dextran Uptake and Responses to Chemokines are Unaffected in Plexin-A1$^{−/−}$ Dendritic Cells (A) Plexin-A1$^{−/−}$ dendritic cells uptake antigens to the same degree as wild-type dendritic cells. BMDC cells from wild-type mice (white circle) or Plexin-A1$^{−/−}$ mice (black circle) were stained with APC anti-CD11c, and cultured for the times shown at 37° C. with FITC-dextran (thick line). The ratio of FL1 fluorescent positive cells to CD11c$^+$ cells was analyzed by flow cytometry. Cells cultured with FITC-dextran on ice were used as a control.

(B) Normal Response to Chemokines in Transwell Assay

Dendritic cells from wild-type (white bar) or Plexin-A1$^{−/−}$ (black bar) mice were added to the upper chamber of a Boyden chamber (pore diameter 5 µm), and the number of cells that migrated to the lower chamber in response to CCL21, CCL19 or CXCL12 was counted.

(C) Normal Direction Sensing by Dendritic Cells in Response to Chemokines

Dendritic cells from wild-type (+/+) or Plexin-A1$^{−/−}$ (−/−) mice were made to adhere to a cover slip coated with fibronectin, and placed in a CCL21 gradient in a Zigmond chamber. Dendritic cell trafficking was recorded every 30 seconds with a confocal stop-motion video microscope recorder. The images were analyzed with NIB ImageJ software. The scatter plot shows the positions of wild-type (+/+) and Plexin-A1$^{−/−}$ (−/−) cells after 60 seconds of migration in the CCL21 gradient, relative to their original positions. The results are shown as a percentage of cells that stopped within a 30° arc moving towards the CCL21 source.

(D) Comparison of Expressed Levels of CCR7 and CXCR4

Expression of CCR7 and CXCR4 in dendritic cells from wild-type (+/+, black line) or Plexin-A1$^{−/−}$ (−/−, red line) mice and an isotype control (grey region) were measured by flow cytometry.

FIG. 7. Decrease in Ability to Pass Through Endothelial Cell Monolayer in Plexin-A1$^{−/−}$ Cells BMDC cells from wild-type (+/+) and Plexin-A1$^{−/−}$ (−/−) mice were labeled with CFSE (green), and applied to an HMVEC-dLy monolayer. After 45 minutes of incubation, they were fixed with paraformaldehyde, and stained with Alexa 546 conjugated phalloidin (red). Confocal microscope images were taken with a 0.2 µm optical section spacing (z-spacing). The scale bar represents 10 µm.

FIG. 8. Expression Profiles of Plexin-A1 and Related Molecules in Dendritic Cells and Lymphatic Endothelial Cells Expression of Plexin-A1-related genes in dendritic cells and lymph channels was measured by RT-PCR. Expression of G3PDH was measured as a control.

FIG. 9. Preparation of Sema6D$^{−/−}$ Mice (A) Disruption of Sema6D Gene

The genetic structures of a wild-type Sema6D allele (top), a Sema6D targeting construct (middle) and the resulting Sema6D targeted allele (bottom) are shown. The black boxes represent exons. A 0.6 kb fragment containing the start codon was replaced with Neo. The HSV-TK gene was added to allow selection from random integration. E, EcoR1.

(B) Genome PCR Analysis

Genome DNA isolated from the tails of wild-type (+/+), heterozygous (+/−) and homozygous (−/−) mutant mice was evaluated by PCR using the primers shown (arrows). The 0.7 kbp fragment represents the wild allele, and the 1.3 kbp fragment represents the targeted allele.

(C) RT-PCR Analysis

RT-PCR was performed using cDNA isolated from spleens, and Sema6D gene expression was measured.

(D) BMDC cells from wild-type (+/+) and homozygous (−/−) mice were stained with phycoerythrin-conjugated anti-CD11c and biotinylated anti-Sema6D mAb (solid line), or with an isotype matching control (dotted line)+allophycocyanin-conjugated streptavidin. Sema6D expression was investigated by flow cytometry under CD11c-positive cell gate settings.

FIG. 10. Sema3A Induced Myosin Light Chain Phosphorylation (A) Contour Image of Two-Dimensional Rendering of Three-Dimensional Surface Graph Showing the Intensity Range BMDC cells on fibronectin-coated glass were stimulated for 10 minutes at 37° C. with 5 µg/ml of human IgG (lower panel) or recombinant Sema3A-Fc protein (upper panel). The cells were fixed, and stained with rabbit anti-pMLC+ anti-rabbit Cy3. Images were obtained by confocal microscopy from eight z-stack images with an optical section spacing (z-spacing) of 0.2 mm, with the z-stack images projected onto one image, which was a 3D surface graph rendered as a 2D graph showing a range of single values.

(B) Distribution of average intensity frequency (left axis) or cumulative fraction (right axis) in the region of the dendrites of dendritic cells stimulated with hIgG (white bar, white circle) or Sema3A-Fc (black bar, black circle). (n=80), p<0.001, Mann-Whitney U-test. Data are typical examples from three independent experiments.

FIG. 11. No Significant Difference Between Wild-Type and Plexin-A1$^{−/−}$ dendritic cells in adhesion activity and TNFα and pro-MMP9 secretion (A,B) Adhesion Activity with Respect to the Extracellular Matrix (A) and Endothelial Cells (B) was Similar for Wild-Type and Plexin-A1$^{−/−}$ Dendritic Cells (A) Calcein AM-labeled BMDC cells from wild-type (white bar) and Plexin-A1$^{−/−}$ (black bar) mice were applied to a plate (BD Bioscience) coated with extracellular matrix. After 30 minutes of incubation, non-adhering cells were thoroughly removed, adhering cells were solubilized with 100 µl of dissolving buffer containing 0.2% Triton X, and fluorescent absorbency at 460 nm was assayed with a spectrometer. The values are expressed as percentages relative to the fluorescent absorption of the total input cell extract.

(B) $1 \times 10^5$ calcein-AM-labeled BMDC cells from wild-type (white bar) and Plexin-A1$^{−/−}$ (black bar) mice were applied to a monolayer of lymphatic endothelial cells (SVEC4-10). After 30 minutes of incubation, the cells were fixed for 20 minutes with 4% PFA, and thoroughly washed. The values show numbers of cells adhering to endothelial cells in the visual field of a fluorescent microscope. The cells were counted with NIS-elements AR 3.0 software.

(C) The expressed level of integrin did not differ between the wild-type and Plexin-A1$^{−/−}$ dendritic cells. BMDC cells from wild-type (black line) and Plexin-A1$^{−/−}$ (red line) mice were stained with CD11c-FITC and biotinylated anti-integrin antibodies+APC conjugated streptavidin. The expressed level was measured by flow cytometry.

(D,E) There was no difference between wild-type and Plexin-A1$^{−/−}$ dendritic cells in the levels of TNFα and pro-MMP9 secretion. BMDC cells from wild-type (white bar) and Plexin-A1$^{−/−}$ (black bar) mice were cultured for 48 hours with LPS and 5 µg/ml of hIgG or recombinant Sema6D-Fc coated on a plate. The concentrations of pro-MMP9 (D) and TNFα (E) were measured by ELISA.

Contact Dermatitis Mouse Model

Contact dermatitis can be induced in mice using various contact allergens including dinitrofluorobenzene (DNFB) and oxazolone. Mice were locally sensitized with the allergen in a vehicle consisting of acetone and olive oil, and the ears were challenge inoculated with the allergen dissolved in only olive oil. Changes in ear thickness are a measure of immune response to the antigen. Neuropilin-1-Fc is administered during the sensitization period (days 0 to 5) and the challenge inoculation period (days 5 to 6). The role of Neuropilin-1-Fc in suppression of contact dermatitis will be evaluated by observing suppression of ear thickening by Neuropilin-1-Fc.

On day 0, 0.5% DNFB in acetone:olive oil (4:1) or the acetone:olive oil alone is painted on the backs of C57B1/6 mice. On day 5, the ear thicknesses are measured with calipers, and 25 µl of solution is dripped on the ears to challenge inoculate the mouse ears with either olive oil alone (control) or 0.25% DNFB in olive oil. Changes in ear thickness are measured on day 6, and inflammation is calculated as the difference in ear thickness between days 5 and 6. The test mice are given local intraperitoneal or intravenous injections of PBS or Neuropilin-1-Fc either from day 0 to day 5 or from day 5 to day 6.

Neuropilin-1-Fc suppresses ear thickening, suggesting that Neuropilin-1-Fc can be useful in suppressing contact dermatitis.

Example 2

To evaluate the role of Plexin-A1 in cell migration in vivo, dendritic cells collected from wild-type or Plexin-A1 knock-out mice and labeled with CFSE were adoptively transferred into the dermis of mice treated with oxazolone. The behavior of the transferred dendritic cells was then monitored.

Adoptive transfer was performed by the following methods. Dendritic cells from bone marrow were labeled for 10 minutes at 22° C. in 5 µM of CFSE (carboxyfluorescein diacetate succinimidyl ester). The cells were then washed with PBS. $1 \times 10^6$ dendritic cells suspended in PBS were subcutaneously injected into the foot pads of recipient mice. 24 and 48 hours after injection, the popliteal lymph nodes were collected. The lymph nodes were treated for 30 minutes at 37° C. with 1 mg/ml of collagenase D. The cell numbers were counted and analyzed by flow cytometry. As described in Cavanagh et al. (Nat. Immunol. (2005) 6, 1029-1037), the percentage of migrating dendritic cells corresponds to the fluorescent labeled dendritic cells as a percentage of total lymph node cells.

Oxazolone treatment is provided as a model of a contact hypersensitivity. To analyze migration of dendritic cells from peripheral sites, contact hypersensitivity was induced by oxazolone treatment of the abdomen as described in Johnson et al. (J. Exp. Med. (2006) 203, 2763-2777). 6 days after sensitization, the ears were treated with oxazolone. 8 hours after treatment, $1 \times 10^6$ CFSE-labeled bone marrow-derived dendritic cells were injected percutaneously. After 24 hours the mice were sacrificed, and the ear tissues were fixed in paraformaldehyde. For purposes of lymph node detection, the whole mount preparations were stained with biotinylated LYVE-1 antibodies (R & D Systems) and streptavidin-indocarbocyanin. Images were taken by confocal z-stack imaging, and the number of cells remaining in the periphery was measured.

24 hours after adoptive transfer, a significant quantity of dendritic cells from Plexin-A1knockout mice remained along lymph channels that were positive for the lymphatic endothelial cell marker LYVE-1 in the skins of the recipient mice (FIG. 12a). This behavior was not observed with the wild-type dendritic cells. The results suggest that dendritic cells from Plexin-A1knockout mice are deficient in the ability to migrate through lymph nodes.

Time-lapse imaging was used to test whether or not Plexin-A1 deficiency in dendritic cells affects the initial contact between the dendritic cells and the epithelial cells of the lymph nodes. Wild-type dendritic cells interacted with the lymphatic endothelial cells at the intercellular junctions of the endothelial cells, and passed through the endothelial cells (FIG. 12b). The dendritic cells from a Plexin-A1 deficient source moved as actively as the wild-type dendritic cells, extended their dendrites, and made contact with the lymphatic endothelial cells, but were not able to pass through the lymphatic endothelial cells (FIG. 12b).

To confirm these observations, CFSE-labeled dendritic cells were added to a monolayer of lymphatic endothelial cells stained with the F-actin marker phalloidin, and the cells were monitored by confocal z-stack imaging. As a result, wild-type dendritic cells were observed on both the upper and lower surfaces of the endothelial cells. By contrast, Plexin-A1 deficient dendritic cells were able to contact the lymphatic endothelial cells, but were unable to pass through the cell layer (FIG. 12c).

A Transwell test was performed by the following methods. An uncoated Transwell insert (pore diameter 5 μm, Corning) was installed in a 24-well plate with each well filled with CCL19, CCL21 or CXCL12 in 0.6 ml of RPMI containing 0.1% BSA. A suspension of dendritic cells (1×10$^5$ cells in 0.1 ml) was added to the upper well of the Transwell, and incubated for 3 hours at 37° C. The cells in the lower chamber were ablated for 5 minutes by treatment with 5 mM of PBS-EDTA, and counted by Guava ViaCount assay on a Guava PCA system. For purposes of in vitro cell migration assay, fibronectin (10 μg/ml) type I collagen (3.0 mg/ml) or lymphatic endothelial cells were coated on the upper chamber membrane. SVEC4-10 mouse lymphatic endothelial cells (2×10$^4$ cell count) or human skin lymphatic microvascular endothelial cells were seeded on the top or bottom surface of a Transwell insert coated with fibronectin (2 μg/ml). After 2 days of culture, the integrity of the layer of confluent cells was determined by phalloidin staining. A cell migration assay was performed for 6 hours by the methods described in Ledgerwood et al. (Nat. Immunol. (2008) 9, 42-53). As described in Lammermann et al. (Nature (2008) 453, 51-55), myosin II or the Rho kinase ROCK was inhibited by treating dendritic cells for 30 minutes at 37° C. with 50 μM of blebbistatin or 30 μM of Y-27632.

Plexin-A1 deficient dendritic cells also exhibited much lower chemokine-induced migration ability through a monolayer of endothelial cells (FIG. 12d).

In summary, these results suggest that Plexin-A1 plays an important role in migration through lymph channels.

FIG. 12a-1 shows a confocal z-stack image of CFSE-labeled wild-type and Plexin-A1 deficient bone-marrow derived cells injected percutaneously into the ear tissue of sensitized mice. 24 hours after injection of dendritic cells, the whole mount was stained with biotinylated anti-LYVE-1 antibodies and streptavidin-indocarbocyanin (red), and evaluated. The scale bar represents 50 μm.

FIG. 12a-2 is a graph showing the dendritic cells remaining in the visual field shown in FIG. 12a-1. Individual symbols represent individual fields, and red circles represent average values. *P<0.001 (Mann-Whitney U-test).

FIG. 12b shows migration of wild-type and Plexin-A1 deficient bone marrow-derived dendritic cells across a monolayer of lymphatic endothelial cells. The data were recorded every 30 seconds as interaction observed by stop-motion video microscopy. The yellow broken lines show endothelial cell junctions, and the white arrows represent dendritic cells in contact with lymphatic endothelial cells. The red arrows show the migration progress of wild-type dendritic cells. The scale bar represents 50 μm.

FIG. 12c-1 shows confocal microscope images of wild-type and Plexin-A1 deficient bone marrow-derived dendritic cells. The cells were added to an endothelial cell monolayer, incubated for 45 minutes, fixed, and stained with Alexa Fluor 546 conjugated phalloidin. The images were obtained with a 0.22 μm optical section spacing (z-spacing).

FIG. 12c-2 shows quantified (average+/−sd) migration of dendritic cells represented as percentage of migrating dendritic cells relative to total dendritic cells. *p<0.001 (Student's test).

FIG. 12d is a graph showing the migration ability of wild-type and Plexin-A1 deficient dendritic cells across a Transwell insert with a monolayer of lymphatic endothelial cells (pore diameter 5 μm) in response to CCL21 at concentration gradient. *p<0.001 (Student's test). The data are representative values from three tests (average+/−sd).

[Sequence Listing]

---

The invention claimed is:

1. A method for screening a Sema3A neutralizing antibody, the method comprising:
- (a) contacting a Sema3A polypeptide with eukaryotic cells expressing Neuropilin-1 and Plexin-A1, in the presence of a Sema3A antibody;
- (b) measuring a signal produced by an interaction between the Sema3A polypeptide and the eukaryotic cells expressing Neuropilin-1 and Plexin-A1 in the presence of the Sema3A antibody, and comparing the signal with a control signal produced by an interaction between the Sema3A polypeptide and the eukaryotic cells expressing Neuropilin-1 and Plexin-A1 in the absence of the Sema3A antibody; and
- (c) selecting a Sema3A antibody that reduces the signal in comparison to the control signal,
- wherein the Sema3A antibody that reduces the signal in comparison to the control signal is identified as a Sema3A neutralizing antibody, and
- wherein the Sema3A neutralizing antibody inhibits T cell activation.

2. The method of claim 1, wherein the eukaryotic cells are dendritic cells.

3. The method of claim 2, wherein the dendritic cells are cells fractionated and induced from peripheral blood.

4. The method of claim 2, wherein the dendritic cells are cells of a cell line.

5. The method of claim 1, wherein the signal is Rho kinase activation.

6. The method of claim 1, wherein the signal is myosin II phosphorylation.

7. The method of claim 1, wherein the signal is actomyosin contraction.

8. The method of claim 2, wherein the signal is transmigration of the dendritic cells.

9. The method of claim 1, wherein the produced signal is a measure of an interaction between the Sema3A polypeptide and a Neuropilin-1/Plexin-A1 heteroreceptor expressed by the eukaryotic cells.

* * * * *